United States Patent
Elkon et al.

(10) Patent No.: US 10,329,258 B2
(45) Date of Patent: Jun. 25, 2019

(54) CGAS IN SYSTEMIC LUPUS ERYTHEMATOSUS (SLE)

(71) Applicant: UNIVERSITY OF WASHINGTON, Seattle, WA (US)

(72) Inventors: Keith Elkon, Seattle, WA (US); Jie An, Seattle, WA (US); Mark Minie, Seattle, WA (US); Tomikazu Sasaki, Seattle, WA (US); Joshua J. Woodward, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 15/564,995

(22) PCT Filed: Apr. 26, 2016

(86) PCT No.: PCT/US2016/029396
§ 371 (c)(1),
(2) Date: Oct. 6, 2017

(87) PCT Pub. No.: WO2016/176222
PCT Pub. Date: Nov. 3, 2016

(65) Prior Publication Data
US 2018/0086713 A1    Mar. 29, 2018

Related U.S. Application Data

(60) Provisional application No. 62/155,389, filed on Apr. 30, 2015.

(51) Int. Cl.
| | | |
|---|---|---|
| *C07D 219/12* | (2006.01) | |
| *A61K 31/4353* | (2006.01) | |
| *C07D 403/12* | (2006.01) | |
| *C07D 219/10* | (2006.01) | |
| *C07D 401/12* | (2006.01) | |
| *C07D 405/12* | (2006.01) | |

(52) U.S. Cl.
CPC ........ *C07D 219/12* (2013.01); *A61K 31/4353* (2013.01); *C07D 219/10* (2013.01); *C07D 401/12* (2013.01); *C07D 403/12* (2013.01); *C07D 405/12* (2013.01)

(58) Field of Classification Search
CPC .. C07D 219/12; C07D 219/10; C07D 403/12; C07D 401/12; A61K 31/4353
See application file for complete search history.

(56) References Cited

U.S. PATENT DOCUMENTS

| | | |
|---|---|---|
| 5,453,431 A | 9/1995 | Gilman |
| 2007/0232622 A1 | 10/2007 | Lipford et al. |
| 2013/0102627 A1 | 4/2013 | Higgins et al. |
| 2013/0230534 A1 | 9/2013 | Cardarelli et al. |
| 2015/0023930 A1 | 1/2015 | Rawat et al. |

FOREIGN PATENT DOCUMENTS

| | | |
|---|---|---|
| WO | 2010030671 A1 | 3/2010 |
| WO | 2013101771 A2 | 7/2013 |

OTHER PUBLICATIONS

Hoffmann, Mutagenesis, vol. 24(4), 317-329, 2009. (Year: 2009).*
Csuk, Arch Pharm CHem Life Sci, vol. 342, 699-709, 2009. (Year: 2009).*
Castillo, E J MEd Chem, 44, 4826-4840, 2009. (Year: 2009).*
Schreiber, J Biol CHem, 292(18), 7285-7294, 2017. (Year: 2017).*
Crow, Transl Res, 165(2), 296-305, 2015. (Year: 2015).*
TAS, CA167:378466, abstract only of Cutaneous and OCular Toxicology, 35(1), 83-84, 2016. (Year: 2016).*
Conigliaro, Autoimmunity, May 2010, 43(3), 220-225. (Year: 2010).*
Pubchem Substance Summary for CID 2786625, deposit date on Jul. 19, 2005 (Jul. 19, 2005) 1-48; 50-68 p. 1-11.
Sabolova D. et al. 'Determination of the binding affimties of plasmid DNA using fluorescent intercalators possessing an acridine skeleton', International Journal of Biological Macromolecules (2006) vol. 38, pp. 94-98. Abstract; p. 95, Table 1.
The International Search Report (ISR) for PCT/US2016/029396 dated Jun. 27, 2016, pp. 1-4.
International Written Opinion for PCT/US2016/029396 dated Jun. 27, 2016, pp. 1-6.
An et al., Expression of Cyclic GMP-AMP Synthase in Patients With Systemic Lupus Erythematosus, Arthritis & Rheumatology, 69(4): 800-807 (2017).
Pullen, Role of Cyclic GMP-AMP Synthase Explored in Patients With SLE, Arthritis & Rheumatology, In this Issue, 69(4): A13-A14 (2017).a (Continued)

*Primary Examiner* — D Margaret M Seaman
(74) *Attorney, Agent, or Firm* — McDonnell Boehnen Hulbert & Berghoff LLP

(57) ABSTRACT

The present invention provides therapeutic strategies for treatment of severe debilitating diseases associated with IFN-I due to cGAS activation. In one aspect, the invention provides compounds of Formula (I): [Formula should be inserted here] and pharmaceutical uses thereof. In another aspect, the invention provides methods for treating an autoimmune disease or a monogenic disorder by administering an effective amount of a compound of Formula (I).

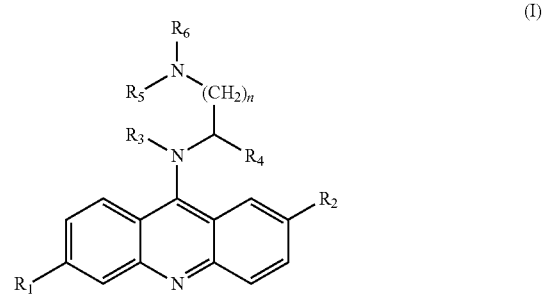

21 Claims, 16 Drawing Sheets
Specification includes a Sequence Listing.

(56) References Cited

OTHER PUBLICATIONS

An et al., Inhibition of Cyclic GMP-AMP Synthase Using a Novel Antimalarial Drug Derivative in Trex1-Deficient Mice, Arthritis & Rheumatology, 70(11):1807-1819 (2018).
Lovgren et al. "Induction of Interferon-alpha by Immune Complexes or LiposomesContaining Systemic Lupus Erythematosus Autoantigen—and Sjögren's Syndrome Autoantigen-Associated RNA," Arthritis Rheum., 54(6):1917-27 (2006).
Santer et al. "Potent induction of IFN-alpha and chemokines by autoantibodies in the cerebrospinal fluid of patients with neuropsychiatric lupus," J Immunol., 182(2):1192-201 (2009).
Martin and Elkon, "Autoantibodies make a U-turn," J Exp Med., 202(11):1465-1469 (2005).
Niewold et al. "High serum IFN-alpha activity is a heritable risk factor for systemic lupus erythematosus," Genes Immun., 8(6):492-502 (2007).
Reeves et al. "Impact of hydroxychloroquine therapy on chronic urticaria: chronic autoimmune urticaria study and evaluation," Intern Med J, 34(4):182-6 (2004).
Elkon and Wiedeman, "Type I IFN system in the development and manifestations of SLE," Current Opinion in Rheumatology, 24(5):499-505 (2012).
Crow, Y. J. & Manel, N. Aicardi-Goutières syndrome and the type I interferonopathies. Nature reviews. Immunology 15, 429-440 (2015).
Aicardi, J. & Goutières, F. A progressive familial encephalopathy in infancy with calcifications of the basal ganglia and chronic cerebrospinal fluid lymphocytosis. Ann Neurol 15, 49-54 (1984).
Crow, Y. J. et al. Characterization of human disease phenotypes associated with mutations in TREX1, RNASEH2A, RNASEH2B, RNASEH2C, SAMHD1, ADAR, and IFIH1. Am J Med Genet A 167A, 296-312 (2015).
Crow, Y. J., Vanderver, A., Orcesi, S., Kuijpers, T. W. & Rice, G. I. Therapies in Aicardi-Goutières syndrome. Clinical and experimental immunology 175, 1-8 (2014).
Stetson, D. B., Ko, J. S., Heidmann, T. & Medzhitov, R. Trex1 prevents cell-intrinsic initiation of autoimmunity. Cell 134, 587-598 (2008).
Crow, Y. J. Type I interferonopathies: mendelian type I interferon up-regulation. Current opinion in immunology 32, 7-12 (2015).
Cuadrado, E. et al. Aicardi-Goutières syndrome harbours abundant systemic and brain-reactive autoantibodies. Annals of the rheumatic diseases 74(10), 1931-9 (2014).
Gray, E. E., Treuting, P. M., Woodward, J. J. & Stetson, D. B. Cutting Edge: cGAS Is Required for Lethal Autoimmune Disease in the Trex1-Deficient Mouse Model of Aicardi-Goutières Syndrome. Journal of immunology 195, 1939-1943 (2015).
Gao, D. et al. Activation of cyclic GMP-AMP synthase by self-DNA causes autoimmune diseases. Proceedings of the National Academy of Sciences of the United States of America 112, E5699-5705 (2015).
Sjögren, H. [On knowledge of the keratoconjunctivitis sicca. VII. The sicca syndrome—an autoimmune disease]. Acta Ophthalmol (Copenh) 46, 201-206 (1968).
Lee, B. H., Tudares, M. A. & Nguyen, C. Q. Sjögren's syndrome: an old tale with a new twist. Arch Immunol Ther Exp (Warsz) 57, 57-66 (2009).
Vitali, C. et al. Classification criteria for Sjögren's syndrome: a revised version of the European criteria proposed by the American-European Consensus Group. Ann Rheum Dis 61, 554-558 (2002).
Shiboski, C. H. et al. 2016 American College of Rheumatology/European League Against Rheumatism classification criteria for primary Sjögren's syndrome: A consensus and data-driven methodology involving three international patient cohorts. Ann Rheum Dis 76, 9-16 (2017).
Tong, L., Koh, V. & Thong, B. Y. Review of autoantigens in Sjögren's syndrome: an update. J Inflamm Res 10, 97-105 (2017).
Jonsson, R., Theander, E., Sjöström, B., Brokstad, K. & Henriksson, G. Autoantibodies present before symptom onset in primary Sjögren syndrome. JAMA 310, 1854-1855 (2013).
Peck, A. B. & Nguyen, C. Q. Transcriptome analysis of the interferon-signature defining the autoimmune process of Sjögren's syndrome. Scand J Immunol 76, 237-245 (2012).
Hall, J. C. et al. Molecular Subsetting of Interferon Pathways in Sjögren's Syndrome. Arthritis Rheumatol 67, 2437-2446 (2015).
Bodewes, I. L. A. et al. Systemic interferon type I and type II signatures in primary Sjögren's syndrome reveal differences in biological disease activity. Rheumatology (Oxford) 57, 921-930 (2018).
Emamian, E. S. et al. Peripheral blood gene expression profiling in Sjögren's syndrome. Genes Immun 10, 285-296 (2009).
Gottenberg, J. E. et al. Activation of IFN pathways and plasmacytoid dendritic cell recruitment in target organs of primary Sjögren's syndrome. Proc Natl Acad Sci U S A 103, 2770-2775 (2006).
Rönnblom, L. & Eloranta, M. L. The interferon signature in autoimmune diseases. Curr Opin Rheumatol 25, 248-253 (2013).
Mavragani, C. P. et al. Defective regulation of L1 endogenous retroelements in primary Sjögren's syndrome and systemic lupus erythematosus: Role of methylating enzymes. J Autoimmun 88, 75-82 (2018).
Allenbach, Y. et al. Dermatomyositis With or Without Anti-Melanoma Differentiation-Associated Gene 5 Antibodies: Common Interferon Signature but Distinct NOS2 Expression. Am J Pathol 186, 691-700 (2016).
Baechler, E. C. et al. An interferon signature in the peripheral blood of dermatomyositis patients is associated with disease activity. Mol Med 13, 59-68 (2007).
Huard, C. et al. Correlation of cutaneous disease activity with type 1 interferon gene signature and interferon beta in dermatomyositis. Br J Dermatol 176, 1224-1230 (2017).
Wong, D. et al. Interferon and biologic signatures in dermatomyositis skin: specificity and heterogeneity across diseases. PloS one 7, e29161 (2012).
Higgs, B. W. et al. A phase 1b clinical trial evaluating sifalimumab, an anti-IFN-alpha monoclonal antibody, shows target neutralisation of a type I IFN signature in blood of dermatomyositis and polymyositis patients. Ann Rheum Dis 73, 256-262 (2014).
Moghadam-Kia, S., Aggarwal, R. & Oddis, C. V. Biologics for idiopathic inflammatory myopathies. Curr Opin Rheumatol 29, 645-651 (2017).
Brkic, Z. et al. The interferon type I signature is present in systemic sclerosis before overt fibrosis and might contribute to its pathogenesis through high BAFF gene expression and high collagen synthesis. Ann Rheum Dis 75, 1567-1573 (2016).
Kim, D. et al. Induction of interferon-alpha by scleroderma sera containing autoantibodies to topoisomerase I: association of higher interferon-alpha activity with lung fibrosis. Arthritis and rheumatism 58, 2163-2173 (2008).
Duan, H. et al. Combined analysis of monocyte and lymphocyte messenger RNA expression with serum protein profiles in patients with scleroderma. Arthritis and rheumatism 58, 1465-1474 (2008).
Keating, S. E., Baran, M. & Bowie, A. G. Cytosolic DNA sensors regulating type I interferon induction. Trends in immunology 32, 574-581 (2011).
Wahadat, M. J. et al. Type I IFN signature in childhood-onset systemic lupus erythematosus: a conspiracy of DNA- and RNA-sensing receptors? Arthritis Res Ther 20, 4 (2018).
Goldberg, A. et al. Dose-escalation of human anti-interferon-alpha receptor monoclonal antibody MEDI-546 in subjects with systemic sclerosis: a phase 1, multicenter, open label study. Arthritis Res Ther 16, R57 (2014).
Guo, X. et al. Suppression of T Cell Activation and Collagen Accumulation by an Anti-IFNAR1 mAb, Anifrolumab, in Adult Patients with Systemic Sclerosis. J Invest Dermatol 135, 2402-2409 (2015).
Marro, B. S. et al. Progression of type 1 diabetes from the prediabetic stage is controlled by interferon-alpha signaling. Proceedings of the National Academy of Sciences of the United States of America 114, 3708-3713 (2017).
Li, Q. & McDevitt, H. O. The role of interferon alpha in initiation of type I diabetes in the NOD mouse. Clinical immunology 140, 3-7 (2011).

(56) References Cited

OTHER PUBLICATIONS

Peng, R. H., Paek, E., Xia, C. Q., Tennyson, N. & Clare-Salzler, M. J. Heightened interferon-alpha/beta response causes myeloid cell dysfunction and promotes T1D pathogenesis in NOD mice. Annals of the New York Academy of Sciences 1079, 99-102 (2006).

Kallionpää, H. et al. Innate immune activity is detected prior to seroconversion in children with HLA-conferred type 1 diabetes susceptibility. Diabetes 63, 2402-2414 (2014).

Ferreira, R. C. et al. A type I interferon transcriptional signature precedes autoimmunity in children genetically at risk for type 1 diabetes. Diabetes 63, 2538-2550 (2014).

An, J. et al. Inhibition of Cyclic GMPAMP Synthase Using a Novel Antimalarial Drug Derivative in Trex1-Deficient Mice. Arthritis & Rheumatology 70(11), 1807-1819 (2018).

\* cited by examiner

CGAS IN SYSTEMIC LUPUS ERYTHEMATOSUS (SLE)

This application is a U.S. national phase of International Application No. PCT/US2016/029396, filed on Apr. 26, 2016, which claims priority to U.S. Provisional Application No. 62/155,389 filed Apr. 30, 2015, both of which are incorporated by reference herein in their entirety.

BACKGROUND OF THE INVENTION

The innate immune system senses the presence of microbes or damage via germline-encoded receptors, which detect pathogen associated molecular patterns (PAMPs) or damage-associated molecular patterns (DAMPs). Nucleic acids constitute a major molecular pattern that is recognized during infection by viruses or intracellular bacteria and that results in the stimulation of type I interferons (IFN-I) and other cytokines. However, chronic or inappropriate activation of nucleic acid-sensing pathways are also implicated in inflammatory and autoimmune diseases.

Evidence for the involvement of type I IFNs (IFN-I) in the pathogenesis of systemic autoimmune disorders such as systemic lupus erythematosus (SLE) (Elkon, K. B. and A. Wiedeman, *Type I IFN system in the development and manifestations of SLE*. Curr Opin Rheumatol, 2012. 24(5): p. 499-505) as well as in rare monogenic disorders including Aicardi-Goutierre's Syndrome (AGS) and spondyloenchondrodysplasia (SPENCD), is demonstrated by the increased expression of IFN-I stimulated genes (ISGs) in peripheral blood cells. SLE is a heterogeneous and flaring disease which can cause diseases of the skin, heart, lung, kidney, joints, nervous system etc., which make it very difficult to treat. AGS is a rare inherited 'orphan' disease that affects children. It is characterized predominantly by abnormalities in the skin and brain resulting in severe brain defects and even death in some of these children (~35% of patients die by age 15). This disease is also associated with the expression of IFN-I and some of these patients develop features similar to SLE. In a reciprocal fashion, 1-2% of SLE patients have mutations in TREX1. The association of TREX1 mutations with SLE remains the strongest single association of a gene identified so far (highest odds ratio). There is currently no effective treatment for the severe, debilitating disorder of AGS.

How, where and when IFN-I is initially stimulated, and which of the approximately 20 IFN-I subtypes are expressed in each disease, has been difficult to determine. In vitro studies (Santer, D. M., et al., *Potent induction of IFN-alpha and chemokines by autoantibodies in the cerebrospinal fluid of patients with neuropsychiatric lupus*. J Immunol, 2009. 182(2): p. 1192-201), have revealed that IFN-alpha (IFNa) is induced by SLE immune complexes (IC) containing (ribo)nucleoprotein antigens (Lovgren, T., et al., *Induction of interferon-alpha by immune complexes or liposomes containing systemic lupus erythematosus autoantigen-and Sjogren's syndrome autoantigen-associated RNA*. Arthritis Rheum, 2006. 54(6): p. 1917-27). However, the in vitro studies do not address how IFN-I may be induced prior to the formation of IC. Cytosolic DNA induces type I interferons and other cytokines which are important for antimicrobial defense but can also trigger autoimmunity. Experiments demonstrating that the serum from a significant proportion of SLE family members without autoantibodies induce ISGs in responder cells (Niewold, T. B., et al., *High serum IFN-alpha activity is a heritable risk factor for systemic lupus erythematosus*. Genes Immun, 2007. 8(6): p. 492-502) as well as incomplete neutralization of ISGs in clinical trials using biologics targeting IFN-α, suggest that other IFN-I may well be involved in SLE (Petri, M., et al., *Sifalimumab, a human anti-interferon-alpha monoclonal antibody in systemic lupus erythematosus: a phase I randomized, controlled, dose-escalation study*. Arthritis Rheum, 2013. 65(4): p. 1011-21). Moreover, in a mouse model of AGS caused by deficient expression of the 3-5' DNA exonuclease, TREX1, accumulation of intracellular DNA is responsible for cell intrinsic production of IFNb.

While many DNA sensors have been described, the recent discovery of cyclic GAMP synthase, (cGAS) (Wu. J., et al., *Cyclic GMP-AMP is an endogenous second messenger in innate immune signaling by cytosolic DNA*. Science, 2013. 339(6121): p. 826-30) (Sun, L., et al., *Cyclic GMP-AMP synthase is a cytosolic DNA sensor that activates the type I interferon pathway*. Science, 2013. 339(6121): p. 786-91), is of particular interest as it has been shown to play a pivotal role in virus-induced as well as DNA damage-induced IFN-I production. Following binding of double stranded (ds)-DNA to a positively charged pocket of cGAS, the enzyme undergoes a conformational change revealing a catalytic cleft which results in the synthesis of the cyclic dinucleotide, cyclic GMP-AMP (cGAMP) (Diner, E. J., et al., *The Innate Immune DNA Sensor cGAS Produces a Noncanonical Cyclic Dinucleotide that Activates Human STING*. Cell Rep, 2013. 3(5): p. 1355-61). cGAMP binds to the adapter protein, STING, which triggers activation of TBK, phosphorylation of IRF3 with resulting transcription of IFN-b (Sun, 2013) (Wu, 2013). In cells that are deficient in TREX1, it has recently been shown that DNA triggers IFN-b selectively through the cGAS pathway (Gao, D., et al. Activation of cyclic GMP-AMP synthase by self-DNA causes autoimmune diseases. Proc Natl Acad Sci USA 112, E5699-5705 (2015), 26371324); Gray, E. E., Treuting, P. M., Woodward, J. J., and Stetson. D. B. 2015. Cutting Edge: cGAS Is Required for Lethal Autoimmune Disease in the Trex1-Deficient Mouse Model of Aicardi-Goutieres Syndrome. J Immunol 195:1939-1943).

There remains a need in the art for treatment of severe debilitating diseases associated with IFN-I due to cGAS activation. Understanding the mechanism how cGAS/cGAMP contribute to IFN-I stimulation in SLE patients allows for directed therapeutic approaches which we are pursuing in SLE and possibly other autoimmune diseases associated with cytosolic DNA as a Danger Associated Molecular Pattern (DAMP).

SUMMARY OF THE INVENTION

Systemic Lupus Erythematosus (SLE) is strongly associated with increased expression of type I interferon (IFN-I) (Elkon, 2012). Both genetic as well as experimental studies indicate that IFN-I plays a central role in this disease (Lovgren, 2006) (Niewold. 2007). IFN-I can be stimulated by several pathways including cGAS (Cyclic di-GMP-AMP Synthase), a recently discovered cytosolic DNA sensor (Wu, 2013; Sun, 2013). cGAS is activated by ds-DNA, catalyzes the production of novel second messenger, cGAMP that potently activates type 1 IFN through STING and IRF3 pathway. The discovery of cGAS means that any microbe with DNA that stimulates gene expression by the transcription factors NF-κB and IRF3 should also signal via a cyclic dinucleotide made by the host cell via cGAS. The pathway is also likely to be important for the sensing of self DNA, which can lead to autoimmunity. Since cGAS has catalytic activity, it is possible that a small-molecule inhibitor could have therapeutic potential for autoimmune diseases.

In view of the key role that cGAS plays in DNA stimulated IFN-b production and the suspected role of this pathway in diseases associated with high expression of ISGs, in silico screening of chemical and drug libraries was performed in order to identify candidate drugs predicted to block cGAS activity. Several candidates were identified by computational analysis, including hydroxychloroquine (HCQ) and quinacrine (QC), belonging to the antimalarial class of drugs, that were predicted to interact with cGAS and ds-DNA. Studies validated that several antimalarial drugs were effective inhibitors of IFN-b production and that they functioned by inhibiting dsDNA stimulated cGAS production of cGAMP.

In an effort to identify drugs to block cGAS activity, we performed in silico screening of chemical and drug libraries and identified several commonly used antimalarial drugs for the treatment of SLE, predicted to interact strongly with cGAS by computational analysis (FIG. 1). We have verified experimentally that these antimalarial drugs block DNA binding to cGAS (FIG. 1). Antimalarial drugs including HCQ could inhibit the cGAS activity and cGAMP production in vitro (FIG. 2). More importantly, they could inhibit the type I IFN production when cells were transfected with dsDNA. Our results provide a novel mechanism of action of antimalarial drugs that are used in the treatment of Lupus and RA and other autoimmune disorders.

It has been reported that the antimalarial drugs hydroxychloroquine and quinacrine induce remissions of SLE and rheumatoid arthritis. However, despite the use of hydroxychloroquine and quinacrine as therapeutic drugs for autoimmune disease, their mechanism of action still remains unclear and controversial. Current therapy for SLE such as corticosteroids, cyclophosphamide and hydroxychloroquine were introduced several decades ago and, although used, were not approved by FDA for SLE. Benlysta (HGS/GSK) anti-BLys monoclonal antibody (mAb) is the first and only approved SLE therapy in 50 years. Although clinical outcome following Benlysta treatment was better than placebo, the difference was small. So there is still a large unmet medical need for therapeutic target identification and new drug development for effective SLE treatment. The present invention provides therapeutic strategies for treatment of severe debilitating diseases associated with IFN-I due to cGAS activation.

DETAILED DESCRIPTION OF THE INVENTION

Figure 1:
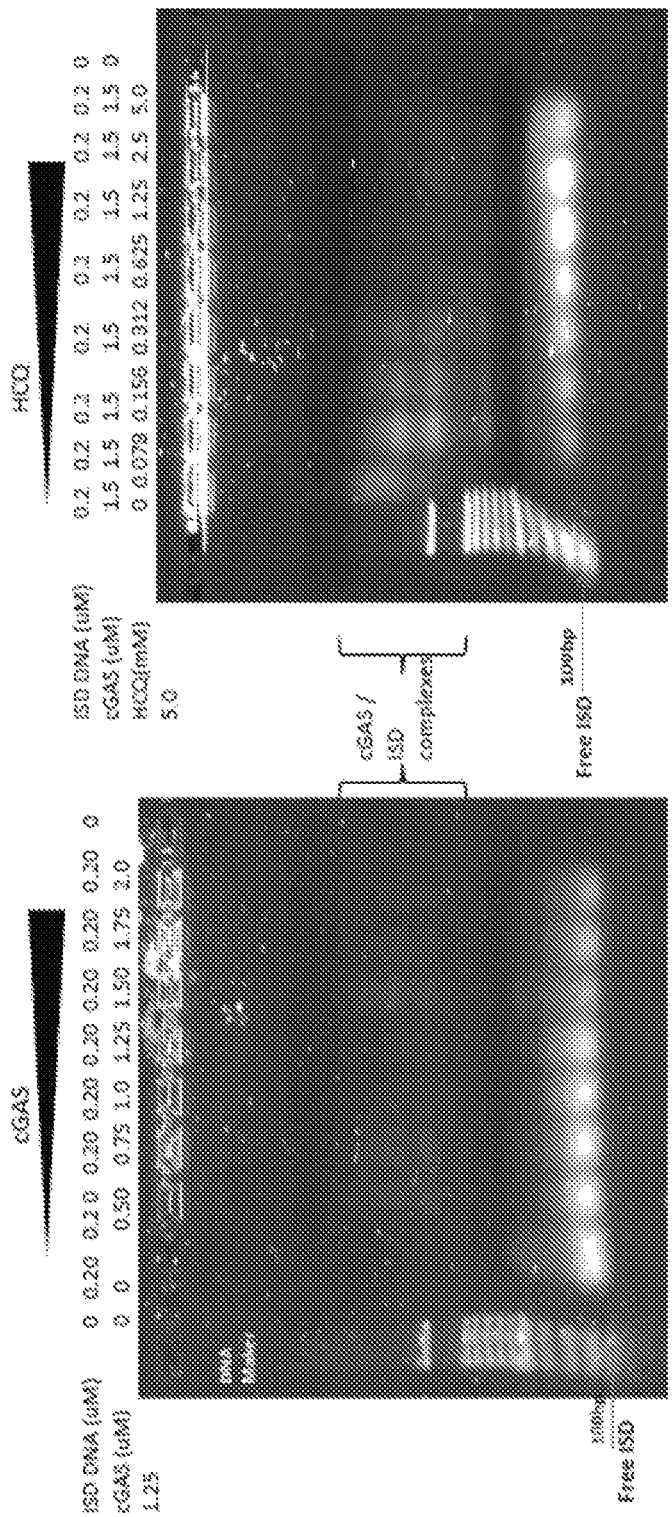
FIG. 1 is an electrophoretic mobility shift assay (EMSA) showing that HCQ blocks dsDNA/cGAS binding.

The present invention provides therapeutic strategies for treatment of severe debilitating diseases associated with IFN-I due to cGAS activation.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth.

In the broadest sense, as used herein, the term "autoimmune disease," refers to a disease wherein a patient's immune system is producing an unwanted immune response to one or more of their own proteins. Representative examples of autoimmune diseases include systemic lupus erythematosus (SLE), lupus nephritis (LN), rheumatoid arthritis, juvenile rheumatoid arthritis, Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, scleroderma, polymyositis and glomerulonephritis. Preferably, the autoimmune disease is SLE.

In the broadest sense, as used herein, the term "monogenic disorder," refers to a disease that is the result of a single defective gene on the autosomes. Representative monogenic disorders include rare monogenic disorders, Aicardi-Goutierre's Syndrome (AGS) and spondyloenchondrodysplasia (SPENCD). Preferably, the monogenic disorder is AGS.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal. particularly in a human, and includes: (a) preventing the disease from occurring in a subject which may be predisposed to the disease but has not yet been diagnosed as having it: (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets. Preferably, the subject herein is human.

The present invention relates to compounds of Formula (I) or a prodrug or metabolite thereof,

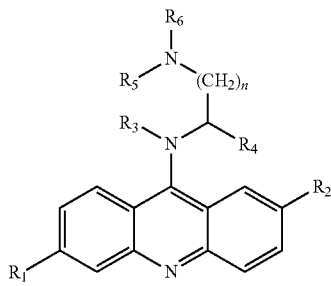
(I)

wherein
$R_1$ is —OH, —NH$_2$, —N(H)C(O)R$_7$ or —NO$_2$;
$R_2$ is —H or —OCH$_3$;
$R_3$ and $R_4$ are independently —H or —CH$_3$;
$R_5$ and $R_6$ are independently —H, —CH$_3$, —CH$_2$CH$_2$SH,

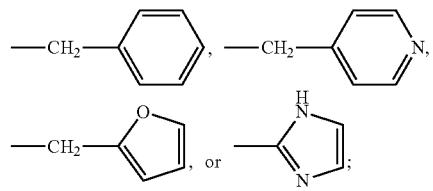

$R_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

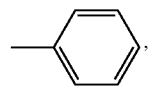

and
n is 2 or 3.
In some embodiments,
$R_1$ is —NH$_2$.
In some embodiments, $R_7$ is —NH$_2$ or —N(H)C(O)R$_7$;
$R_2$ is —OCH$_3$;
$R_3$ is —CH$_3$;
$R_4$ is —H;
$R_5$ is —CH$_3$;
$R_6$ is,

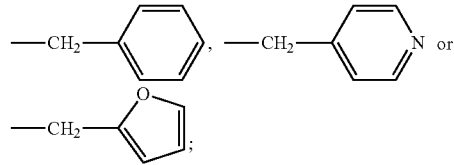

$R_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

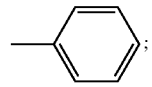

and
n is 2.
In some embodiments,
$R_1$ is —NH$_2$ or —N(H)C(O)R$_7$;
$R_2$ is —OCH$_3$;
$R_3$ is —CH$_3$;
$R_4$ is —H;
$R_5$ is —CH$_3$;
$R_6$ is,

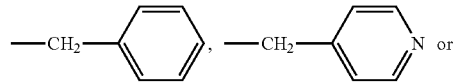

-continued

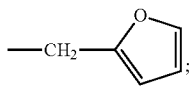

R₇ is —OCH₂CH₃, —CH₂CH₂CH₂CH₂CH₃, —CF₃ or

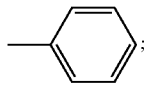

and
n is 2; and
In some embodiments,
R₁ is —NH₂;
R₂ is —OCH₃;
R₃ is —CH₃;
R₄ is —H;
R₅ is —CH₃;
R₆ is

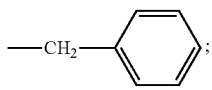

and
n is 2.
In some embodiments,
R₁ is —NH₂;
R₂ is —OCH₃;
R₃ is —CH₃;
R₄ is —H;
R₅ is —CH₃;
R₆ is

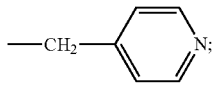

and n is 2.
In some embodiments,
R₁ is —NH₂;
R₂ is —OCH₃;
R₃ is —CH₃;
R₄ is —H;
R₅ is —CH₃;
R₆ is

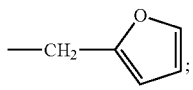

and
n is 2.
In some embodiments, R₁ is N(H)C(O)R₇.
In some embodiments,
R₁ is —N(H)C(O)R₇;
R₂ is —OCH₃;
R₃ is —CH₃;
R₄ is —H;
R₅ is —CH₃;
R₆ is

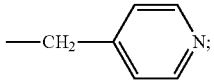

and
n is 2.
In some embodiments,
R₁ is —N(H)C(O)CH₂CH₂CH₂CH₂CH₃;
R₂ is —OCH₃;
R₃ is —CH₃;
R₄ is —H;
R₅ is —CH₃;
R₆ is

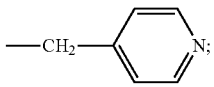

and
n is 2.
In some embodiments,
R₁ is —N(H)C(O)CF₃;
R₂ is —OCH₃;
R₃ is —CH₃;
R₄ is —H;
R₅ is —CH₃;
R₆ is

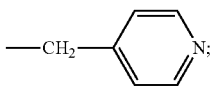

and
n is 2.
In some embodiments,
R₁ is —N(H)C(O)R₇;
R₂ is —OCH₃;
R₃ is —CH₃;
R₄ is —H;
R₅ is —CH₃;
R₆ is

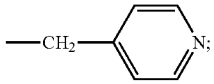

R₇ is

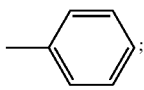

and
n is 2.
The present invention also relates to compounds of Formula (III) or a prodrug or metabolite thereof,

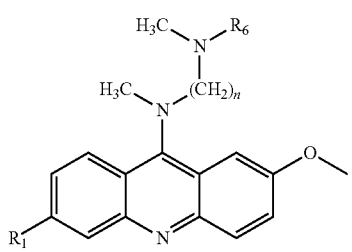

(III)

wherein R₁ is —Cl, —OH, —NH₂, or —NO₂; R₆ is

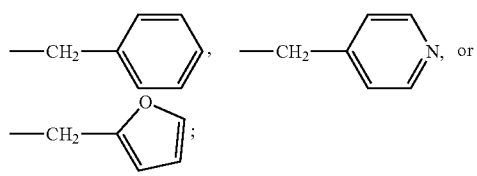

and n is 3 or 4.

In some aspects, R₁ is —Cl; R₆ is

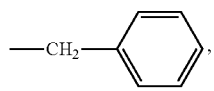

and n is 3.

In other aspects, R₁ is —Cl; R₆ is

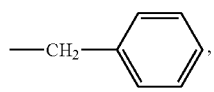

and n is 4.

In other aspects, R₁ is —Cl; R₆ is

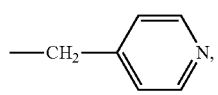

and n is 3.

In some aspects, R₁ is —Cl; R₆ is

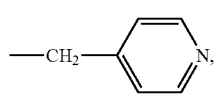

and n is 4.

In some aspects, R₁ is —Cl; R₆ is

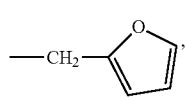

and n is 3.

In other aspects, R₁ is —Cl; R₆ is

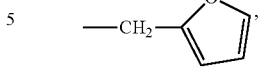

and n is 4.

In some aspects, R₁ is OH; R₆ is

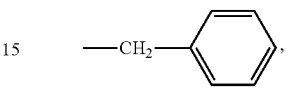

and n is 3.

In some aspects, R₁ is OH; R₆ is

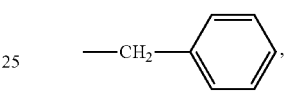

and n is 4.

In some aspects, R₁ is OH; R₆ is

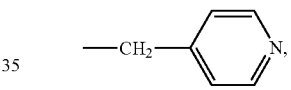

and n is 3.

In other aspects, R₁ is OH; R₆ is

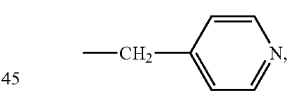

and n is 4.

In other aspects, R₁ is OH; R₆ is

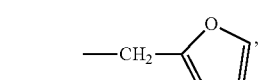

and n is 3.

In other aspects, R₁ is OH; R₆ is

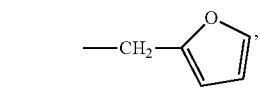

and n is 4.

In some aspects, $R_1$ is $NH_2$; $R_6$ is

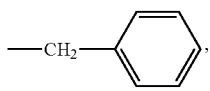

and n is 3.

In some aspects, $R_1$ is $NH_2$; $R_2$ is

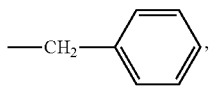

and n is 4.

In other aspects, $R_1$ is $NH_2$; $R_2$ is

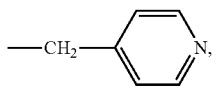

and n is 3.

In other aspects, $R_1$ is $NH_2$; $R_6$ is

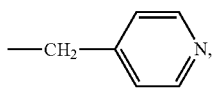

and n is 4.

In some aspects, $R_1$ is $NH_2$; $R_6$ is

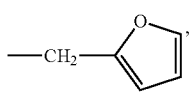

and n is 3.

In some aspects, $R_1$ is $NH_2$; $R_6$ is

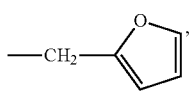

and n is 4.

In some aspects, $R_1$ is $NO_2$; $R_6$ is

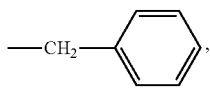

and n is 3.

In some aspects, $R_1$ is $NO_2$; $R_6$ is

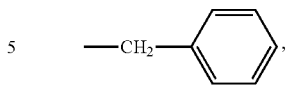

and n is 4.

In some aspects, $R_1$ is $NO_2$; $R_6$ is

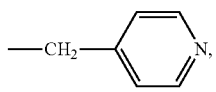

and n is 3.

In other aspects, $R_1$ is $NO_2$; $R_6$ is

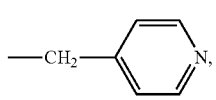

and n is 4.

In other aspects, $R_1$ is $NO_2$; $R_6$ is

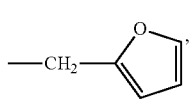

and n is 3.

In other aspects, $R_1$ is $NO_2$; $R_6$ is

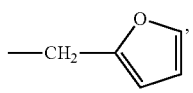

and n is 4.

Other aspects of the present invention relate to compounds of Formula (II) or a prodrug or metabolite thereof,

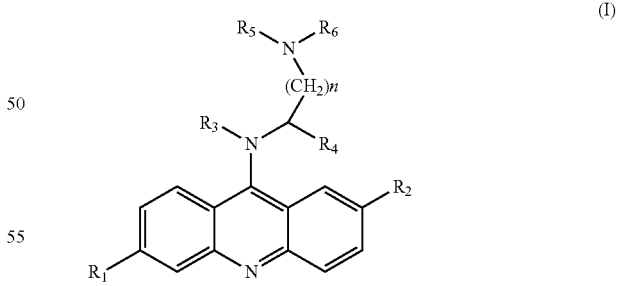

(I)

wherein $R_1$ is H, Cl, OH, $NH_2$ or $NO_2$; $R_2$ is H or —$OCH_3$; $R_3$ and $R_4$ are independently H or $CH_3$; $R_5$ and $R_6$ are independently H, $CH_3$, —$CH_2CH_2SH$,

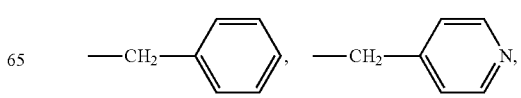

-continued

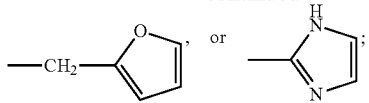

and n is 2 or 3.

In a preferred aspect, $R_1$ is $NH_2$; $R_2$ is —$OCH_3$; $R_3$ is $CH_3$; $R_4$ is H; $R_5$ is $CH_3$; $R_6$ is

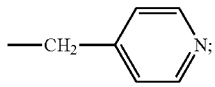

and n is 2.

In some aspects, $R_1$ is H, Cl, OH, $NH_2$ or $NO_2$, $R_2$ is H, $R_3$ and $R_4$ are H, $R_5$ and $R_6$ are H, and n is 2 or 3.

In some aspects, $R_1$ is H, Cl, OH, $NH_2$ or $NO_2$, $R_2$ is H, $R_3$ and $R_4$ are H, $R_5$ and $R_6$ are $CH_3$, and n is 2 or 3.

In some aspects, $R_1$ is H, Cl, OH, $NH_2$ or $NO_2$, $R_2$ is H, $R_3$ and $R_4$ are H, $R_5$ and $R_6$ are —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ and $R_6$ are

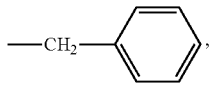

and n is 2 or 3.

In some aspects, $R_1$ is H, Cl, OH, $NH_2$ or $NO_2$, $R_2$ is H, $R_3$ and $R_4$ are H, $R_5$ and $R_6$ are

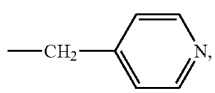

and n is 2 or 3.

In some aspects, $R_1$ is H, Cl, OH, $NH_2$ or $NO_2$, $R_2$ is H, $R_3$ and $R_4$ are H, $R_5$ and $R_6$ are

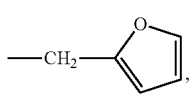

and n is 2 or 3.

In some aspects, $R_1$ is H, Cl, OH, $NH_2$ or $NO_2$, $R_2$ is H, $R_3$ and $R_4$ are H, $R_5$ and $R_6$ are

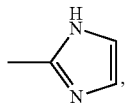

and n is 2 or 3.

In some aspects, $R_1$ is H, Cl, OH, $NH_2$ or $NO_2$, $R_2$ is H, $R_3$ and $R_4$ are H, $R_5$ is H, $R_6$ is $CH_3$, and n is 2.

In some aspects, $R_1$ is H, Cl, OH, $NH_2$ or $NO_2$, $R_2$ is H, $R_3$ and $R_4$ are H, $R_5$ is H, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

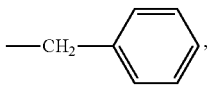

and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

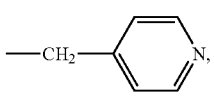

and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

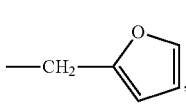

and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

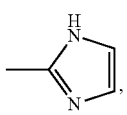

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is H, and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

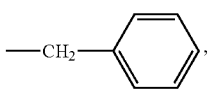

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

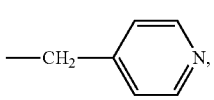

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

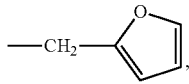

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

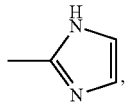

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is H, and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

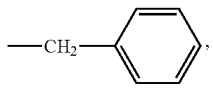

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

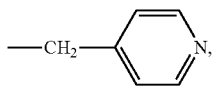

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

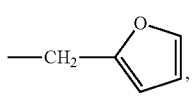

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

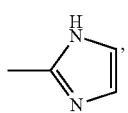

and n is 2 or 3.

In some aspects, $R_1$ is H, Cl, OH, $NH_2$ or $NO_2$, $R_2$ is H, $R_3$ and $R_4$ are H, $R_5$ is

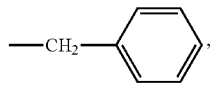

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is

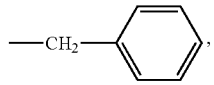

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

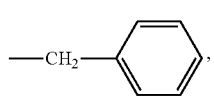

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is

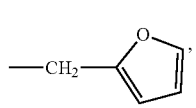

$R_6$ is

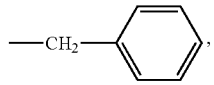

and n is 2 or 3.

In some aspects, $R_1$ is H, Cl, OH, $NH_2$ or $NO_2$, $R_2$ is H, $R_3$ and $R_4$ are H, $R_5$ is

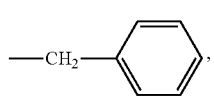

$R_6$ is

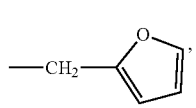

and n is 2 or 3.

In some aspects, $R_1$ is H, Cl, OH, $NH_2$ or $NO_2$, $R_2$ is H, $R_3$ and $R_4$ are H, $R_5$ is

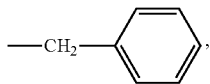

$R_6$ is

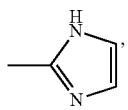

and n is 2 or 3.

In some aspects, $R_1$ is H, Cl, OH, $NH_2$ or $NO_2$, $R_2$ is H, $R_3$ and $R_4$ are H, $R_5$ is

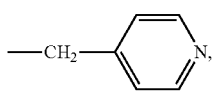

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is

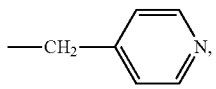

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

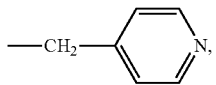

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is

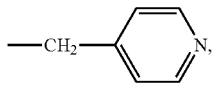

$R_6$ is

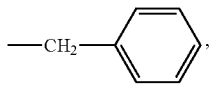

and n is 2 or 3.

In some aspects, $R_1$ is H, Cl, OH, $NH_2$ or $NO_2$, $R_2$ is H, $R_3$ and $R_4$ are H, $R_5$ is

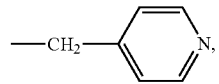

$R_6$ is

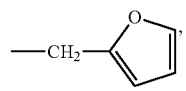

and n is 2 or 3.

In some aspects, $R_1$ is H, Cl, OH, $NH_2$ or $NO_2$, $R_2$ is H, $R_3$ and $R_4$ are H, $R_5$ is

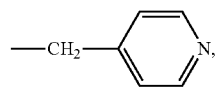

$R_6$ is

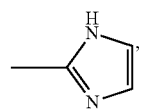

and n is 2 or 3.

In some aspects, $R_1$ is H, Cl, OH, $NH_2$ or $NO_2$, $R_2$ is H, $R_3$ and $R_4$ are H, $R_5$ is

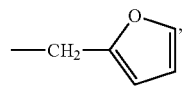

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is

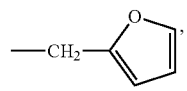

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

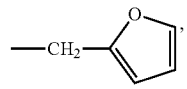

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is

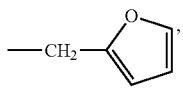

$R_6$ is

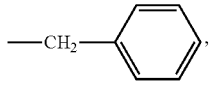

and n is 2 or 3.

In some aspects, $R_1$ is H, Cl, OH, $NH_2$ or $NO_2$, $R_2$ is H, $R_3$ and $R_4$ are H, $R_5$ is

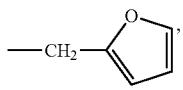

$R_6$ is

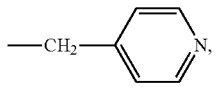

and n is 2 or 3.

In some aspects, $R_1$ is H, Cl, OH, $NH_2$ or $NO_2$, $R_2$ is H, $R_3$ and $R_4$ are H, $R_5$ is

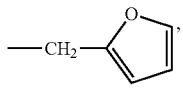

$R_6$ is

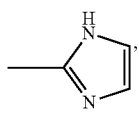

and n is 2 or 3.

In some aspects, $R_1$ is H, Cl, OH, $NH_2$ or $NO_2$, $R_2$ is H, $R_3$ and $R_4$ are H, $R_5$ is

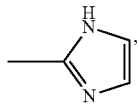

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is

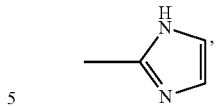

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

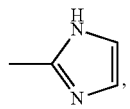

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is

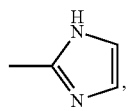

$R_6$ is

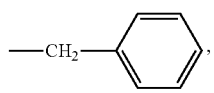

and n is 2 or 3.

In some aspects, $R_1$ is H, Cl, OH, $NH_2$ or $NO_2$, $R_2$ is H, $R_3$ and $R_4$ are H, $R_5$ is

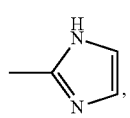

$R_6$ is

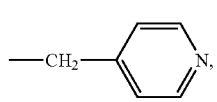

and n is 2 or 3.

In some aspects, $R_1$ is H, Cl, OH, $NH_2$ or $NO_2$, $R_2$ is H, $R_3$ and $R_4$ are H, $R_5$ is

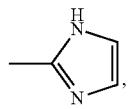

$R_6$ is

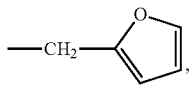

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is H, and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is H, and n is 2 or 3.

In some aspects, $R_1$ is H, Cl, OH, $NH_2$ or $NO_2$, $R_2$ is H, $R_3$ and $R_4$ are H, $R_5$ is

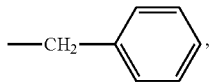

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is

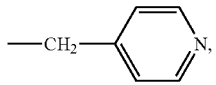

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is

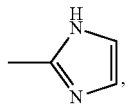

$R_6$ is H, and n is 2 or 3.

In some aspects, $R_1$ is H, Cl, OH, $NH_2$ or $NO_2$, $R_2$ is H, $R_3$ and $R_4$ are H, $R_5$ is H, $R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

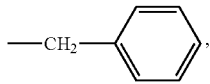

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

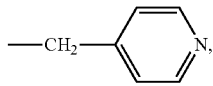

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

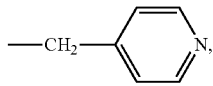

$R_6$ is $CH_3$, and n is 2 or 3.

In some aspects, $R_1$ is H, Cl, OH, $NH_2$ or $NO_2$, $R_2$ is H, $R_3$ and $R_4$ are H, $R_5$ is

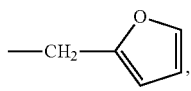

$R_6$ is $CH_3$, and n is 2 or 3.

In some aspects, $R_1$ is H, Cl, OH, $NH_2$ or $NO_2$, $R_2$ is H, R and $R_4$ are H, $R_5$ is H, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is

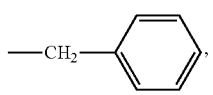

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is

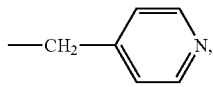

$R_6$ is —$CH_2CH_2SH$, and n is 2 or 3.

In some aspects, $R_1$ is H, $R_2$ is H, $R_3$ and $R_4$ are H, $R_5$ is

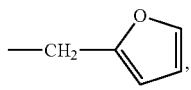

$R_6$ is —$CH_2CH_2SH$, and n is 2.

In some aspects, $R_1$ is H, Cl, OH, $NH_2$ or $NO_2$, $R_2$ is H, $R_3$ and $R_4$ are H, $R_5$ is

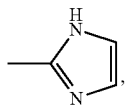

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

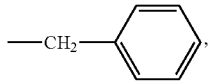

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

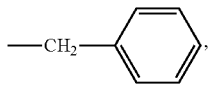

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

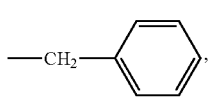

and n is 2 or 3.

In some aspects, $R_1$ is H, Cl, OH, $NH_2$ or $NO_2$, $R_2$ is H, $R_3$ and $R_4$ are H, $R_5$ is

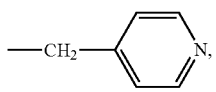

$R_6$ is

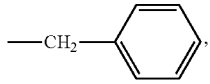

and n is 2 or 3.

In some aspects, $R_1$ is H, Cl, OH, $NH_2$ or $NO_2$, $R_2$ is H $R_3$ and $R_4$ are H, $R_5$ is

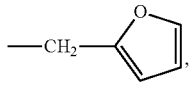

$R_6$ is

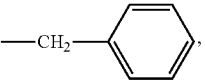

and n is 2 or 3.

In some aspects, $R_1$ is H, Cl, OH, $NH_2$ or $NO_2$, $R_2$ is H, $R_3$ and $R_4$ are H, $R_5$ is

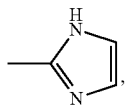

$R_6$ is

—$CH_2$—⟨phenyl⟩, and n is 2 or 3.

In some aspects, $R_1$ is H, Cl, OH, $NH_2$ or $NO_2$, $R_2$ is H, $R_3$ and $R_4$ are H, $R_5$ is H, $R_6$ is —$CH_2$—⟨pyridyl⟩, and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is —$CH_2$—⟨pyridyl⟩, and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is —$CH_2$—⟨pyridyl⟩, and n is 2 or 3.

In some aspects, $R_1$ is H, Cl, OH, $NH_2$ or $NO_2$, $R_2$ is H, $R_3$ and $R_4$ are H, $R_5$ is

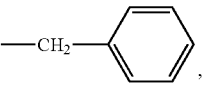

$R_6$ is

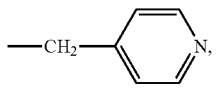

and n is 2 or 3.

In some aspects, $R_1$ is H, Cl, OH, $NH_2$ or $NO_2$, $R_2$ is H, $R_3$ and $R_4$ are H, $R_5$ is

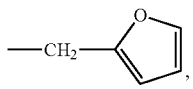

$R_6$ is

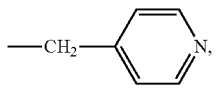

and n is 2 or 3.

In some aspects, $R_1$ is H, Cl, OH, $NH_2$ or $NO_2$, $R_2$ is H, $R_3$ and $R_4$ are H, $R_5$ is

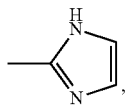

$R_6$ is

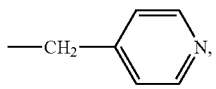

and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

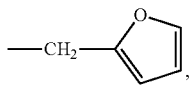

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

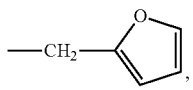

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

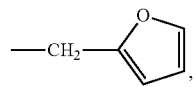

and n is 2 or 3.

In some aspects, $R_1$ is H, Cl, OH, $NH_2$ or $NO_2$, $R_2$ is H, $R_3$ and $R_4$ are H, $R_5$ is

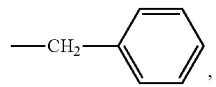

$R_6$ is

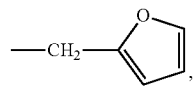

and n is 2 or 3.

In some aspects, $R_1$ is H, Cl, OH, $NH_2$ or $NO_2$, $R_2$ is H, $R_3$ and $R_4$ are H, $R_5$ is

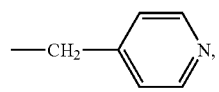

$R_6$ is

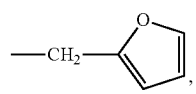

and n is 2 or 3.

In some aspects, $R_1$ is H, Cl, OH, $NH_2$ or $NO_2$, $R_2$ is H, $R_3$ and $R_4$ are H, $R_5$ is

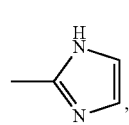

$R_6$ is

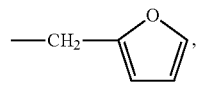

and n is 2 or 3.

In some aspects, $R_1$ is H, Cl, OH, $NH_2$ or $NO_2$, $R_2$ is H, $R_3$ and $R_4$ are H, $R_5$ is H, $R_6$ is

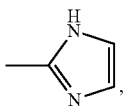

and n is 2 or 3.

In some aspects, $R_1$ is H, Cl, OH, $NH_2$ or $NO_2$, $R_2$ is H, $R_3$ and $R_4$ are H, $R_5$ is $CH_3$, $R_6$ is

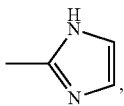

and n is 2 or 3.

In some aspects, $R_1$ is H, Cl, OH, $NH_2$ or $NO_2$, $R_2$ is H, $R_3$ and $R_4$ are H, $R_5$ is —$CH_2CH_2SH$, $R_6$ is

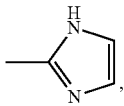

and n is 2 or 3.

In some aspects, $R_1$ is H, Cl, OH, $NH_2$ or $NO_2$, $R_2$ is H, $R_3$ and $R_4$ are H, $R_5$ is

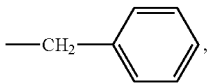

$R_6$ is

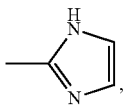

and n is 2 or 3.

In some aspects, $R_1$ is H, Cl, OH, $NH_2$ or $NO_2$, $R_2$ is H, $R_3$ and $R_4$ are H, $R_5$ is

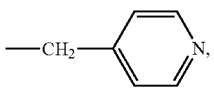

$R_6$ is

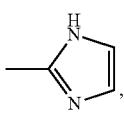

and n is 2 or 3.

In some aspects, $R_1$ is H, Cl, OH, $NH_2$ or $NO_2$, $R_2$ is H, $R_3$ and $R_4$ are H, $R_5$ is

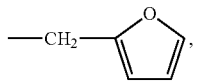

$R_6$ is

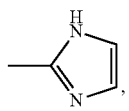

and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are H, and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are

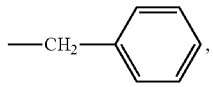

and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are

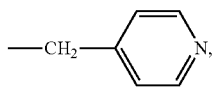

and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are

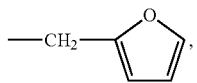

and n is 2 or 3.

In some aspects, $R_1$ is H, Cl, OH, $NH_2$ or $NO_2$, $R_2$ is H, $R_3$ and $R_4$ are $CH_3$, $R_5$ and $R_6$ are

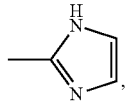

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

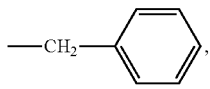

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

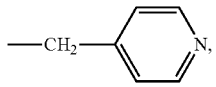

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

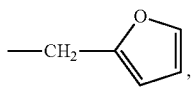

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

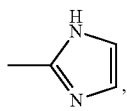

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

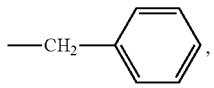

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

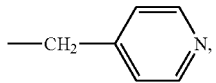

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

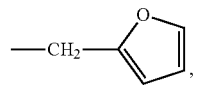

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

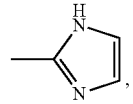

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

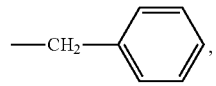

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

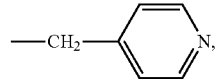

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

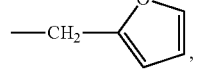

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

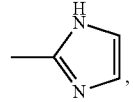

and n is 2 or 3.

In some aspects, $R_1$ is H, Cl, OH, $NH_2$ or $NO_2$, $R_2$ is H, $R_3$ and $R_4$ are $CH_3$, $R_5$ is

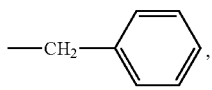

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

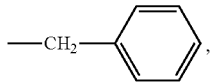

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

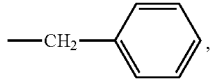

$R_6$ is $-CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

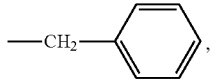

$R_6$ is

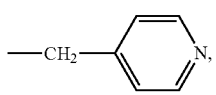

and n is 2 or 3.

In some aspects, $R_1$ is H, Cl, OH, $NH_2$ or $NO_2$, $R_2$ is H, $R_3$ and $R_4$ are $CH_3$, $R_5$ is

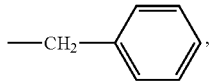

$R_6$ is

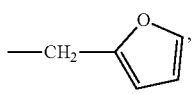

and n is 2 or 3.

In some aspects, $R_1$ is H, Cl, OH, $NH_2$ or $NO_2$, $R_2$ is H, $R_3$ and $R_4$ are $CH_3$, $R_5$ is

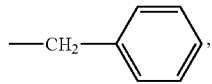

$R_6$ is

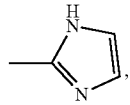

and n is 2 or 3.

In some aspects, $R_1$ is H, Cl, OH, $NH_2$ or $NO_2$, $R_2$ is H, $R_3$ and $R_4$ are $CH_3$, $R_5$ is

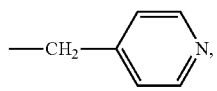

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

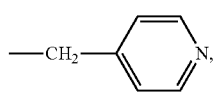

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

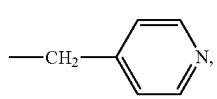

$R_6$ is $-CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

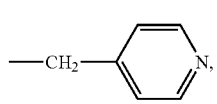

$R_6$ is

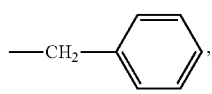

and n is 2 or 3.

In some aspects, $R_1$ is H, Cl, OH, $NH_2$ or $NO_2$, $R_2$ is H, $R_3$ and $R_4$ are $CH_3$, $R_5$ is

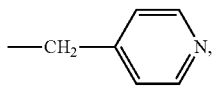

$R_6$ is

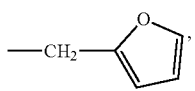

and n is 2 or 3.

In some aspects, $R_1$ is H, Cl, OH, $NH_2$ or $NO_2$, $R_2$ is H, $R_3$ and $R_4$ are $CH_3$, $R_5$ is

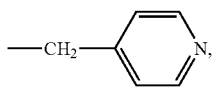

$R_6$ is

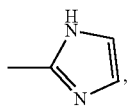

and n is 2 or 3.

In some aspects, $R_1$ is H, Cl, OH, $NH_2$ or $NO_2$, $R_2$ is H, $R_3$ and $R_4$ are $CH_3$, $R_5$ is

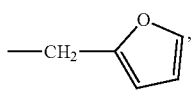

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

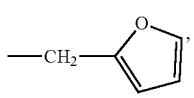

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

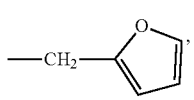

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

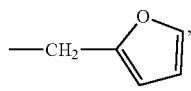

$R_6$ is

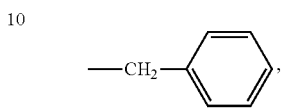

and n is 2 or 3.

In some aspects, $R_1$ is H, Cl, OH, $NH_2$ or $NO_2$, $R_2$ is H, $R_3$ and $R_4$ are $CH_3$, $R_5$ is

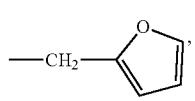

$R_6$ is

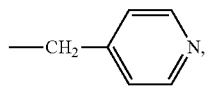

and n is 2 or 3.

In some aspects, $R_1$ is H, Cl, OH, $NH_2$ or $NO_2$, $R_2$ is H, $R_3$ and $R_4$ are $CH_3$, $R_5$ is

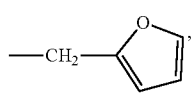

$R_6$ is

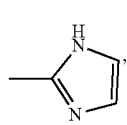

and n is 2 or 3.

In some aspects, $R_1$ is H, Cl, OH, $NH_2$ or $NO_2$, $R_2$ is H, $R_3$ and $R_4$ are $CH_3$, $R_5$ is

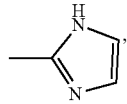

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

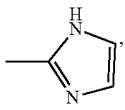

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

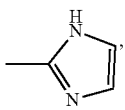

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

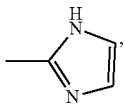

$R_6$ is

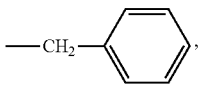

and n is 2 or 3.

In some aspects, $R_1$ is H, Cl, OH, $NH_2$ or $NO_2$, $R_2$ is H, $R_3$ and $R_4$ are $CH_3$, $R_5$ is

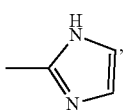

$R_6$ is

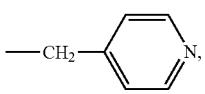

and n is 2 or 3.

In some aspects, $R_1$ is H, Cl, OH, $NH_2$ or $NO_2$, $R_2$ is H, $R_3$ and $R_4$ are $CH_3$, $R_5$ is

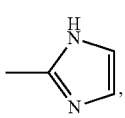

$R_6$ is

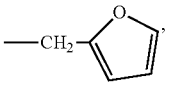

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

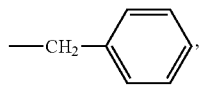

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

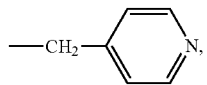

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

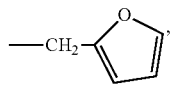

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is

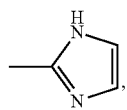

$R_6$ is H, and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

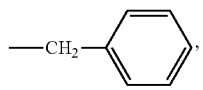

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

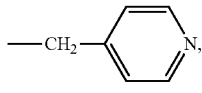

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

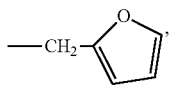

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is

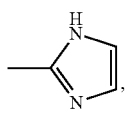

$R_6$ is $CH_3$, and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

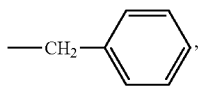

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

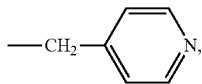

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

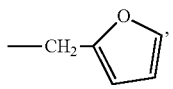

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is

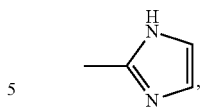

$R_6$ is —$CH_2CH_2SH$, and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

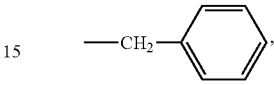

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

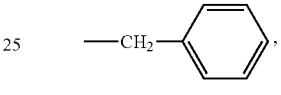

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

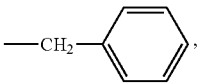

and n is 2 or 3.

In some aspects, $R_1$ is H, Cl, OH, $NH_2$ or $NO_2$, $R_2$ is H, $R_3$ and $R_4$ are $CH_3$, $R_5$ is

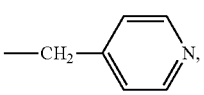

$R_6$ is

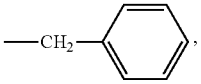

and n is 2 or 3.

In some aspects, $R_1$ is H, Cl, OH, $NH_2$ or $NO_2$, $R_2$ is H, $R_3$ and $R_4$ are $CH_3$, $R_5$ is

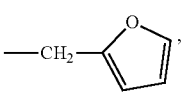

$R_6$ is

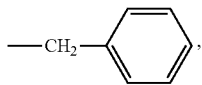

and n is 2 or 3.

In some aspects, $R_1$ is H, Cl, OH, $NH_2$ or $NO_2$, $R_2$ is H, $R_3$ and $R_4$ are $CH_3$, $R_5$ is

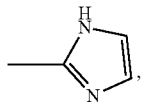

$R_6$ is

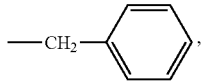

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

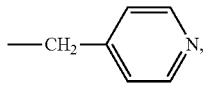

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

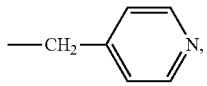

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

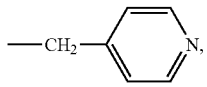

and n is 2 or 3.

In some aspects, $R_1$ is H, Cl, OH, $NH_2$ or $NO_2$, $R_2$ is H, $R_3$ and $R_4$ are $CH_3$, $R_5$ is

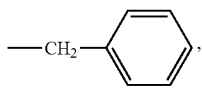

$R_6$ is

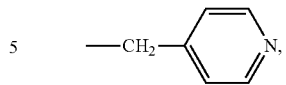

and n is 2 or 3.

In some aspects, $R_1$ is H, Cl, OH, $NH_2$ or $NO_2$, $R_2$ is H, $R_3$ and $R_4$ are $CH_3$, $R_5$ is

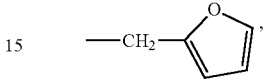

$R_6$ is

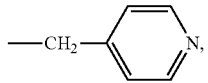

and n is 2 or 3.

In some aspects, $R_1$ is H, Cl, OH, $NH_2$ or $NO_2$, $R_2$ is H, $R_3$ and $R_4$ are $CH_3$, $R_5$ is

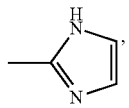

$R_6$ is

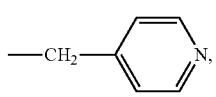

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

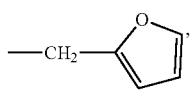

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

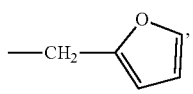

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

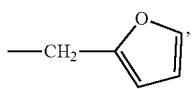

and n is 2 or 3.

In some aspects, $R_1$ is H, Cl, OH, $NH_2$ or $NO_2$, $R_2$ is H, $R_3$ and $R_4$ are $CH_3$, $R_5$ is

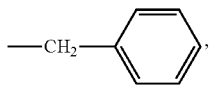

$R_6$ is

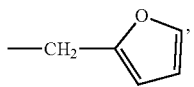

and n is 2 or 3.

In some aspects, $R_1$ is H, Cl, OH, $NH_2$ or $NO_2$, $R_2$ is H, $R_3$ and $R_4$ are $CH_3$, $R_5$ is

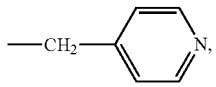

$R_6$ is

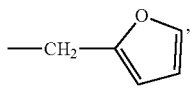

and n is 2 or 3.

In some aspects, $R_1$ is H, Cl, OH, $NH_2$ or $NO_2$, $R_2$ is H, $R_3$ and $R_4$ are $CH_3$, $R_5$ is

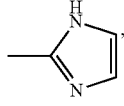

$R_6$ is

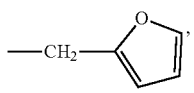

and n is 2 or 3.

In some aspects, $R_1$ is H, Cl, OH, $NH_2$ or $NO_2$, $R_2$ is H, $R_3$ and $R_4$ are $CH_3$, $R_5$ is H, $R_6$ is

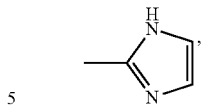

and n is 2 or 3.

In some aspects, $R_1$ is H, Cl, OH, $NH_2$ or $NO_2$, $R_2$ is H, $R_3$ and $R_4$ are $CH_3$, $R_5$ is $CH_3$, $R_6$ is

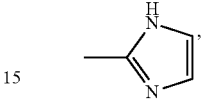

and n is 2 or 3.

In some aspects, $R_1$ is H, Cl, OH, $NH_2$ or $NO_2$, $R_2$ is H, $R_3$ and $R_4$ are $CH_3$, $R_5$ is —$CH_2CH_2SH$, $R_6$ is

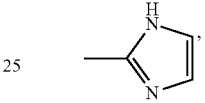

and n is 2 or 3.

In some aspects, $R_1$ is H, Cl, OH, $NH_2$ or $NO_2$, $R_2$ is H, $R_3$ and $R_4$ are $CH_3$, $R_5$ is

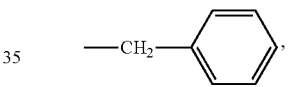

$R_6$ is

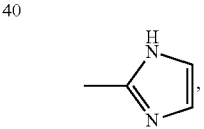

and n is 2 or 3.

In some aspects, $R_1$ is H, Cl, OH, $NH_2$ or $NO_2$, $R_2$ is H, $R_3$ and $R_4$ are $CH_3$, $R_5$ is

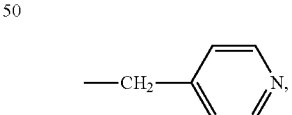

$R_6$ is

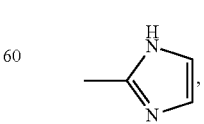

and n is 2 or 3.

In some aspects, $R_1$ is H, Cl, OH, $NH_2$ or $NO_2$, $R_2$ is H, $R_3$ and $R_4$ are $CH_3$, $R_5$ is

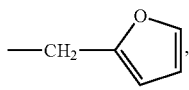

$R_6$ is

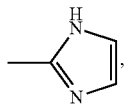

and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are H, and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are $CH_3$, and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are $-CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are

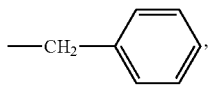

and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are

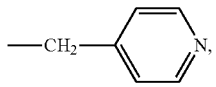

and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are

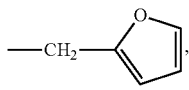

and n is 2 or 3.

In some aspects, $R_1$ is H, Cl, OH, $NH_2$ or $NO_2$, $R_2$ is H, $R_3$ is H, $R_4$ is $CH_3$, $R_5$ and $R_6$ are

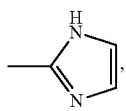

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is $CH_3$, and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is $-CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

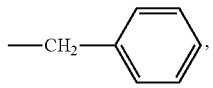

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

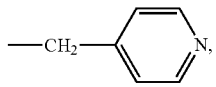

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

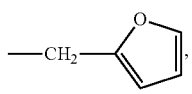

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

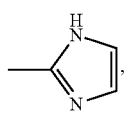

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is H, and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is $-CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

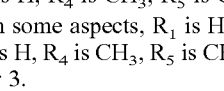

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

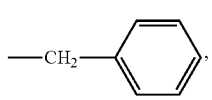

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

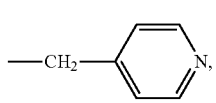

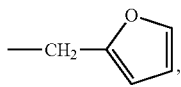

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

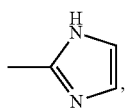

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is H, and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

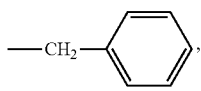

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

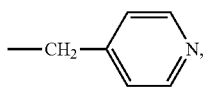

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

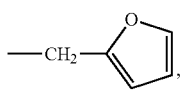

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

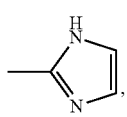

and n is 2 or 3.

In some aspects, $R_1$ is H, Cl, OH, $NH_2$ or $NO_2$, $R_2$ is H, $R_3$ is H, $R_4$ is $CH_3$, $R_5$ is

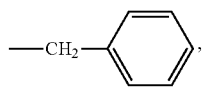

$R_6$ is H, and n is 2 or 3.

In some aspects, $R_1$ is H, Cl, OH, $NH_2$ or $NO_2$, $R_2$ is H, $R_3$ is H, $R_4$ is $CH_3$, $R_5$ is

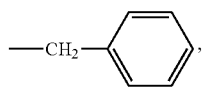

$R_6$ is $CH_3$, and n is 2 or 3.

In some aspects, $R_1$ is H, Cl, OH, $NH_2$ or $NO_2$, $R_2$ is H, $R_3$ is H, $R_4$ is $CH_3$, $R_5$ is

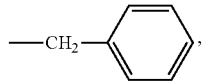

$R_6$ is —$CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ is

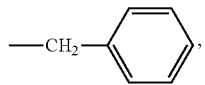

$R_6$ is

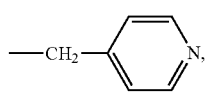

and n is 2 or 3.

In some aspects, $R_1$ is H, Cl, OH, $NH_2$ or $NO_2$, $R_2$ is H, $R_3$ is H, $R_4$ is $CH_3$, $R_5$ is

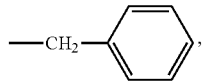

$R_6$ is

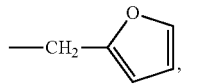

and n is 2 or 3.

In some aspects, $R_1$ is H, Cl, OH, $NH_2$ or $NO_2$, $R_2$ is H, $R_3$ is H, $R_4$ is $CH_3$, $R_5$ is

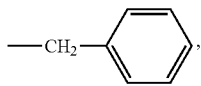

$R_6$ is

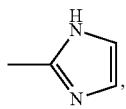

and n is 2 or 3.

In some aspects, $R_1$ is H, Cl, OH, $NH_2$ or $NO_2$, $R_2$ is H, $R_3$ is H, $R_4$ is $CH_3$, $R_5$ is

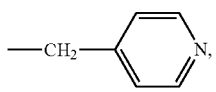

$R_6$ is H, and n is 2 or 3.

In some aspects, $R_1$ is H, Cl, OH, $NH_2$ or $NO_2$, $R_2$ is H, $R_3$ is H, $R_4$ is $CH_3$, $R_5$ is

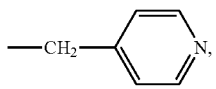

$R_6$ is $CH_3$, and n is 2 or 3.

In some aspects, $R_1$ is H, Cl, OH, $NH_2$ or $NO_2$, $R_2$ is H, $R_3$ is H, $R_4$ is $CH_3$, $R_5$ is

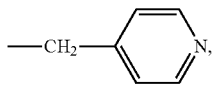

$R_6$ is —$CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ is

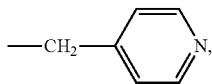

$R_6$ is

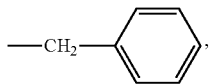

and n is 2 or 3.

In some aspects, $R_1$ is H, Cl, OH, $NH_2$ or $NO_2$, $R_2$ is H, $R_3$ is H, $R_4$ is $CH_3$, $R_5$ is

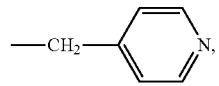

$R_6$ is

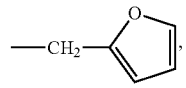

and n is 2 or 3.

In some aspects, $R_1$ is H, Cl, OH, $NH_2$ or $NO_2$, $R_2$ is H, $R_3$ is H, $R_4$ is $CH_3$, $R_5$ is

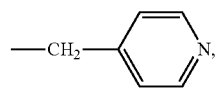

$R_6$ is

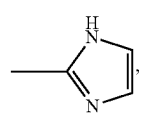

and n is 2 or 3.

In some aspects, $R_1$ is H, Cl, OH, $NH_2$ or $NO_2$, $R_2$ is H, $R_3$ is H, $R_4$ is $CH_3$, $R_5$ is

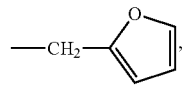

$R_6$ is H, and n is 2 or 3.

In some aspects, $R_1$ is H, Cl, OH, $NH_2$ or $NO_2$, $R_2$ is H, $R_3$ is H, $R_4$ is $CH_3$, $R_5$ is

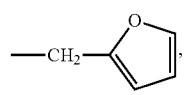

$R_6$ is $CH_3$, and n is 2 or 3.

In some aspects, $R_1$ is H, Cl, OH, $NH_2$ or $NO_2$, $R_2$ is H, $R_3$ is H, $R_4$ is $CH_3$, $R_5$ is

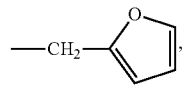

$R_6$ is —$CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ is

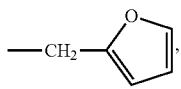

R$_6$ is

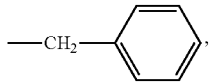

and n is 2 or 3.

In some aspects, R$_1$ is H, Cl, OH, NH$_2$ or NO$_2$, R$_2$ is H, R$_3$ is H, R$_4$ is CH$_3$, R$_5$ is

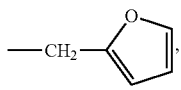

R$_6$ is

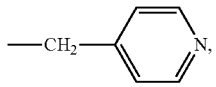

and n is 2 or 3.

In some aspects, R$_1$ is H, Cl, OH, NH$_2$ or NO$_2$, R$_2$ is H, R$_3$ is H, R$_4$ is CH$_3$, R$_5$ is

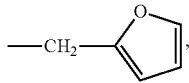

R$_6$ is

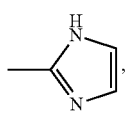

and n is 2 or 3.

In some aspects, R$_1$ is H, Cl, OH, NH$_2$ or NO$_2$, R$_2$ is H, R$_3$ is H, R$_4$ is CH$_3$, R$_5$ is

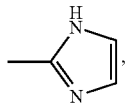

R$_6$ is H, and n is 2 or 3.

In some aspects, R$_1$ is H, Cl, OH, NH$_2$ or NO$_2$, R$_2$ is H, R$_3$ is H, R$_4$ is CH$_3$, R$_5$ is

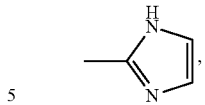

R$_6$ is CH$_3$, and n is 2 or 3.

In some aspects, R$_1$ is H, Cl, OH, NH$_2$ or NO$_2$, R$_2$ is H, R$_3$ is H, R$_4$ is CH$_3$, R$_5$ is

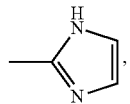

R$_6$ is —CH$_2$CH$_2$SH, and n is 2 or 3.

In some aspects, R$_1$ is H, Cl, OH, NH$_2$ or NO$_2$, R$_2$ is H, R$_3$ is H, R$_4$ is CH$_3$, R$_5$ is

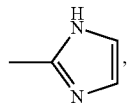

R$_6$ is

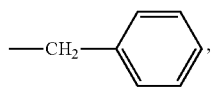

and n is 2 or 3.

In some aspects, R$_1$ is H, Cl, OH, NH$_2$ or NO$_2$, R$_2$ is H, R$_3$ is H, R$_4$ is CH$_3$, R$_5$ is

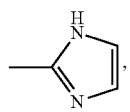

R$_6$ is

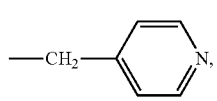

and n is 2 or 3.

In some aspects, R$_1$ is H, Cl, OH, NH$_2$ or NO$_2$, R$_2$ is H, R$_3$ is H, R$_4$ is CH$_3$, R$_5$ is

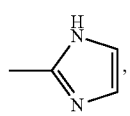

$R_6$ is

—CH$_2$—[furan], and n is 2 or 3.

In some aspects, $R_1$ is H, Cl, OH, NH$_2$ or NO$_2$, $R_2$ is H, $R_3$ is H, $R_4$ is CH$_3$, $R_5$ is CH$_3$, $R_6$ is H, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$CH$_2$SH, $R_6$ is H, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[phenyl], $R_6$ is H, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[pyridyl], $R_6$ is H, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[furan], $R_6$ is H, and n is 2 or 3.

In some aspects, $R_1$ is H, Cl, OH, NH$_2$ or NO$_2$, $R_2$ is H, $R_3$ is H, $R_4$ is CH$_3$, $R_5$ is

[imidazole], $R_6$ is H, and n is 2 or 3.

In some aspects, $R_1$ is H, Cl, OH, NH$_2$ or NO$_2$, $R_2$ is H, $R_3$ is H, $R_4$ is CH$_3$, $R_5$ is H, $R_6$ is CH$_3$, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$CH$_2$SH, $R_6$ is CH$_3$, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[phenyl], $R_6$ is CH$_3$, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[pyridyl], $R_6$ is CH$_3$, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[furan], $R_6$ is CH$_3$, and n is 2 or 3.

In some aspects, $R_1$ is H, Cl, OH, NH$_2$ or NO$_2$, $R_2$ is H, $R_3$ is H, $R_4$ is CH$_3$, $R_5$ is

[imidazole], $R_6$ is CH$_3$, and n is 2 or 3.

In some aspects, $R_1$ is H, Cl, OH, NH$_2$ or NO$_2$, $R_2$ is H, $R_3$ is H, $R_4$ is CH$_3$, $R_5$ is H, $R_6$ is —CH$_2$CH$_2$SH, and n is 2 or 3.

In some aspects, $R_1$ is H, Cl, OH, NH$_2$ or NO$_2$, $R_2$ is H, $R_3$ is H, $R_4$ is CH$_3$, $R_5$ is CH$_3$, $R_6$ is —CH$_2$CH$_2$SH, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[phenyl], $R_6$ is —CH$_2$CH$_2$SH, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[pyridyl], $R_6$ is —CH$_2$CH$_2$SH, and n is 2 or 3.

In some aspects, $R_1$ is H, Cl, OH, NH$_2$ or NO$_2$, $R_2$ is H, $R_3$ is H, $R_4$ is CH$_3$, $R_5$ is —CH$_2$—[furan], $R_6$ is —CH$_2$CH$_2$SH, and n is 2 or 3.

In some aspects, $R_1$ is H, Cl, OH, NH$_2$ or NO$_2$, $R_2$ is H, $R_3$ is H, $R_4$ is CH$_3$, $R_5$ is

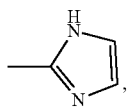

$R_6$ is —$CH_2CH_2SH$, and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

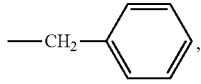

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

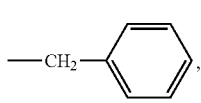

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

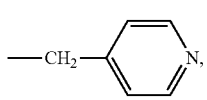

and n is 2 or 3.

In some aspects, $R_1$ is H, Cl, OH, $NH_2$ or $NO_2$, $R_2$ is H, $R_3$ is H, $R_4$ is $CH_3$, $R_5$ is

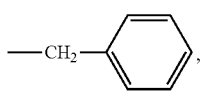

$R_6$ is

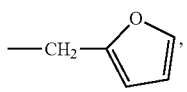

and n is 2 or 3.

In some aspects, $R_1$ is H, Cl, OH, $NH_2$ or $NO_2$, $R_3$ is H, $R_4$ is $CH_3$, $R_5$ is $R_6$ is

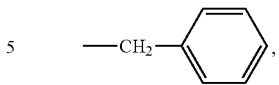

and n is 2 or 3.

In some aspects, $R_1$ is H, Cl, OH, $NH_2$ or $NO_2$, $R_2$ is H, $R_3$ is H, $R_4$ is $CH_3$, $R_5$ is

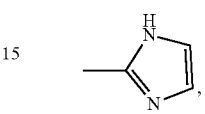

$R_6$ is

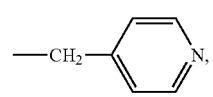

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

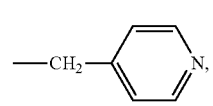

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

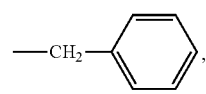

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

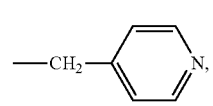

and n is 2 or 3.

In some aspects, $R_1$ is H, Cl, OH, $NH_2$ or $NO_2$, $R_2$ is H, $R_3$ is H, $R_4$ is $CH_3$, $R_5$ is

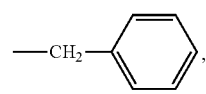

$R_6$ is

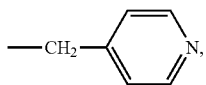

and n is 2 or 3.

In some aspects, $R_1$ is H, Cl, OH, $NH_2$ or $NO_2$, $R_2$ is H, $R_3$ is H, $R_4$ is $CH_3$, $R_5$ is

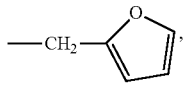

$R_6$ is

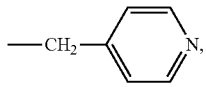

and n is 2 or 3.

In some aspects, $R_1$ is H, Cl, OH, $NH_2$ or $NO_2$, $R_2$ is H, $R_3$ is H, $R_4$ is $CH_3$, $R_5$ is

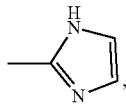

$R_6$ is

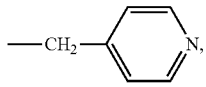

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

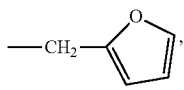

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

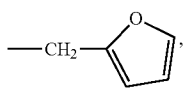

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

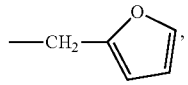

and n is 2 or 3.

In some aspects, $R_1$ is H, Cl, OH, $NH_2$ or $NO_2$, $R_2$ is H, $R_3$ is H, $R_4$ is $CH_3$, $R_5$ is

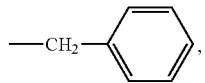

$R_6$ is

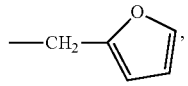

and n is 2 or 3.

In some aspects, $R_1$ is H, Cl, OH, $NH_2$ or $NO_2$, $R_2$ is H, $R_3$ is H, $R_4$ is $CH_3$, $R_5$ is

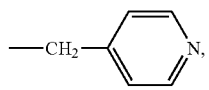

$R_6$ is

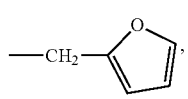

and n is 2 or 3.

In some aspects, $R_1$ is H, Cl, OH, $NH_2$ or $NO_2$, $R_2$ is H, $R_3$ is H, $R_4$ is $CH_3$, $R_5$ is

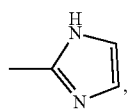

$R_6$ is

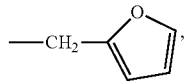

and n is 2 or 3.

In some aspects, $R_1$ is H, Cl, OH, $NH_2$ or $NO_2$, $R_2$ is H, $R_3$ is H, $R_4$ is $CH_3$, $R_5$ is H, $R_6$ is

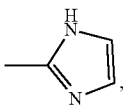

and n is 2 or 3.

In some aspects, $R_1$ is H, Cl, OH, $NH_2$ or $NO_2$, $R_2$ is H, $R_3$ is H, $R_4$ is $CH_3$, $R_5$ is $CH_3$, $R_6$ is

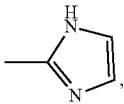

and n is 2 or 3.

In some aspects, $R_1$ is H, Cl, OH, $NH_2$ or $NO_2$, $R_2$ is H, $R_3$ is H, $R_4$ is $CH_3$, $R_5$ is —$CH_2CH_2SH$, $R_6$ is

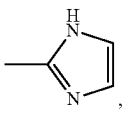

and n is 2 or 3.

In some aspects, $R_1$ is H, Cl, OH, $NH_2$ or $NO_2$, $R_2$ is H, $R_3$ is H, $R_4$ is $CH_3$, $R_5$ is

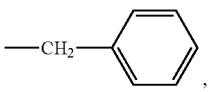

$R_6$ is

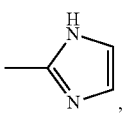

and n is 2 or 3.

In some aspects, $R_1$ is H, Cl, OH, $NH_2$ or $NO_2$, $R_2$ is H, $R_3$ is H, $R_4$ is $CH_3$, $R_5$ is

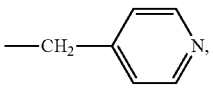

$R_6$ is

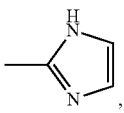

and n is 2 or 3.

In some aspects, $R_1$ is H, Cl, OH, $NH_2$ or $NO_2$, $R_2$ is H, $R_3$ is H, $R_4$ is $CH_3$, $R_5$ is

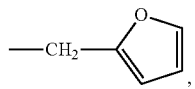

$R_6$ is

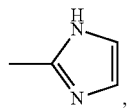

and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are H, and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are

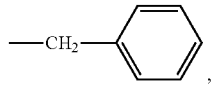

and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are

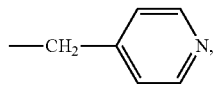

and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are

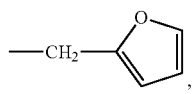

and n is 2 or 3.

In some aspects, $R_1$ is H, Cl, OH, $NH_2$ or $NO_2$, $R_2$ is H, $R_3$ is $CH_3$, $R_4$ is H, $R_5$ and $R_6$ are

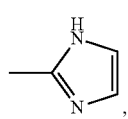

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

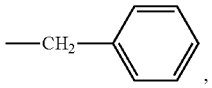

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

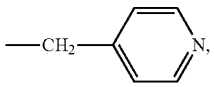

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

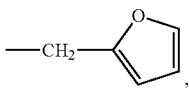

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

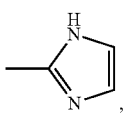

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

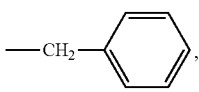

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

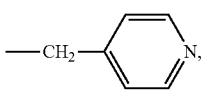

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

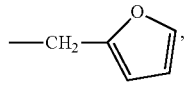

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

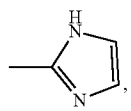

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

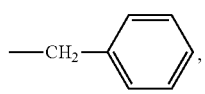

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

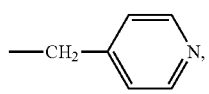

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

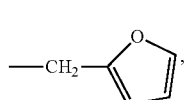

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

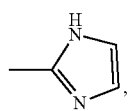

and n is 2 or 3.

In some aspects, $R_1$ is H, Cl, OH, $NH_2$ or $NO_2$, $R_2$ is H, $R_3$ is $CH_3$, $R_4$ is H, $R_5$ is

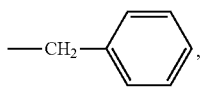

$R_6$ is H and n is 2 or 3.

In some aspects, $R_1$ is H, Cl, OH, $NH_2$ or $NO_2$, $R_2$ is H, $R_3$ is $CH_3$, $R_4$ is H, $R_5$ is

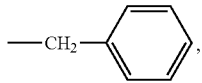

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

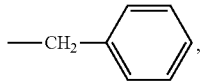

$R_6$ is $-CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

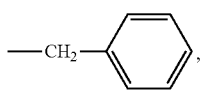

$R_6$ is

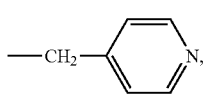

and n is 2 or 3.

In some aspects, $R_1$ is H, Cl, OH, $NH_2$ or $NO_2$, $R_2$ is H, $R_3$ is $CH_3$, $R_4$ is H, $R_5$ is

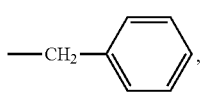

$R_6$ is

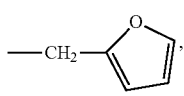

and n is 2 or 3.

In some aspects, $R_1$ is H, Cl, OH, $NH_2$ or $NO_2$, $R_3$ is $CH_3$, $R_4$ is H, $R_5$ is

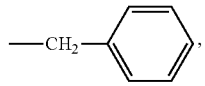

$R_6$ is

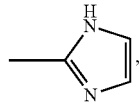

and n is 2 or 3.

In some aspects, $R_1$ is H, Cl, OH, $NH_2$ or $NO_2$, $R_2$ is H, $R_3$ is $CH_3$, $R_4$ is H, $R_5$ is

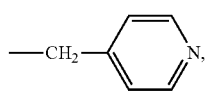

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

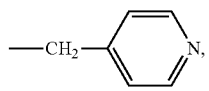

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

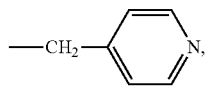

$R_6$ is $-CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

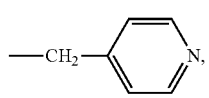

$R_6$ is

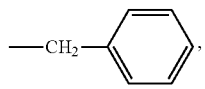

and n is 2 or 3.

In some aspects, $R_1$ is H, Cl, OH, $NH_2$ or $NO_2$, $R_2$ is H, $R_3$ is $CH_3$, $R_4$ is H, $R_5$ is

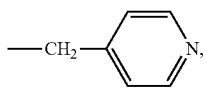

$R_6$ is

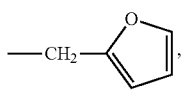

and n is 2 or 3.

In some aspects, $R_1$ is H, Cl, OH, $NH_2$ or $NO_2$, $R_2$ is H, $R_3$ is $CH_3$, $R_4$ is H, $R_5$ is

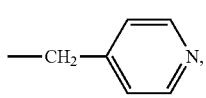

$R_6$ is

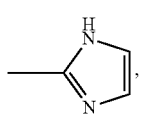

and n is 2 or 3.

In some aspects, $R_1$ is H, Cl, OH, $NH_2$ or $NO_2$, $R_2$ is H, $R_3$ is $CH_3$, $R_4$ is H, $R_5$ is

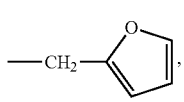

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

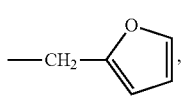

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

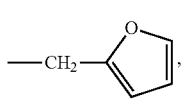

$R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

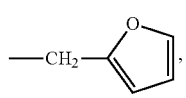

$R_6$ is

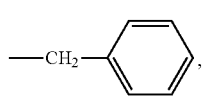

and n is 2 or 3.

In some aspects, $R_1$ is H, Cl, OH, $NH_2$ or $NO_2$, $R_2$ is H, $R_3$ is $CH_3$, $R_4$ is H, $R_5$ is

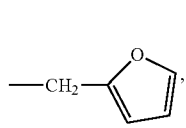

$R_6$ is

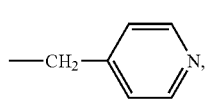

and n is 2 or 3.

In some aspects, $R_1$ is H, Cl, OH, $NH_2$ or $NO_2$, $R_3$ is $CH_3$, $R_4$ is H, $R_5$ is

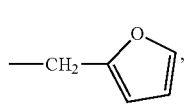

$R_6$ is

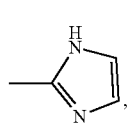

and n is 2 or 3.

In some aspects, $R_1$ is H, Cl, OH, $NH_2$ or $NO_2$, $R_2$ is H, $R_3$ is $CH_3$, $R_4$ is H, $R_5$ is

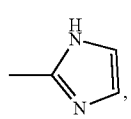

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

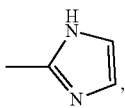

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

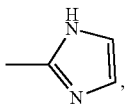

$R_6$ is $-CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

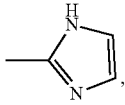

$R_6$ is

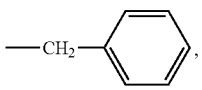

and n is 2 or 3.

In some aspects, $R_1$ is H, Cl, OH, $NH_2$ or $NO_2$, $R_2$ is H, $R_3$ is $CH_3$, $R_4$ is H, $R_5$ is

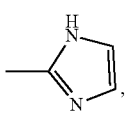

$R_6$ is

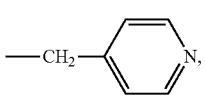

and n is 2 or 3.

In some aspects, $R_1$ is H, Cl, OH, $NH_2$ or $NO_2$, $R_2$ is H, $R_3$ is $CH_3$, $R_4$ is H, $R_5$ is

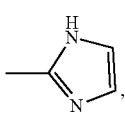

$R_6$ is

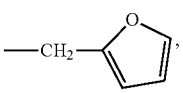

and n is 2 or 3.

In some aspects, $R_1$ is H, Cl, OH, $NH_2$ or $NO_2$, $R_3$ is $CH_3$, $R_4$ is H, $R_5$ is $CH_3$, $R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is $-CH_2CH_2SH$, $R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

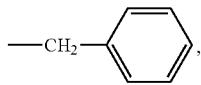

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

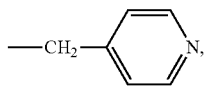

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

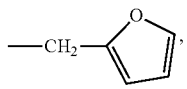

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is

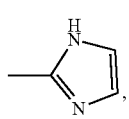

$R_6$ is H, and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is $-CH_2CH_2SH$, $R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

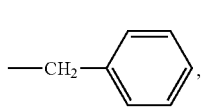

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

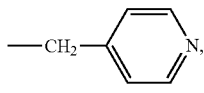

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

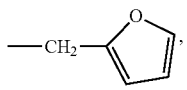

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

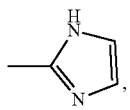

$R_6$ is $CH_3$, and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

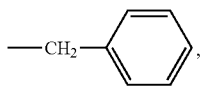

$R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

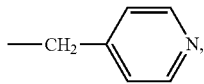

$R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

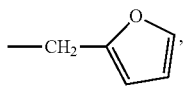

$R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is

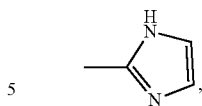

$R_6$ is —$CH_2CH_2SH$, and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

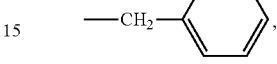

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

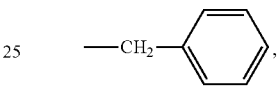

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

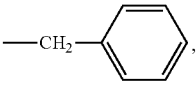

and n is 2 or 3.

In some aspects, $R_1$ is H, Cl, OH, $NH_2$ or $NO_2$, $R_2$ is H, $R_3$ is $CH_3$, $R_4$ is H, $R_5$ is

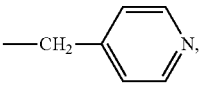

$R_6$ is

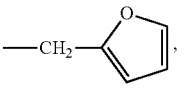

and n is 2 or 3.

In some aspects, $R_1$ is H, Cl, OH, $NH_2$ or $NO_2$, $R_2$ is H, $R_3$ is $CH_3$, $R_4$ is H, $R_5$ is

$R_6$ is

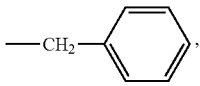

and n is 2 or 3.

In some aspects, $R_1$ is H, Cl, OH, $NH_2$ or $NO_2$, $R_2$ is H, $R_3$ is $CH_3$, $R_4$ is H, $R_5$ is

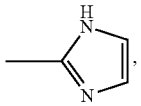

$R_6$ is

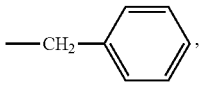

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

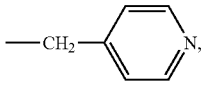

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

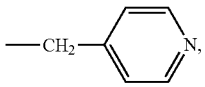

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

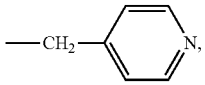

and n is 2 or 3.

In some aspects, $R_1$ is H, Cl, OH, $NH_2$ or $NO_2$, $R_2$ is H, $R_3$ is $CH_3$, $R_4$ is H, $R_5$ is

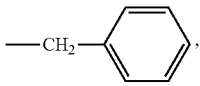

$R_6$ is

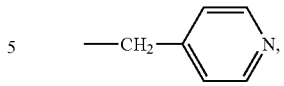

and n is 2 or 3.

In some aspects, $R_1$ is H, Cl, OH, $NH_2$ or $NO_2$, $R_2$ is H, $R_3$ is $CH_3$, $R_4$ is H, $R_5$ is

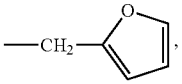

$R_6$ is

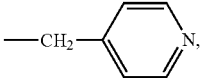

and n is 2 or 3.

In some aspects, $R_1$ is H, Cl, OH, $NH_2$ or $NO_2$, $R_2$ is H, $R_3$ is $CH_3$, $R_4$ is H, $R_5$ is

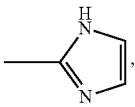

$R_6$ is

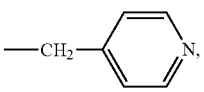

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

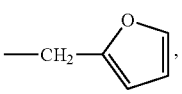

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

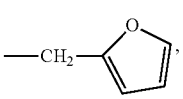

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

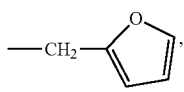

and n is 2 or 3.

In some aspects, $R_1$ is H, Cl, OH, $NH_2$ or $NO_2$, $R_2$ is H, $R_3$ is $CH_3$, $R_4$ is H, $R_5$ is

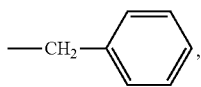

$R_6$ is

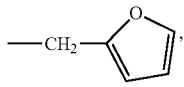

and n is 2 or 3.

In some aspects, $R_1$ is H, Cl, OH, $NH_2$ or $NO_2$, $R_2$ is H, $R_3$ is $CH_3$, $R_4$ is H, $R_5$ is

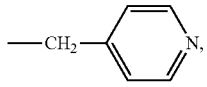

$R_6$ is

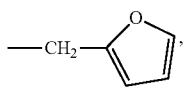

and n is 2 or 3.

In some aspects, $R_1$ is H, Cl, OH, $NH_2$ or $NO_2$, $R_2$ is H, $R_3$ is $CH_3$, $R_4$ is H, $R_5$ is

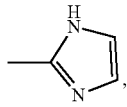

$R_6$ is

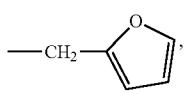

and n is 2 or 3.

In some aspects, $R_1$ is H, Cl, OH, $NH_2$ or $NO_2$, $R_2$ is H, $R_3$ is $CH_3$, $R_4$ is H, $R_5$ is H, $R_6$ is

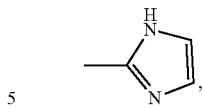

and n is 2 or 3.

In some aspects, $R_1$ is H, Cl, OH, $NH_2$ or $NO_2$, $R_2$ is H, $R_3$ is $CH_3$, $R_4$ is H, $R_5$ is $CH_3$, $R_6$ is

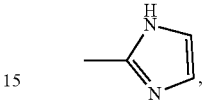

and n is 2 or 3.

In some aspects, $R_1$ is H, Cl, OH, $NH_2$ or $NO_2$, $R_2$ is H, $R_3$ is $CH_3$, $R_4$ is H, $R_5$ is —$CH_2CH_2SH$, $R_6$ is

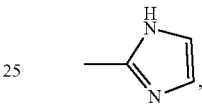

and n is 2 or 3.

In some aspects, $R_1$ is H, Cl, OH, $NH_2$ or $NO_2$, $R_2$ is H, $R_3$ is $CH_3$, $R_4$ is H, $R_5$ is

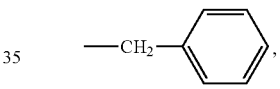

$R_6$ is

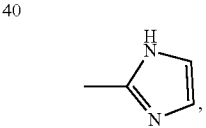

and n is 2 or 3.

In some aspects, $R_1$ is H, Cl, OH, $NH_2$ or $NO_2$, $R_2$ is H, $R_3$ is $CH_3$, $R_4$ is H, $R_5$ is

$R_6$ is

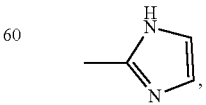

and n is 2 or 3.

In some aspects, $R_1$ is H, Cl, OH, $NH_2$ or $NO_2$, $R_2$ is H, $R_3$ is $CH_3$, $R_4$ is H, $R_5$ is

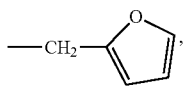

$R_6$ is

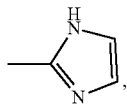

and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are H, and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are

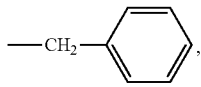

and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are

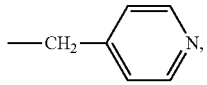

and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are

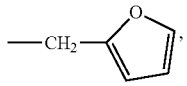

and n is 2 or 3.

In some aspects, $R_1$ is H, Cl, OH, $NH_2$ or $NO_2$, $R_2$ is —$OCH_3$, $R_3$ and $R_4$ are H, $R_5$ and $R_6$ are

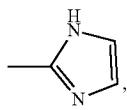

and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is

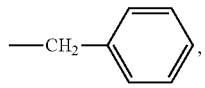

and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is

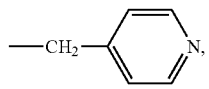

and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is

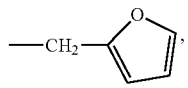

and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is

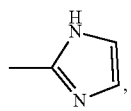

and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is

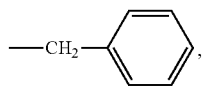

and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is

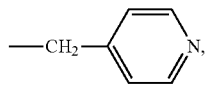

and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is

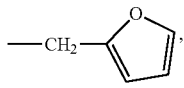

and n is 2 or 3.

In some aspects, $R_1$ is H, Cl, OH, $NH_2$ or $NO_2$, $R_2$ is $-OCH_3$, $R_3$ and $R_4$ are H, $R_5$ is $CH_3$, $R_6$ is

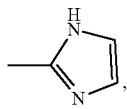

and n is 2 or 3.

In some aspects, $R_1$ is H, Cl, OH, $NH_2$ or $NO_2$, $R_2$ is $-OCH_3$, $R_3$ and $R_4$ are H, $R_5$ is $-CH_2CH_2SH$, $R_6$ is H, and n is 2 or 3.

In some aspects, $R_1$ is H, Cl, OH, $NH_2$ or $NO_2$, $R_2$ is $-OCH_3$, $R_3$ and $R_4$ are H, $R_5$ is $-CH_2CH_2SH$, $R_6$ is $CH_3$, and n is 2 or 3.

In some aspects, $R_1$ is H, Cl, OH, $NH_2$ or $NO_2$, $R_2$ is $-OCH_3$, $R_3$ and $R_4$ are H, $R_5$ is $-CH_2CH_2SH$, $R_6$ is

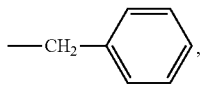

and n is 2 or 3.

In some aspects, $R_1$ is H, Cl, OH, $NH_2$ or $NO_2$, $R_2$ is $-OCH_3$, $R_3$ and $R_4$ are H, $R_5$ is $-CH_2CH_2SH$, $R_6$ is

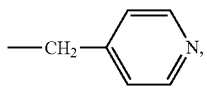

and n is 2 or 3.

In some aspects, $R_1$ is H, Cl, OH, $NH_2$ or $NO_2$, $R_2$ is $-OCH_3$, $R_3$ and $R_4$ are H, $R_5$ is $-CH_2CH_2SH$, $R_6$ is

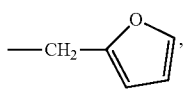

and n is 2 or 3.

In some aspects, $R_1$ is H, Cl, OH, $NH_2$ or $NO_2$, $R_2$ is $-OCH_3$, $R_3$ and $R_4$ are H, $R_5$ is $-CH_2CH_2SH$, $R_6$ is

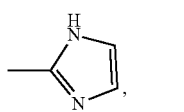

and n is 2 or 3.

In some aspects, $R_1$ is H, Cl, OH, $NH_2$ or $NO_2$, $R_2$ is $-OCH_3$, $R_3$ and $R_4$ are H, $R_5$ is

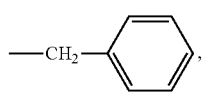

$R_6$ is H, and n is 2 or 3.

In some aspects, $R_1$ is H, Cl, OH, $NH_2$ or $NO_2$, $R_2$ is $-OCH_3$, $R_3$ and $R_4$ are H, $R_5$ is

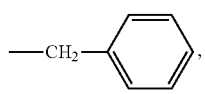

$R_6$ is $CH_3$, and n is 2 or 3.

In some aspects, $R_1$ is H, Cl, OH, $NH_2$ or $NO_2$, $R_2$ is $-OCH_3$, $R_3$ and $R_4$ are H, $R_5$ is

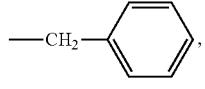

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ and $R_4$ are H, $R_5$ is

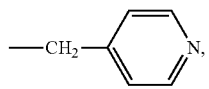

$R_6$ is

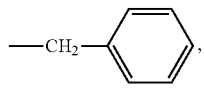

and n is 2 or 3.

In some aspects, $R_1$ is H, Cl, OH, $NH_2$ or $NO_2$, $R_2$ is $-OCH_3$, $R_3$ and $R_4$ are H, $R_5$ is

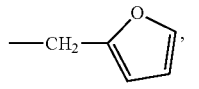

$R_6$ is

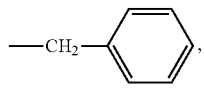

and n is 2 or 3.

In some aspects, $R_1$ is H, Cl, OH, $NH_2$ or $NO_2$, $R_2$ is $-OCH_3$, $R_3$ and $R_4$ are H, $R_5$ is

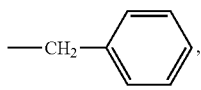

$R_6$ is

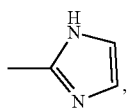

and n is 2 or 3.

In some aspects, $R_1$ is H, Cl, OH, $NH_2$ or $NO_2$, $R_2$ is —$OCH_3$, $R_3$ and $R_4$ are H, $R_5$ is

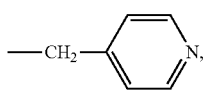

$R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is

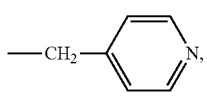

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

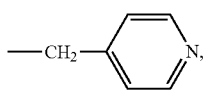

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

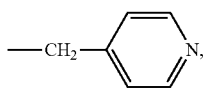

$R_6$ is

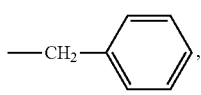

and n is 2 or 3.

In some aspects, $R_1$ is H, Cl, OH, $NH_2$ or $NO_2$, $R_2$ is —$OCH_3$, $R_3$ and $R_4$ are H, $R_5$ is

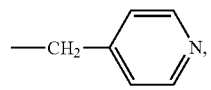

$R_6$ is

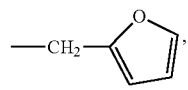

and n is 2 or 3.

In some aspects, $R_1$ is H, Cl, OH, $NH_2$ or $NO_2$, $R_2$ is —$OCH_3$, $R_3$ and $R_4$ are H, $R_5$ is

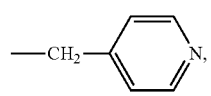

$R_6$ is

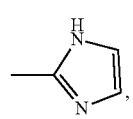

and n is 2 or 3.

In some aspects, $R_1$ is H, Cl, OH, $NH_2$ or $NO_2$, $R_2$ is —$OCH_3$, $R_3$ and $R_4$ are H, $R_5$ is

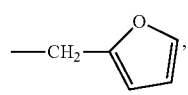

$R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is

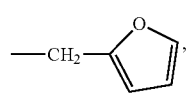

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

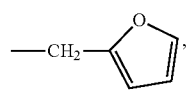

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

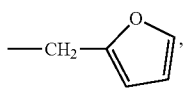

R₆ is

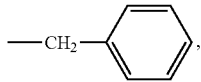

and n is 2 or 3.

In some aspects, R₁ is H, Cl, OH, NH₂ or NO₂, R₂ is —OCH₃, R₃ and R₄ are H, R₅ is

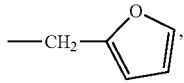

R₆ is

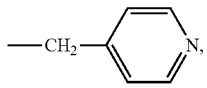

and n is 2 or 3.

In some aspects, R₁ is H, Cl, OH, NH₂ or NO₂, R₂ is —OCH₃, R₃ and R₄ are H, R₅ is

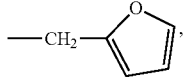

R₆ is

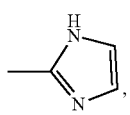

and n is 2 or 3.

In some aspects, R₁ is H, Cl, OH, NH₂ or NO₂, R₂ is —OCH₃, R₃ and R₄ are H, R₅ is

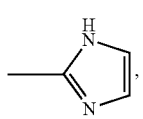

R₆ is H, and n is 2 or 3.

In some aspects, R₁ is H, Cl, OH, NH₂ or NO₂, R₂ is —OCH₃, R₃ and R₄ are H, R₅ is

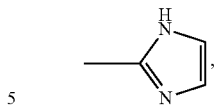

R₆ is CH₃, and n is 2 or 3.

In some aspects, R₁ is H, Cl, OH, NH₂ or NO₂, R₂ is —OCH₃, R₃ and R₄ are H, R₅ is

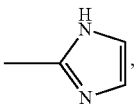

R₆ is —CH₂CH₂SH, and n is 2 or 3.

In some aspects, R₁ is H, Cl, OH, NH₂ or NO₂, R₂ is —OCH₃, R₃ and R₄ are H, R₅ is

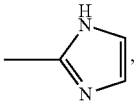

R₆ is

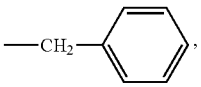

and n is 2 or 3.

In some aspects, R₁ is H, Cl, OH, NH₂ or NO₂, R₂ is —OCH₃, R₃ and R₄ are H, R₅ is

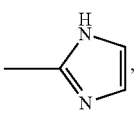

R₆ is

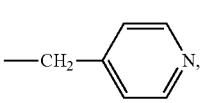

and n is 2 or 3.

In some aspects, R₁ is H, Cl, OH, NH₂ or NO₂, R₂ is —OCH₃, R₃ and R₄ are H, R₅ is

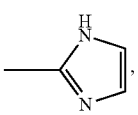

$R_6$ is

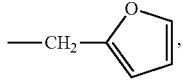

and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is —$CH_2CH_2SH$, $R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is

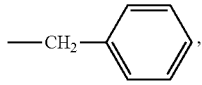

$R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is

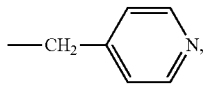

$R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is

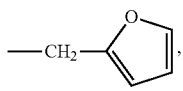

$R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is

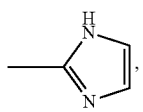

$R_6$ is H, and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

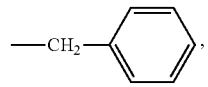

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

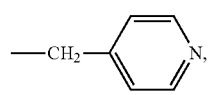

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

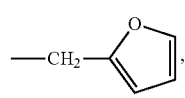

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

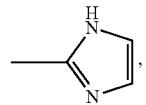

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

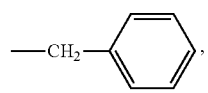

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

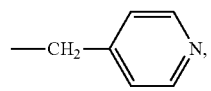

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are H, $R_5$ is

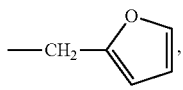

$R_6$ is —CH$_2$CH$_2$SH, and n is 2 or 3.

In some aspects, $R_1$ is H, Cl, OH, NH$_2$ or NO$_2$, $R_2$ is —OCH$_3$, $R_3$ and $R_4$ are H, $R_5$ is

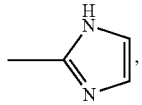

$R_6$ is —CH$_2$CH$_2$SH, and n is 2 or 3.

In some aspects, $R_1$ is H, Cl, OH, NH$_2$ or NO$_2$, $R_2$ is —OCH$_3$, $R_3$ and $R_4$ are H, $R_5$ is H, $R_6$ is

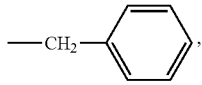

and n is 2 or 3.

In some aspects, $R_1$ is H, Cl, OH, NH$_2$ or NO$_2$, $R_2$ is —OCH$_3$, $R_3$ and $R_4$ are H, $R_5$ is CH$_3$, $R_6$ is

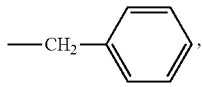

and n is 2 or 3.

In some aspects, $R_1$ is H, Cl, OH, NH$_2$ or NO$_2$, $R_2$ is —OCH$_3$, $R_3$ and $R_4$ are H, $R_5$ is —CH$_2$CH$_2$SH, $R_6$ is

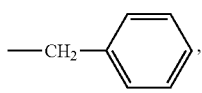

and n is 2 or 3.

In some aspects, $R_1$ is H, Cl, OH, NH$_2$ or NO$_2$, $R_2$ is —OCH$_3$, $R_3$ and $R_4$ are H, $R_5$ is

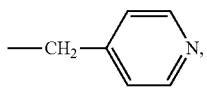

$R_6$ is

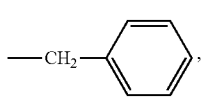

and n is 2 or 3.

In some aspects, $R_1$ is H, Cl, OH, NH$_2$ or NO$_2$, $R_2$ is —OCH$_3$, $R_3$ and $R_4$ are H, $R_5$ is

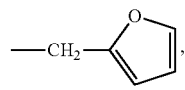

$R_6$ is

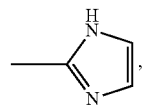

and n is 2 or 3.

In some aspects, $R_1$ is H, Cl, OH, NH$_2$ or NO$_2$, $R_2$ is —OCH$_3$, $R_3$ and $R_4$ are H, $R_5$ is

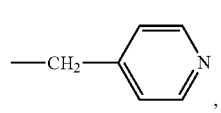

$R_6$ is

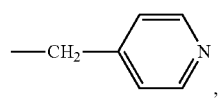

and n is 2 or 3.

In some aspects, $R_1$ is H, Cl, OH, NH$_2$ or NO$_2$, $R_2$ is —OCH$_3$, $R_3$ and $R_4$ are H, $R_5$ is H, $R_6$ is

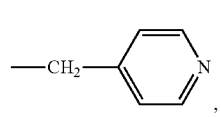

and n is 2 or 3.

In some aspects, $R_1$ is H, Cl, OH, NH$_2$ or NO$_2$, $R_2$ is —OCH$_3$, $R_3$ and $R_4$ are H, $R_5$ is CH$_3$, $R_6$ is and n is 2 or 3.

In some aspects, $R_1$ is H, Cl, OH, NH$_2$ or NO$_2$, $R_2$ is —OCH$_3$, $R_3$ and $R_4$ are H, $R_5$ is —CH$_2$CH$_2$SH, $R_6$ is and n is 2 or 3.

In some aspects, $R_1$ is H, Cl, OH, NH$_2$ or NO$_2$, $R_2$ is —OCH$_3$, $R_3$ and $R_4$ are H, $R_5$ is

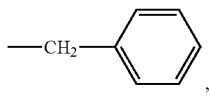,

R₆ is

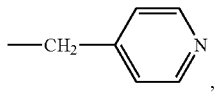, and n is 2 or 3.

In some aspects, R₁ is H, Cl, OH, NH₂ or NO₂, R₂ is —OCH₃, R₃ and R₄ are H, R₅ is

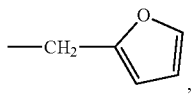,

R₆ is

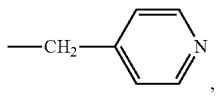, and n is 2 or 3.

In some aspects, R₁ is H, Cl, OH, NH₂ or NO₂, R₂ is —OCH₃, R₃ and R₄ are H, R₅ is

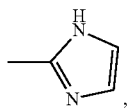,

R₆ is

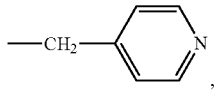, and n is 2 or 3.

In some aspects, R₁ is H, Cl, OH, NH₂ or NO₂, R₂ is —OCH₃, R₃ and R₄ are H, R₅ is H, R₆ is

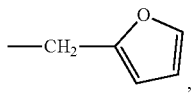, and n is 2 or 3.

In some aspects, R₁ is H, Cl, OH, NH₂ or NO₂, R₂ is —OCH₃, R₃ and R₄ are H, R₅ is CH₃, R₆ is

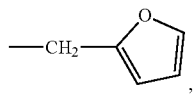, and n is 2 or 3.

In some aspects, R₁ is H, Cl, OH, NH₂ or NO₂, R₂ is —OCH₃, R₃ and R₄ are H, R₅ is —CH₂CH₂SH, R₆ is

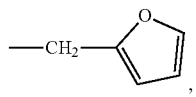, and n is 2 or 3.

In some aspects, R₁ is H, Cl, OH, NH₂ or NO₂, R₂ is —OCH₃, R₃ and R₄ are H, R₅ is

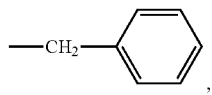,

R₆ is

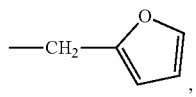, and n is 2 or 3.

In some aspects, R₁ is H, Cl, OH, NH₂ or NO₂, R₂ is —OCH₃, R₃ and R₄ are H, R₅ is

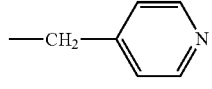,

R₆ is

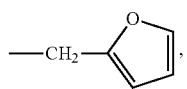, and n is 2 or 3.

In some aspects, R₁ is H, Cl, OH, NH₂ or NO₂, R₂ is —OCH₃, R₃ and R₄ are H, R₅ is

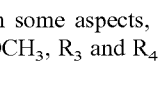

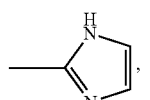, $R_6$ is

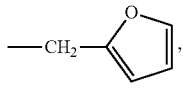

and n is 2 or 3.

In some aspects, $R_1$ is H, Cl, OH, $NH_2$ or $NO_2$, $R_2$ is —$OCH_3$, $R_3$ and $R_4$ are H, $R_5$ is H, $R_6$ is

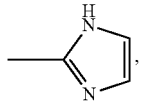

and n is 2 or 3.

In some aspects, $R_1$ is H, Cl, OH, $NH_2$ or $NO_2$, $R_2$ is —$OCH_3$, $R_3$ and $R_4$ are H, $R_5$ is $CH_3$, $R_6$ is

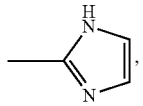

and n is 2 or 3.

In some aspects, $R_1$ is H, Cl, OH, $NH_2$ or $NO_2$, $R_2$ is —$OCH_3$, $R_3$ and $R_4$ are H, $R_5$ is —$CH_2CH_2SH$, $R_6$ is

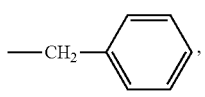

and n is 2 or 3.

In some aspects, $R_1$ is H, Cl, OH, $NH_2$ or $NO_2$, $R_2$ is —$OCH_3$, $R_3$ and $R_4$ are H, $R_5$ is

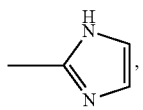

$R_6$ is

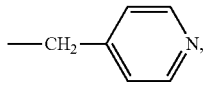

and n is 2 or 3.

In some aspects, $R_1$ is H, Cl, OH, $NH_2$ or $NO_2$, $R_2$ is —$OCH_3$, $R_3$ and $R_4$ are H, $R_5$ is

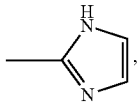

and n is 2 or 3.

In some aspects, $R_1$ is H, Cl, OH, $NH_2$ or $NO_2$, $R_2$ is —$OCH_3$, $R_3$ and $R_4$ are H, $R_5$ is

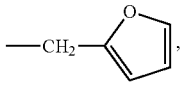

$R_6$ is

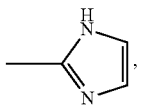

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are

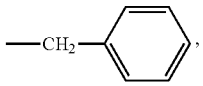

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are

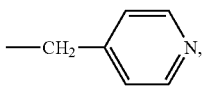

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are

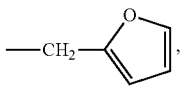

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ and $R_6$ are

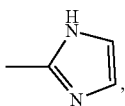

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

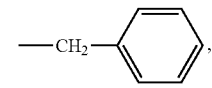

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

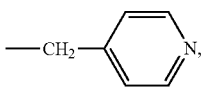

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

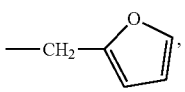

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

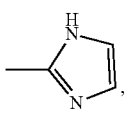

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

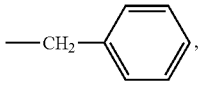

and n is 2 or 3.

In some aspects, $R_1$ is H, $R_2$ is —$OCH_3$, $R_3$ and $R_4$ are $CH_3$, $R_5$ is $CH_3$, $R_6$ is

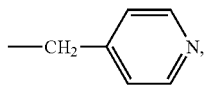

and n is 2.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

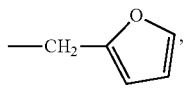

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

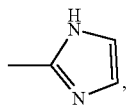

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_2CH_2SH$, $R_6$ is

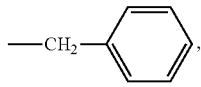

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

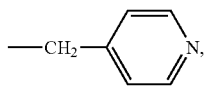

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

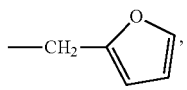

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

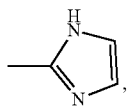

and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

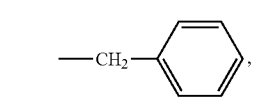

$R_6$ is H, and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

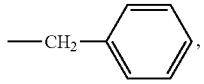

$R_6$ is $CH_3$, and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

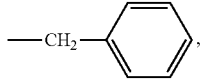

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

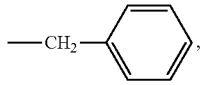

$R_6$ is

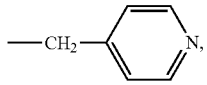

and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

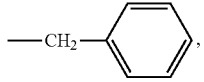

$R_6$ is

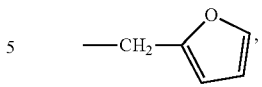

and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

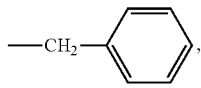

$R_6$ is

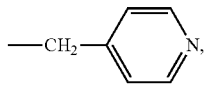

and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

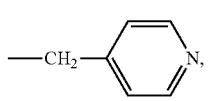

$R_6$ is H, and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

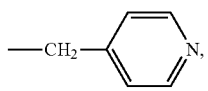

$R_6$ is $CH_3$, and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is

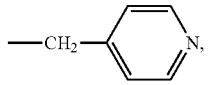

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ and $R_4$ are $CH_3$, $R_5$ is R₆ is

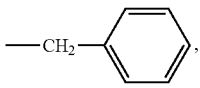

and n is 2 or 3.

In some aspects, R₁ is H, Cl, OH, NH₂ or NO₂, R₂ is —OCH₃, R₃ and R₄ are CH₃, R₅ is

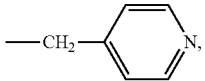

R₆ is

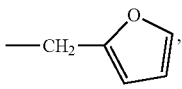

and n is 2 or 3.

In some aspects, R₁ is H, Cl, OH, NH₂ or NO₂, R₂ is —OCH₃, R₃ and R₄ are CH₃, R₅ is

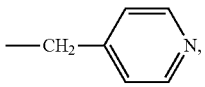

R₆ is

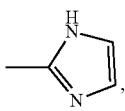

and n is 2 or 3.

In some aspects, R₁ is H, Cl, OH, NH₂ or NO₂, R₂ is —OCH₃, R₃ and R₄ are CH₃, R₅ is

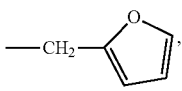

R₆ is H, and n is 2 or 3.

In some aspects, R₁ is H, Cl, OH, NH₂ or NO₂, R₂ is —OCH₃, R₃ and R₄ are CH₃, R₅ is

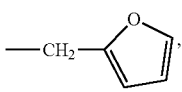

R₆ is CH₃, and n is 2 or 3.

In some aspects, R₁ is H, Cl, OH, NH₂ or NO₂, R₂ is —OCH₃, R₃ and R₄ are CH₃, R₅ is

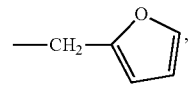

R₆ is —CH₂CH₂SH, and n is 2 or 3.

In some aspects, R₁ is H, Cl, OH, NH₂ or NO₂, R₂ is —OCH₃, R₃ and R₄ are CH₃, R₅ is

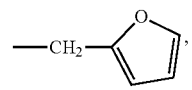

R₆ is

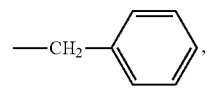

and n is 2 or 3.

In some aspects, R₁ is H, Cl, OH, NH₂ or NO₂, R₂ is —OCH₃, R₃ and R₄ are CH₃, R₅ is

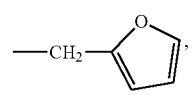

R₆ is

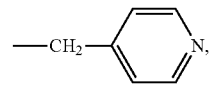

and n is 2 or 3.

In some aspects, R₁ is H, Cl, OH, NH₂ or NO₂, R₂ is —OCH₃, R₃ and R₄ are CH₃, R₅ is

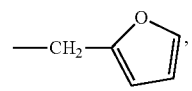

R₆ is

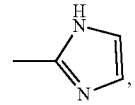

and n is 2 or 3.

In some aspects, R₁ is H, Cl, OH, NH₂ or NO₂, R₂ is —OCH₃, R₃ and R₄ are CH₃, R₅ is

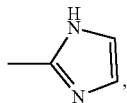

$R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

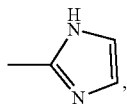

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

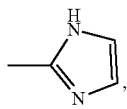

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

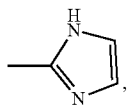

$R_6$ is

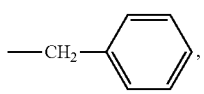

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

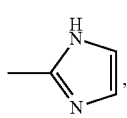

$R_6$ is

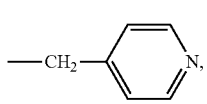

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

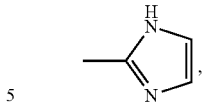

$R_6$ is

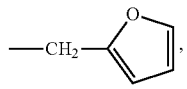

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

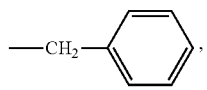

$R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

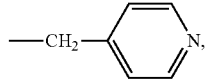

$R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

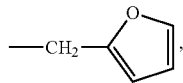

$R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

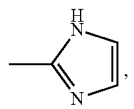

$R_6$ is H, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

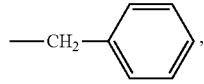

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

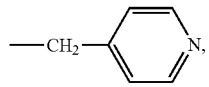

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

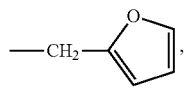

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

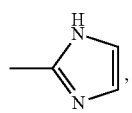

$R_6$ is $CH_3$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

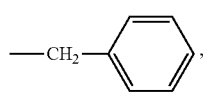

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

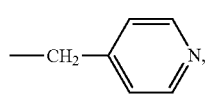

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

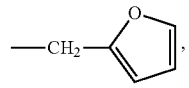

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

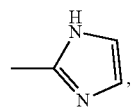

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

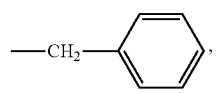

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

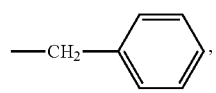

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

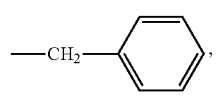

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

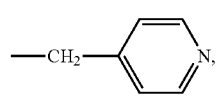

$R_6$ is

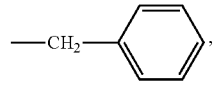

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

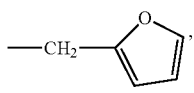

$R_6$ is

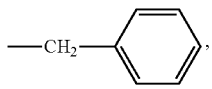

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

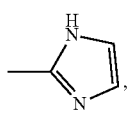

$R_6$ is

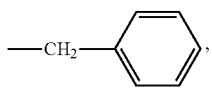

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

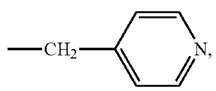

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

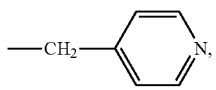

and n is 2 or 3.

In some aspects $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

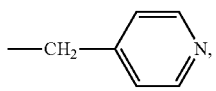

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

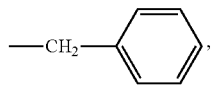

$R_6$ is

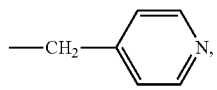

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

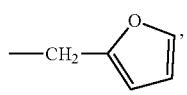

$R_6$ is

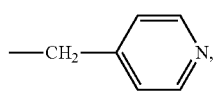

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

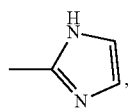

$R_6$ is

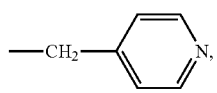

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

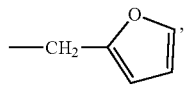

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

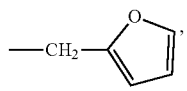

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

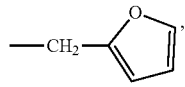

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

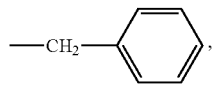

$R_6$ is

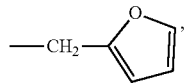

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

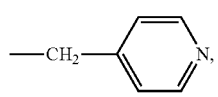

$R_6$ is

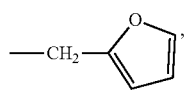

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

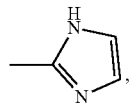

$R_6$ is

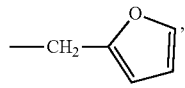

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is H, $R_6$ is

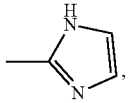

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is $CH_3$, $R_6$ is

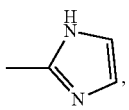

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is —$CH_2CH_2SH$, $R_6$ is

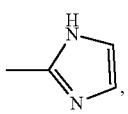

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

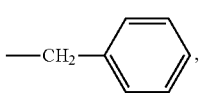

$R_6$ is

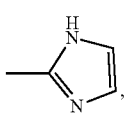

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

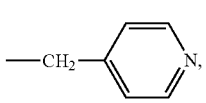

$R_6$ is

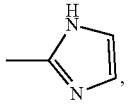

and n is 2 or 3.

In some aspects, $R_1$ is H, Cl, OH, $NH_2$ or $NO_2$, $R_2$ is —$OCH_3$, $R_3$ and $R_4$ are $CH_3$, $R_5$ is

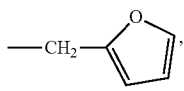

$R_6$ is

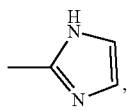

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are H, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are $CH_3$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are —$CH_2CH_2SH$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are

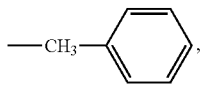

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are

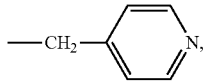

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are

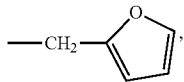

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ and $R_6$ are

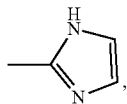

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is H, $R_6$ is $CH_3$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is H, $R_6$ is

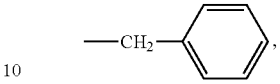

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is H, $R_6$ is

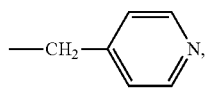

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is H, $R_6$ is

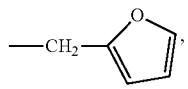

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is H, $R_6$ is

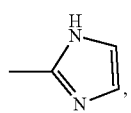

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is $CH_3$, $R_6$ is H, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is $CH_3$, $R_6$ is

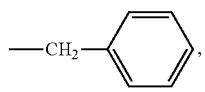

and n is 2 or 3.

In some aspects, $R_1$ is H, Cl, OH $NH_2$ or $NO_2$, $R_2$ is —$OCH_3$, $R_3$ is H, $R_4$ is $CH_3$, $R_5$ is $CH_3$, $R_6$ is

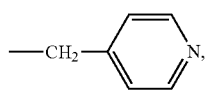

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $CH_3$, $R_6$ is

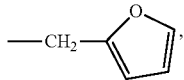

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $CH_3$, $R_6$ is

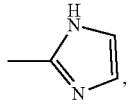

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is H, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is $CH_3$, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is

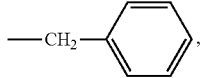

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is

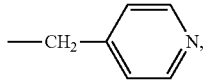

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is

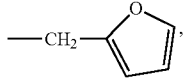

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is

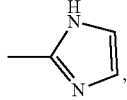

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

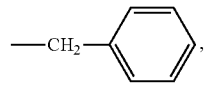

$R_6$ is H, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

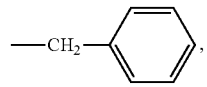

$R_6$ is $CH_3$, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

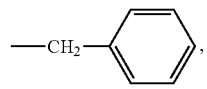

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

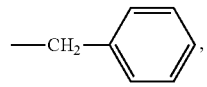

$R_6$ is

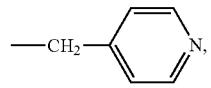

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

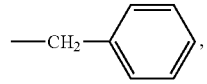

$R_6$ is

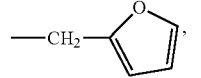

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

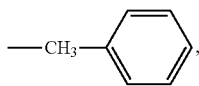

$R_6$ is

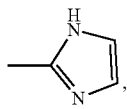

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

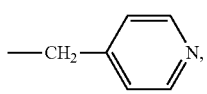

$R_6$ is H, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

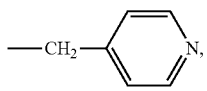

$R_6$ is $CH_3$, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

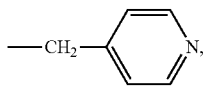

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

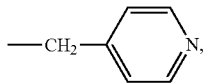

$R_6$ is

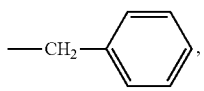

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

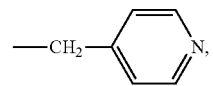

$R_6$ is

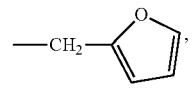

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

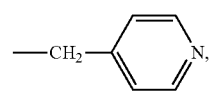

$R_6$ is

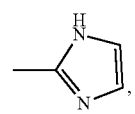

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

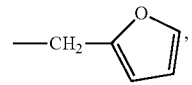

$R_6$ is H, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

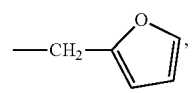

$R_6$ is $CH_3$, SH, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

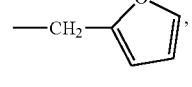

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

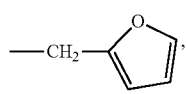

$R_6$ is

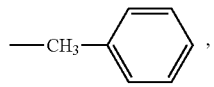

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

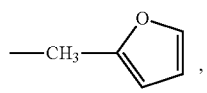

$R_6$ is

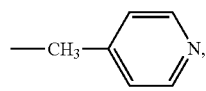

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

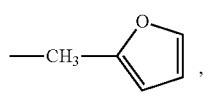

$R_6$ is

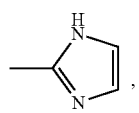

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

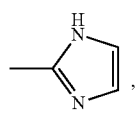

$R_6$ is H, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

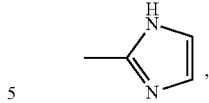

$R_6$ is $CH_3$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

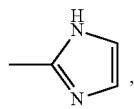

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

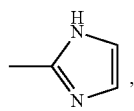

$R_6$ is

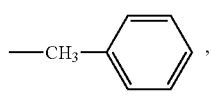

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

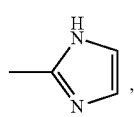

$R_6$ is

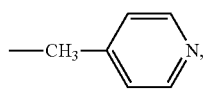

and n is 2 or 3.

In some aspects, $R_1$ is H, Cl, OH, $NH_2$ or $NO_2$, $R_2$ is —$OCH_3$, $R_3$ is H, $R_4$ is $CH_3$, $R_5$ is

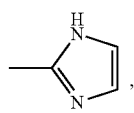

R₆ is

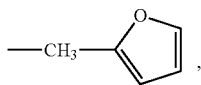, and n is 2 or 3.

In some aspects, R₁ is H, Cl, OH, NH₂ or NO₂, R₂ is —OCH₃, R₃ is H, R₄ is CH₃, R₅ is CH₃, R₆ is H, and n is 2 or 3.

In some aspects, R₁ is H, Cl, OH, NH₂ or NO₂, R₂ is —OCH₃, R₃ is H, R₄ is CH₃, R₅ is —CH₂CH₂SH, R₆ is H, and n is 2 or 3.

In some aspects, R₁ is H, Cl, OH, NH₂ or NO₂, R₂ is —OCH₃, R₃ is H, R₄ is CH₃, R₅ is

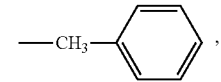,

R₆ is H, and n is 2 or 3.

In some aspects, R₁ is H, Cl, OH, NH₂ or NO₂, R₂ is —OCH₃, R₃ is H, R₄ is CH₃, R₅ is

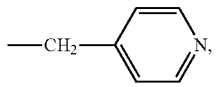,

R₆ is H, and n is 2 or 3.

In some aspects, R₁ is H, Cl, OH, NH₂ or NO₂, R₂ is —OCH₃, R₃ is H, R₄ is CH₃, R₅ is

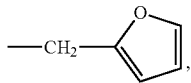,

R₆ is H, and n is 2 or 3.

In some aspects, R₁ is H, Cl, OH, NH₂ or NO₂, R₂ is —OCH₃, R₃ is H, R₄ is CH₃, R₅ is

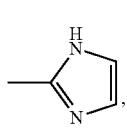,

R₆ is H, and n is 2 or 3.

In some aspects, R₁ is H, Cl, OH, NH₂ or NO₂, R₂ is —OCH₃, R₃ is H, R₄ is CH₃, R₅ is H, R₆ is CH₃, and n is 2 or 3.

In some aspects, R₁ is H, Cl, OH, NH₂ or NO₂, R₂ is —OCH₃, R₃ is H, R₄ is CH₃, R₅ is —CH₂CH₂SH, R₆ is CH₃, and n is 2 or 3.

In some aspects, R₁ is H, Cl, OH, NH₂ or NO₂, R₂ is —OCH₃, R₃ is H, R₄ is CH₃, R₅ is

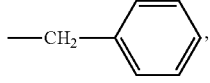,

R₆ is CH₃, and n is 2 or 3.

In some aspects, R₁ is H, Cl, OH, NH₂ or NO₂, R₂ is —OCH₃, R₃ is H, R₄ is CH₃, R₅ is

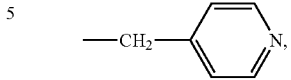,

R₆ is CH₃, and n is 2 or 3.

In some aspects, R₁ is H, Cl, OH, NH₂ or NO₂, R₂ is —OCH₃, R₃ is H, R₄ is CH₃, R₅ is

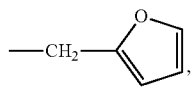,

R₆ is CH₃, and n is 2 or 3.

In some aspects, R₁ is H, Cl, OH, NH₂ or NO₂, R₂ is —OCH₃, R₃ is H, R₄ is CH₃, R₅ is

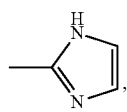,

R₆ is CH₃, and n is 2 or 3.

In some aspects, R₁ is H, Cl, OH, NH₂ or NO₂, R₂ is —OCH₃, R₃ is H, R₄ is CH₃, R₅ is H, R₆ is —CH₂CH₂SH, and n is 2 or 3.

In some aspects, R₁ is H, Cl, OH, NH₂ or NO₂, R₂ is —OCH₃, R₃ is H, R₄ is CH₃, R₅ is CH₃, R₆ is —CH₂CH₂SH, and n is 2 or 3.

In some aspects, R₁ is H, Cl, OH, NH₂ or NO₂, R₂ is —OCH₃, R₃ is H, R₄ is CH₃, R₅ is

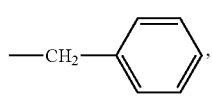,

R₆ is —CH₂CH₂SH and n is 2 or 3.

In some aspects, R₁ is H, Cl, OH, NH₂ or NO₂, R₂ is —OCH₃, R₃ is H, R₄ is CH₃, R₅ is

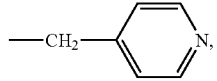,

R₆ is —CH₂CH₂SH, and n is 2 or 3.

In some aspects, R₁ is H, Cl, OH, NH₂ or NO₂, R₂ is —OCH₃, R₃ is H, R₄ is CH₃, R₅ is

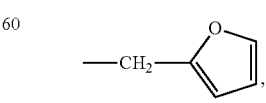,

R₆ is —CH₂CH₂SH, and n is 2 or 3.

In some aspects, R₁ is H, Cl, OH, NH₂ or NO₂, R₂ is —OCH₃, R₃ is H, R₄ is CH₃, R₅ is

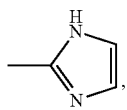

$R_6$ is —CH$_2$CH$_2$SH, and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is H, $R_6$ is

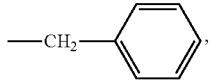

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is CH$_3$, $R_6$ is

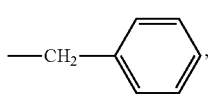

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is —CH$_2$CH$_2$SH, $R_6$ is

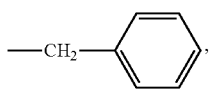

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is

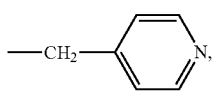

$R_6$ is

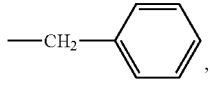

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is

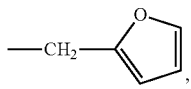

$R_6$ is

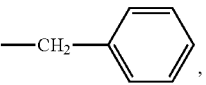

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is

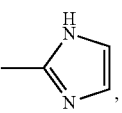

$R_6$ is

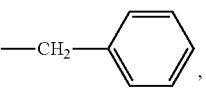

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is H, $R_6$ is

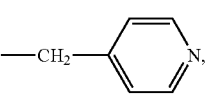

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is CH$_3$, $R_6$ is

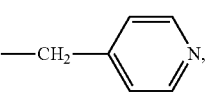

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is —CH$_2$CH$_2$SH, $R_6$ is

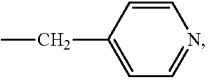

and n is 2 or 3.

In some aspects, $R_1$ is H, Cl, OH, NH$_2$ or NO$_2$, $R_2$ is —OCH$_3$, $R_3$ is H, $R_4$ is CH$_3$, $R_5$ is

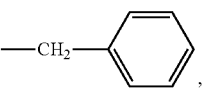

$R_6$ is

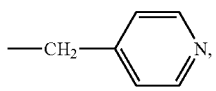

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

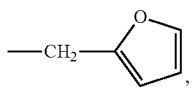

$R_6$ is

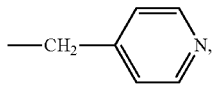

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

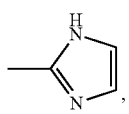

$R_6$ is

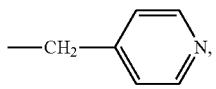

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is H, $R_6$ is

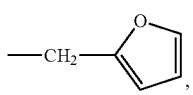

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $CH_3$, $R_6$ is

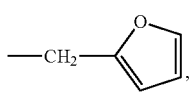

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is

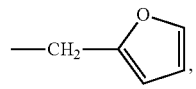

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

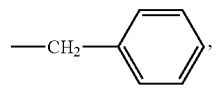

$R_6$ is

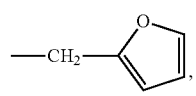

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

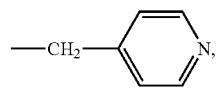

$R_6$ is

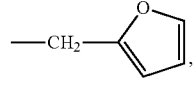

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

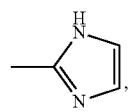

$R_6$ is

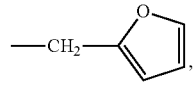

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is H, $R_6$ is

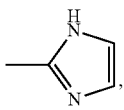

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $CH_3$, $R_6$ is

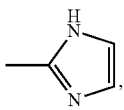

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is $-CH_2CH_2SH$, $R_6$ is

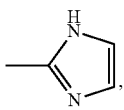

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

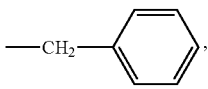

$R_6$ is

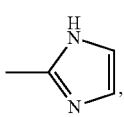

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

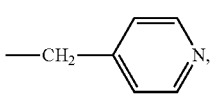

$R_6$ is

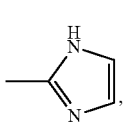

and n is 2 or 3.

In some aspects, $R_1$ is H, Cl, OH, $NH_2$ or $NO_2$, $R_2$ is $-OCH_3$, $R_3$ is H, $R_4$ is $CH_3$, $R_5$ is

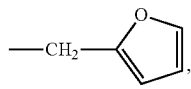

$R_6$ is

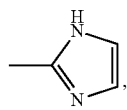

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are $CH_3$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are $-CH_2CH_2SH$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are

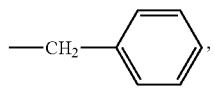

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are

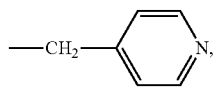

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are

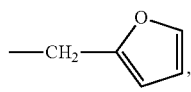

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ and $R_6$ are

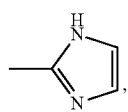

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is H, $R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is —CH₂—(phenyl), n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is —CH₂—(4-pyridyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is —CH₂—(2-furyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is —(2-imidazolyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is H, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is —CH₂—(phenyl), and n is 2 or 3.

In some aspects $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is —CH₂—(4-pyridyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is —CH₂—(2-furyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is —(2-imidazolyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is H, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is —CH₂—(phenyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is —CH₂—(4-pyridyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is —CH₂—(2-furyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is —(2-imidazolyl), and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

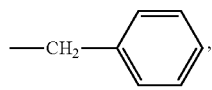

$R_6$ is H and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

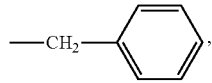

$R_6$ is $CH_3$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

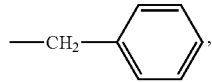

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

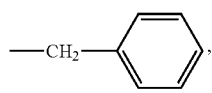

$R_6$ is

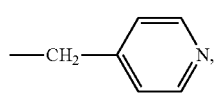

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

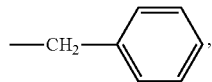

$R_6$ is

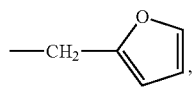

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

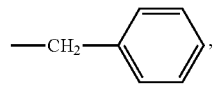

$R_6$ is

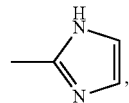

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

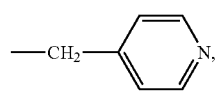

$R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

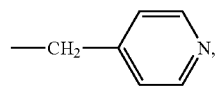

$R_6$ is $CH_3$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

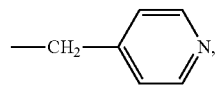

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

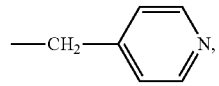

$R_6$ is

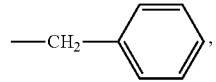

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

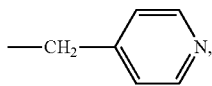

$R_6$ is

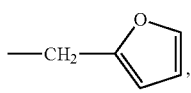

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

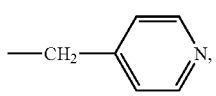

$R_6$ is

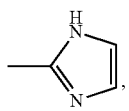

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

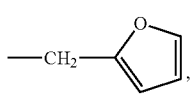

$R_6$ is H, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

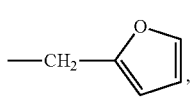

$R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

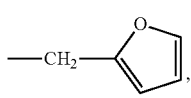

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

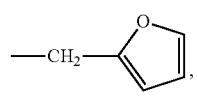

$R_6$ is

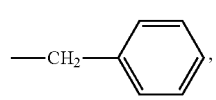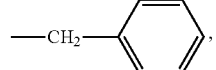

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

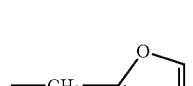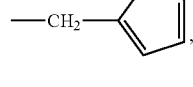

$R_6$ is

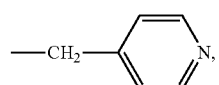

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

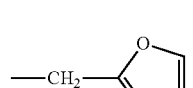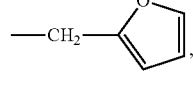

$R_6$ is

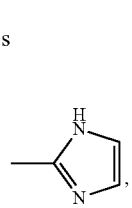

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

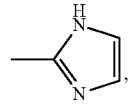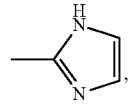

$R_6$ is H, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

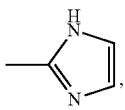

$R_6$ is $CH_3$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

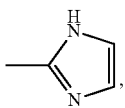

$R_6$ is $-CH_2CH_2SH$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

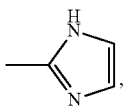

$R_6$ is

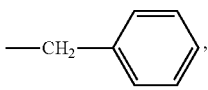

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

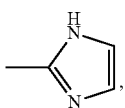

$R_6$ is

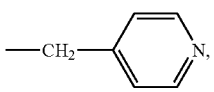

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

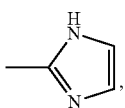

$R_6$ is

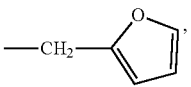

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $CH_3$, $R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $-CH_2CH_2SH$, $R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

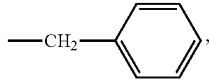

$R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

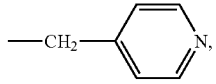

$R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

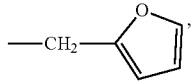

$R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

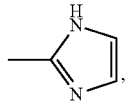

$R_6$ is H, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is H, $R_6$ is $CH_3$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $-CH_2CH_2SH$, $R_6$ is $CH_3$, and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

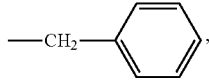

$R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

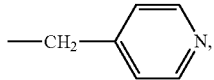

$R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

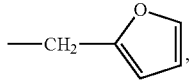

$R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

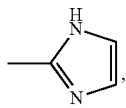

$R_6$ is $CH_3$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

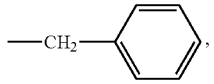

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

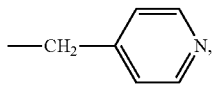

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

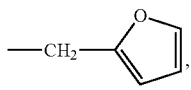

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

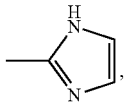

$R_6$ is —$CH_2CH_2SH$, and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is H, $R_6$ is

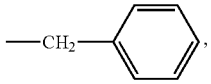

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is $CH_3$, $R_6$ is

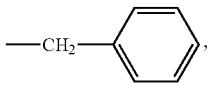

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is —$CH_2CH_2SH$, $R_6$ is

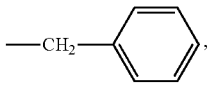

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

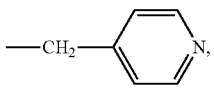

$R_6$ is

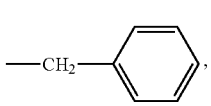

and n is 2 or 3.

In some aspects, $R_1$ is H, Cl, OH, $NH_2$ or $NO_2$, $R_2$ is —$OCH_3$, $R_3$ is $CH_3$, $R_4$ is H, $R_5$ is

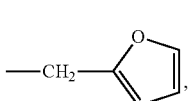

$R_6$ is

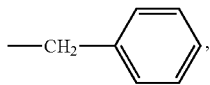

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

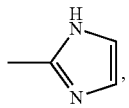

$R_6$ is

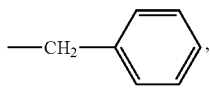

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is H, $R_6$ is

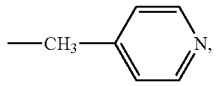

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $CH_3$, $R_6$ is

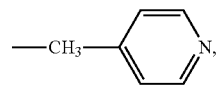

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $-CH_2CH_2SH$, $R_6$ is

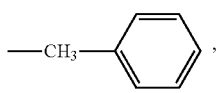

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $R_6$ is

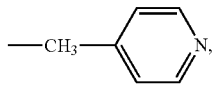

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

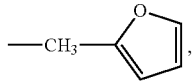

$R_6$ is

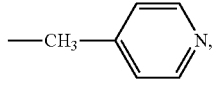

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

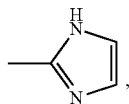

$R_6$ is

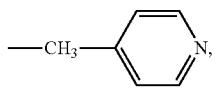

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is H, $R_6$ is

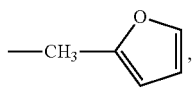

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $CH_3$, $R_6$ is

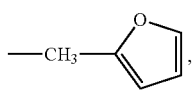

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $-CH_2CH_2SH$, $R_6$ is

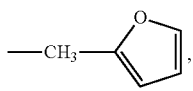

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

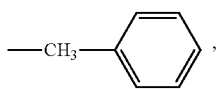

$R_6$ is

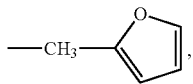

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

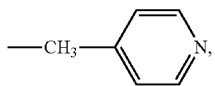

$R_6$ is

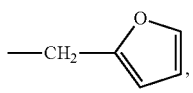

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

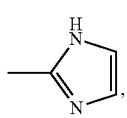

$R_6$ is

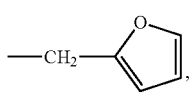

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is H, $R_6$ is

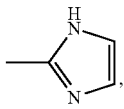

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $CH_3$, $R_6$ is

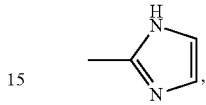

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is $-CH_2CH_2SH$, $R_6$ is

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

$R_6$ is

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

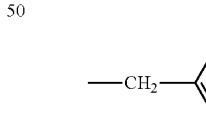

$R_6$ is

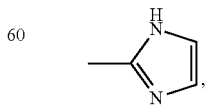

and n is 2 or 3.

In some aspects, $R_1$ is H, Cl, OH, $NH_2$ or $NO_2$, $R_2$ is $-OCH_3$, $R_3$ is $CH_3$, $R_4$ is H, $R_5$ is

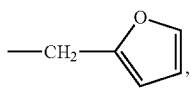

$R_6$ is

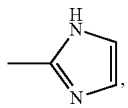

and n is 2 or 3.

The invention also provides pharmaceutical compositions of the compounds disclosed herein. In some embodiments, the pharmaceutical composition may include a compound of formulae (I) or (II) and a pharmaceutically acceptable carrier, diluent or excipient.

The invention further relates to the treatment of autoimmune diseases by the administration of a compound of a compound of Formula (I) or a compound of Formula (II). Compounds of Formula (I) and Formula (II) can be useful for the treatment of autoimmune diseases including systemic lupus erythematosus (SLE), lupus nephritis (LN), rheumatoid arthritis, juvenile rheumatoid arthritis, Wegener's disease, inflammatory bowel disease, idiopathic thrombocytopenic purpura (ITP), thrombotic thrombocytopenic purpura (TTP). autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, scleroderma, polymyositis and glomerulonephritis. Preferably, the autoimmune disease is SLE.

The invention further relates to the treatment of monogenic disorders by the administration of a compound of Formula (I) or a compound of Formula (II). Compounds of Formula (I) and Formula (II) can be useful for the treatment of monogenic disorders including Aicardi-Goutierre's Syndrome (AGS) or spondyloenchondrodysplasia (SPENCD). Preferably, the monogenic disorder is AGS.

In one embodiment, the method of treatment includes the administration of a pharmaceutical described herein.

The invention also relates to a method for the treatment of an autoimmune disease or a monogenic disorder, the method comprising administering an effective amount of a compound of Formula (III) or a prodrug or metabolite thereof,

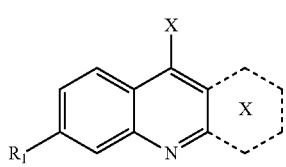

(III)

wherein
$R_1$ is —H, halogen, —OH, —OCH$_3$, —NH$_2$, —NMe$_2$, —N(H)C(O)R$_7$ or —NO$_2$,
  wherein $R_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

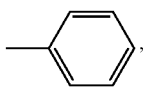

ring X is absent or

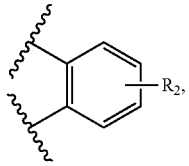

wherein $R_2$ is —H, halogen, —NMe$_2$, —OCH$_3$ or —OCH$_2$CH$_3$;
X is —H, —NH$_2$,

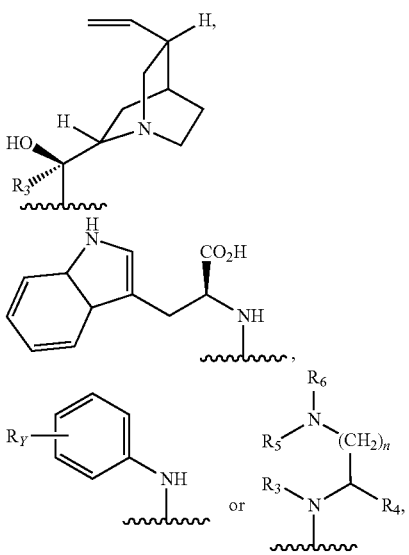

wherein
$R_3$ is —H or —CH$_3$;
$R_4$ is —H or —CH$_3$;
$R_5$ and $R_6$ are independently —H, —CH$_3$, —CH$_2$CH$_3$, —CH$_2$CH$_2$SH, —CH$_2$CH$_2$OH,

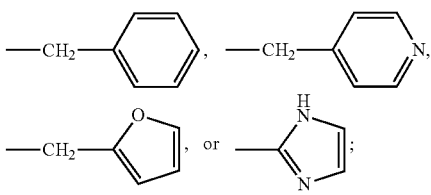

$R_Y$ is —NO$_2$, —C(O)OCH$_2$CH$_3$ or —N(H)SO$_2$Me; and
n is 2 or 3;
to a patient in need thereof.

In some embodiments of the method, the compound is of formula (IIIa):

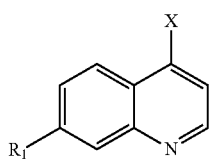

(IIIa)

wherein $R_1$ is —H, halogen, —OH, —OCH$_3$, —NH$_2$, —N(H)C(O)R$_7$ or —NO$_2$, wherein R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_3$, —CF$_3$, —CH$_2$CF$_3$ or

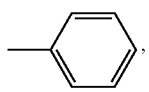

X is

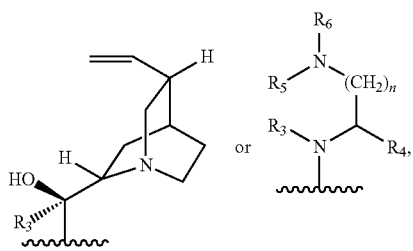

wherein $R_3$ is —H or —CH$_3$;

$R_4$ is —H or —CH$_3$;

$R_5$ and $R_6$ are independently —H, —CH$_3$, —CH$_2$CH$_3$ or —CH$_2$CH$_2$OH; and n is 2 or 3.

In some embodiments of the method, the compound is of formula (IIIb):

(IIIb)

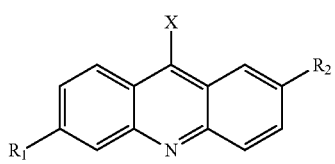

wherein $R_1$ is —H, halogen, —OH, —OCH$_3$, —NH$_2$, —N(H)C(O)R$_7$ or —NO$_2$, wherein R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

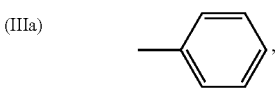

$R_2$ is —H, halogen, —OCH$_3$ or —OCH$_2$CH$_3$;

X is —NH$_2$,

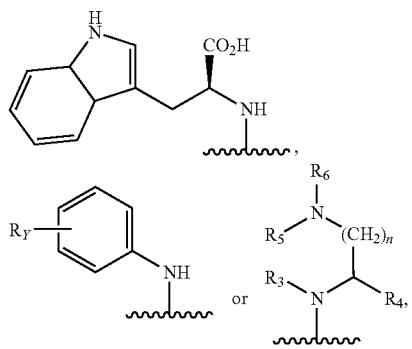

wherein $R_3$ is —H or —CH$_3$;

$R_4$ is —H or —CH$_3$;

$R_5$ and $R_6$ are independently —H, —CH$_3$, —CH$_2$CH$_3$, —CH$_2$CH$_2$SH, —CH$_2$CH$_2$OH,

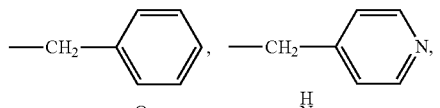

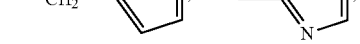

$R_Y$ is —NO$_2$, —C(O)OCH$_2$CH$_3$ or —N(H)SO$_2$Me; and n is 2 or 3.

In some embodiments of the method, X is —NH$_2$.

In some embodiments of the method, X is

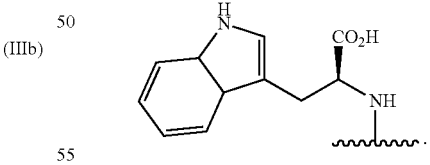

In some embodiments of the method, X is

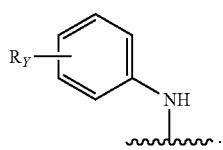

In some embodiments of the method, X is

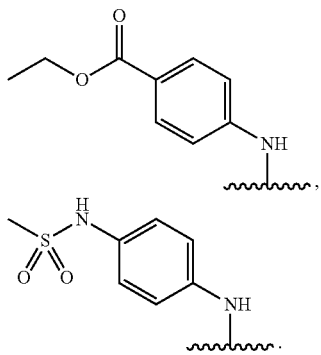

or

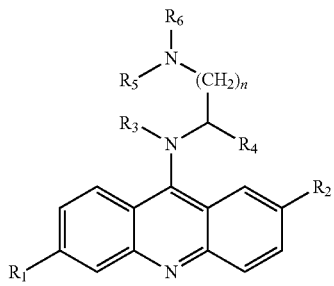

In some embodiments of the method, the compound of Formula (IIIc) or a prodrug or metabolite thereof, (IIIc)

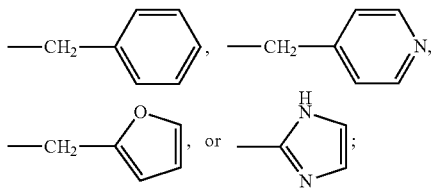

wherein
R$_1$ is —H, halogen, —OH, —OCH$_3$, —NH$_2$, —N(H)C(O)R$_7$ or —NO$_2$;
R$_2$ is —H or —OCH$_3$;
R$_3$ and R$_4$ are independently —H or —CH$_3$;
R$_5$ and R$_6$ are independently —H, —CH$_3$, —CH$_2$CH$_3$, —CH$_2$CH$_2$SH, —CH$_2$CH$_2$OH,

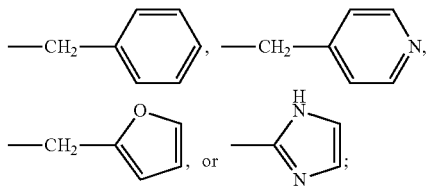

R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

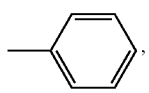

and
n is 2 or 3.

In some embodiments of the method,
R$_1$ is —H, —Cl, —OH, —NH$_2$, —N(H)C(O)R$_7$ or —NO$_2$;
R$_2$ is —H or —OCH$_3$;
R$_3$ and R$_4$ are independently —H or —CH$_3$;
R$_5$ and R$_6$ are independently —H, —CH$_3$, —CH$_2$CH$_2$SH,

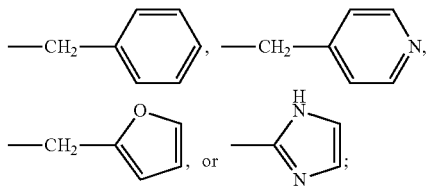

R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

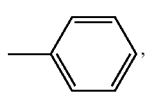

and
n is 2 or 3.

In some embodiments of the method,
R$_1$ is —NH$_2$ or —N(H)C(O)R$_7$;
R$_2$ is —OCH$_3$;
R$_3$ is —CH$_3$;
R$_4$ is —H;
R$_5$ is —CH$_3$;
R$_6$ is

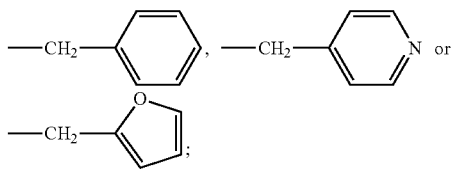

R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

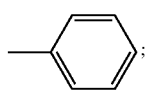

and
n is 2.

In some embodiments of the method,
R$_1$ is NH$_2$ or N(H)C(O)R$_7$;
R$_2$ is —OCH$_3$;
R$_3$ is —CH$_3$;
R$_4$ is —H;
R$_5$ is —CH$_3$;

$R_6$ is

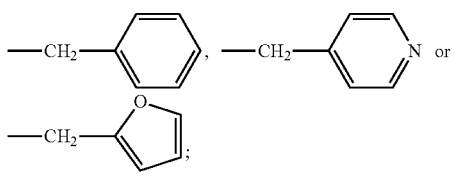

$R_7$ is —OCH$_2$CH$_3$, CH$_2$CH$_2$CH$_2$CH$_2$CH$_3$, —CF$_3$ or

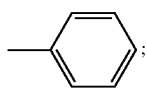

and
n is 2.
In some embodiments of the method,
$R_1$ is —NH$_2$;
$R_2$ is —OCH$_3$;
$R_3$ is —CH$_3$;
$R_4$ is —H;
$R_5$ is —CH$_3$;
$R_6$ is

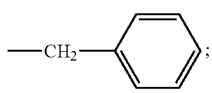

and
n is 2.
In some embodiments of the method,
$R_1$ is —NH$_2$;
$R_2$ is —OCH$_3$;
$R_3$ is —CH$_3$;
$R_4$ is —H;
$R_5$ is —CH$_3$;
$R_6$ is

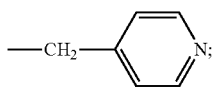

and
n is 2.
In some embodiments of the method,
$R_1$ is —NH$_2$;
$R_2$ is —OCH$_3$;
$R_3$ is —CH$_3$;
$R_4$ is —H;
$R_5$ is —CH$_3$;
$R_6$ is

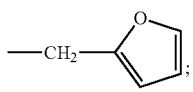

and
n is 2.

In some embodiments of the method, $R_1$ is —N(H)C(O)$R_7$.
In some embodiments of the method, $R_1$ is —N(H)C(O)$R_7$;
$R_2$ is —OCH$_3$;
$R_3$ is —CH$_3$;
$R_4$ is —H;
$R_5$ is —CH$_3$;
$R_6$ is

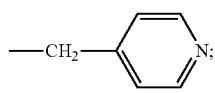

and
n is 2.
In some embodiments of the method,
$R_1$ is —N(H)C(O)CH$_2$CH$_2$CH$_2$CH$_2$CH$_3$;
$R_2$ is —OCH$_3$;
$R_3$ is —CH$_3$;
$R_4$ is —H;
$R_5$ is —CH$_3$;
$R_6$ is

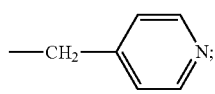

and
n is 2.
In some embodiments of the method,
$R_1$ is —N(H)C(O)CF$_3$;
$R_2$ is —OCH$_3$;
$R_3$ is —CH$_3$;
$R_4$ is —H;
$R_5$ is —CH$_3$;
$R_6$ is

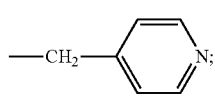

and
n is 2.
In some embodiments of the method,
$R_1$ is —N(H)C(O)$R_7$;
$R_2$ is —OCH$_3$; $R_3$ is CH$_3$;
$R_4$ is —H;
$R_5$ is —CH$_3$;
$R_6$ is

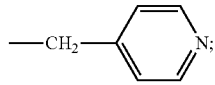

$R_7$ is

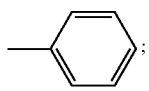

and n is 2.

In some embodiments of the method, the treatment is of an autoimmune disease. The autoimmune disease may be selected from the group consisting of systemic lupus erythematosus (SLE), lupus nephritis (LN), rheumatoid arthritis, juvenile rheumatoid arthritis, Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, scleroderma, polymyositis and glomerulonephritis.

In some embodiments of the method, the autoimmune disease is SLE.

In some embodiments of the method, the autoimmune disease involves inhibition of cGAS activity.

In some embodiments of the method, the treatment of a monogenic disorder.

In some embodiments of the method, the monogenic disorder is Aicardi-Goutierre's Syndrome (AGS) or spondyloenchondrodysplasia (SPENCD).

In some embodiments of the method, the monogenic disorder is AGS.

EXAMPLES

Example 1

Anti-malarial Drugs are Predicted to Block cGAS-DNA Interaction by Computational Analysis The structural domains of cGAS present two highly attractive drug targets, the catalytic site and a regulatory site, both with established key residues in relatively compressed regions and both with known substrates/ligands. The pronounced conformational change in the dsDNA bound enzyme compared to apo enzyme lends further enthusiasm to the hypothesis that cGAS activity could be inhibited by appropriately-designed small molecules.

In an effort to identify drugs to block cGAS activity, we performed in silico screening of chemical and drug libraries using the publicly available software, such as VINA™ and DOCK™. Using Computational Analysis with the Autodock VINA™ platform, we identified hydroxychloroquine (HCQ), 9-amino-6-chloro-2-methoxyacridine and quinacrine to interact at the Zn thumb and spine regions of cGAS involving simultaneous enzyme and DNA binding. The two main binding events, at the zinc thumb and at the spine, appear to occur within 3-10 Angstroms of the amino acids shown by mutation to be needed for dsDNA binding. The binding affinity was calculated by AutoDock VINA™ software. See Table 2.

Anti-malarial Drugs Inhibit DNA Binding to cGAS and dsDNA/cGAS Complex Formation To determine whether these anti-malarial drugs could inhibit DNA binding to cGAS in vitro, we performed DNA binding studies by the electrophoretic mobility shift assay (EMSA). As previously shown, addition of increasing concentrations of cGAS to a constant concentration of ds DNA (ISD), results in the protein retarding migration of ISD on the gel ('gel shift') and less free DNA (FIG. 1, left panel). To test whether HCQ as a model antimalarial could attenuate the gel shift, we used constant concentrations of both ISD and cGAS (FIG. 1, right panel) in the presence of increasing concentrations of HCQ. As shown, increasing the concentration of HCQ reduced the gel shift caused by the formation of dsDNA/cGAS complexes and led to increasing free DNA at the bottom of the gel. This result indicates that HCQ blocked dsDNA/cGAS binding. Inhibition of formation of dsDNA/cGAS higher order complexes by antimalarial drugs are especially interesting and important since cGAS is activated by dsDNA induced oligomerization and dsDNA/cGAS complex formation is required for cGAS activation.

Antimalarial Drugs Differentially Inhibit cGAS Activity and cGAMP Production

Figure 2:
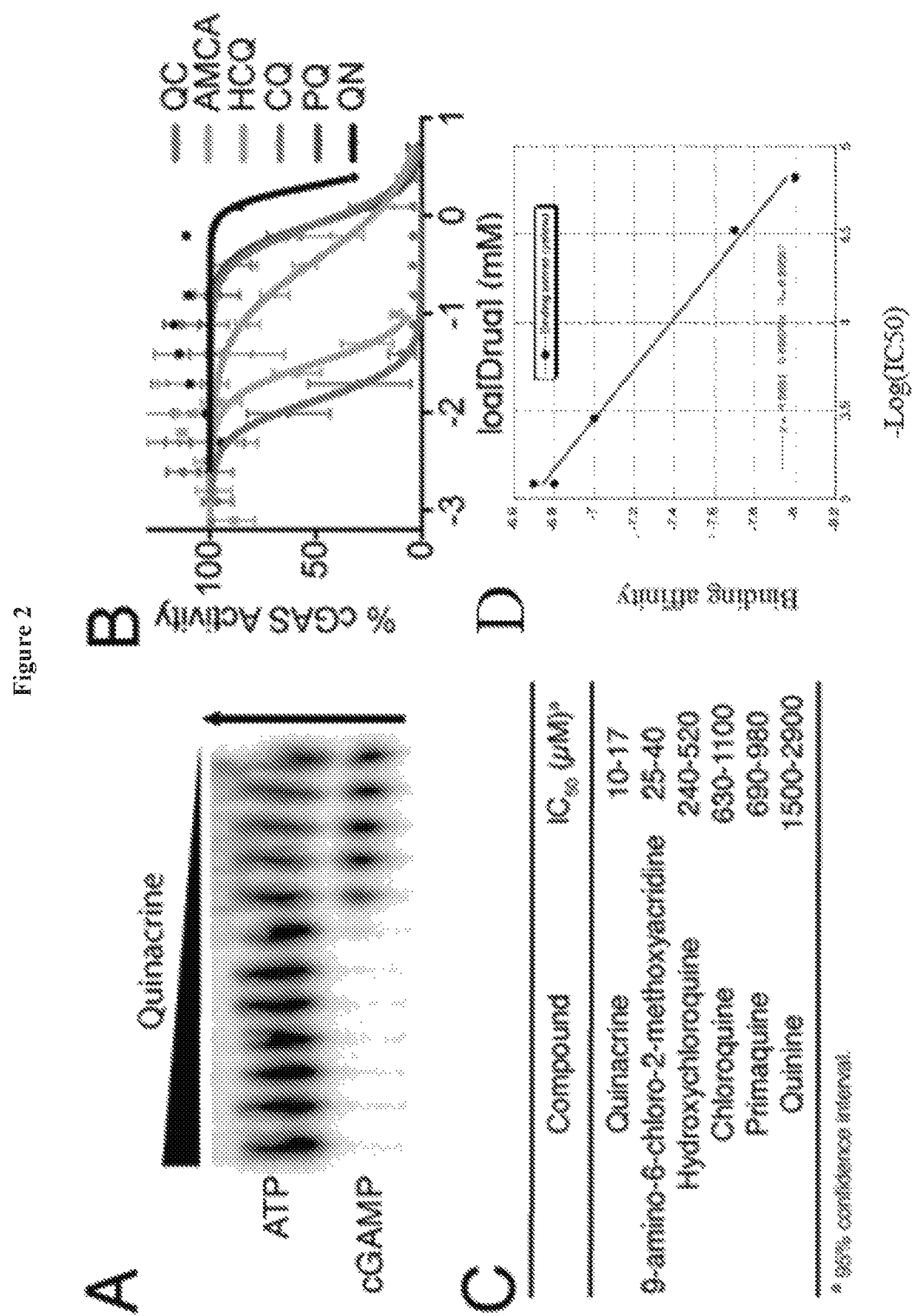
FIG. 2 is (A) A representative TLC analysis of Quinacrine inhibition of cGAS turnover; (B) Quantification of cGAS inhibition by HCQ derivatives; (C) summary of the 95% confidence intervals for the $IC_{50}$ of each associated inhibitor; and (D) binding affinity correlated with $-\log(IC_{50})$.

HCQ belongs to a family of antimalarial drugs that share the structure of aminoquinolines. To rapidly screen these antimalarial drugs for their ability to interfere with cGAS activation by ds-DNA, we performed dose titration experiments with drug and quantified cGAMP production using thin layer chromatography (TLC) (FIG. 2A). Reactions were performed in triplicate and normalized to no-inhibitor controls and fit by non-linear regression using Prism GRAPHPAD™ to determine the $IC_{50}$ of each compound. Each compound yielded dose-response curves similar to HCQ but with different inhibitory activities (FIG. 2B). From these curves, we estimated the concentration of the test compound required for half maximal blockade of cGAS activity ($IC_{50}$, 50% inhibition coefficient). As shown in FIG. 2C, Quinacrine and ACMA were relatively potent inhibitors of cGAMP production; Primaquine and Quinine had very low inhibitory activity and both HCQ and Chloroquine had intermediate inhibitory activities. Strikingly, the computational predicted binding affinities of these anti-malaria drugs inversely correlated with the $IC_{50}$ of anti-malarial drugs, validating the prediction of our computational analysis (FIG. 2D).

Figure 4:
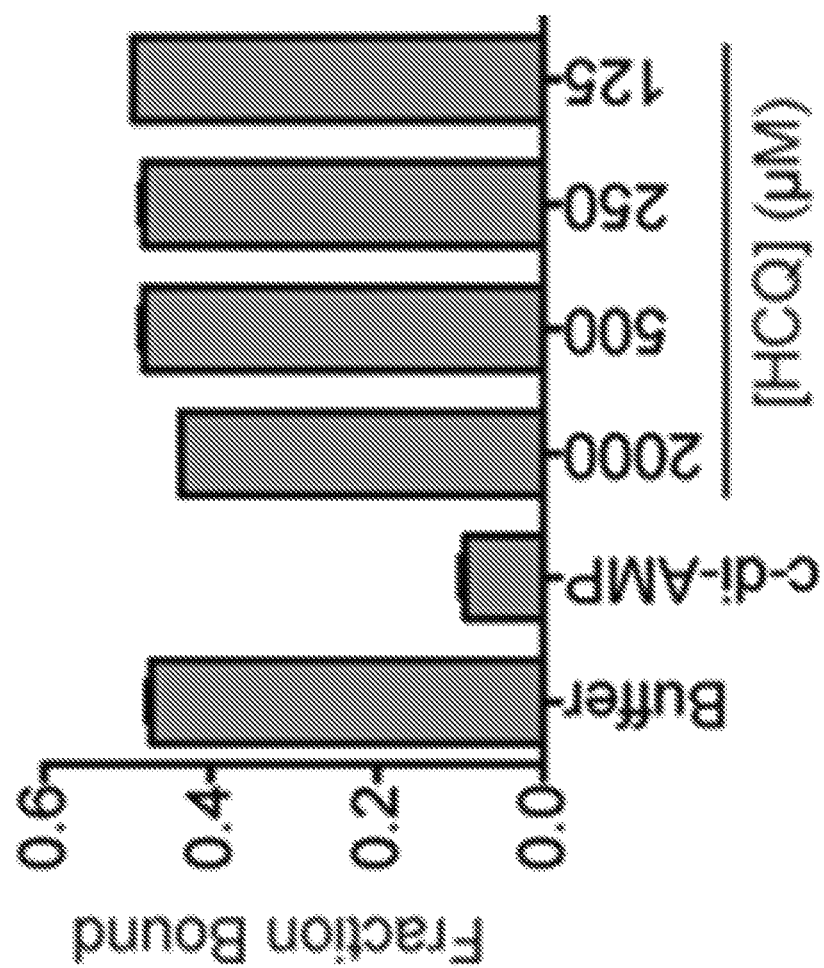
FIG. 4 shows the binding of 32P-c-di-AMP (2 nM) by STING (170 μM) monitored in the presence of unlabeled c-di-AMP (200 μM) and HCQ with different concentrations.

To test whether HCQ specifically inhibit cGAS activity but not STING activity, we incubated isotope labelled c-di-AMP with STING and then added un-labelled c-di-AMP or different concentration of HCQ. Our results demonstrated that HCQ could specifically block dsDNA binding to cGAS but not c-di-AMP to STING (FIG. 4).

Antimalarial Drugs could Inhibit IFNb Expression

Figure 3:
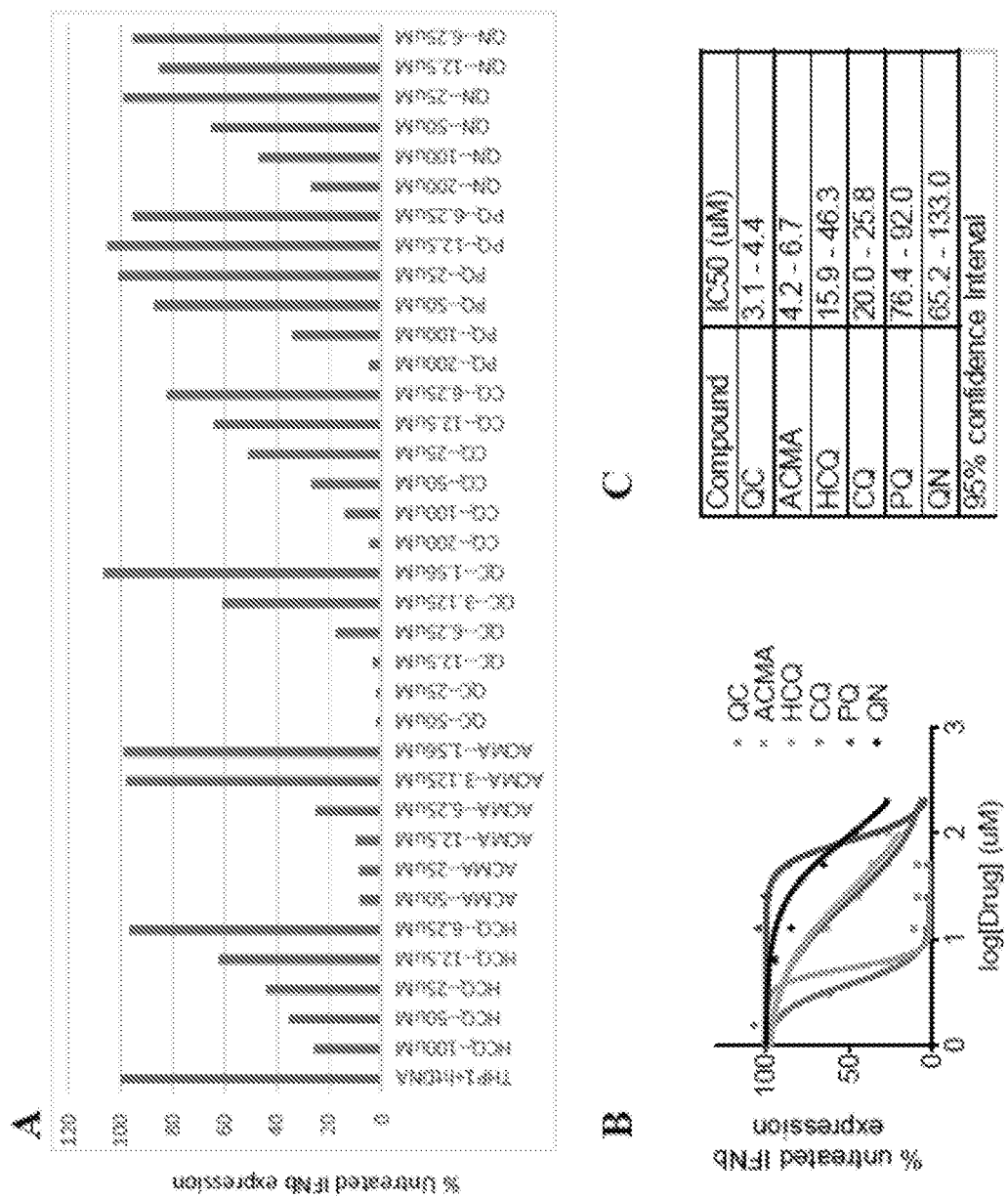
FIG. 3 shows (A) the inhibition of the IFNb induction with antimalarial drugs; and (B and C) the different capability of antimalarial drugs to inhibit IFNb production as shown by inhibition curves and $IC_{50}$.

Systemic Lupus Erythematosus (SLE) is strongly associated with increased expression of type I interferon (IFN-I) (Elkon, 2012). Both genetic as well as experimental studies indicate that IFN-I plays a central role in this disease (Lovgren, 2006) (Niewold, 2007). To determine the physiological relevance of our computational analysis and in vitro observance, we examined whether antimalarial drugs could inhibit IFNb production within the cell. As previously demonstrated by Sun and Wu et al (Sun, 2013) (Wu, 2013), cGAS is the cytosolic DNA sensor required for the IFNb production in THP1 cells transfected with herring testis DNA. Using this approach, we transfected THP1 cells with DNA in the presence or absence of antimalarial compounds and quantified IFNb expression by QPCR. As shown in FIG. 3. Quinacrine, AMCA, HCQ and Chloroquine all inhibited IFNb production by THP1 cells with an $IC_{50}$ dose range of 3-25 μM. In contrast primaquine and Quinine were less effective by about one log order IFNb (FIGS. 3A and 3B). Of note, the rank order of antimalarials in vitro and in vivo was virtually identical validating the DNA/cGAS interaction as the target (compare FIG. 2B and FIG. 3B).

To rule out whether antimalarial drugs inhibited IFNb production by interfering with transfection efficiency, we performed two experiments. First, we compared DNA transfection efficiency in the presence or absence of antimalarial. In the second experiment, we preincubated THP1 cells with antimalarial, washed the drug away and then evaluated the ability of transfected drug to stimulate IFNb.

PolyIC was transfected by Lipofectamine to THP1 cells with different concentration of HCQ. The IL-1b cytokine production was measured by ELISA and the results indicated HCQ did not interfere with the Lipofectamine transfection efficiency (Supplemental FIG. 3).

The results demonstrated that some of antimalarial drugs could strongly block the interaction of DNA and cGAS and thus inhibit the IFNb production, which is a novel mechanism of antimalarial drugs' inhibition of type I IFN production.

Materials and Methods
Computational Analysis cGAS inhibitors were screened based on the crystal structure of the cGAS and docking of compounds predicted in silico. In silico, structure-based drug screening were provided by AutoDock VINA™ and DOCK™.

cGAS Expression and Purification

Protein was expressed in Rosetta BL21 pLysS cells. 4.5 L of bacterial culture was induced at $OD_{600}$=0.5 with 500 µM IPTG and at 18° C. for 20 hrs. Cells were lysed into 50 mM Tris-HCl, pH=8, 300 mM NaCl, 20 mM Imidazole, 5 mM BME and 0.2 mM PMSF by sonication. Cleared lysate was incubated with Ni-NTA, washed with 50 mL of Lysis buffer and eluted with 20 mM Tris-Cl, pH=7.4, 300 mM NaCl, 500 mM Imidazole. Protein was subsequently diluted to 200 mM NaCl and bound to a Heparin SEPHAROSE™ column (GE Healthcare). The column was washed with 2 column volumes of 250 mM NaCl, 20 mM Tris, 1 mM DTT, pH 7.4 and developed with a gradient from 250-1000 mM NaCl. The major peak of cGAS was finally purified using an S200 SUPERDEX™ (GE Healthcare) size exclusion column with 20 mM Tris pH 7.5, 250 mM NaCl and 1 mM DTT running buffer. Protein was ~95% pure by Coomassie stained SDS-PAGE gel.

cGAS Activity Assays

Figure 7:
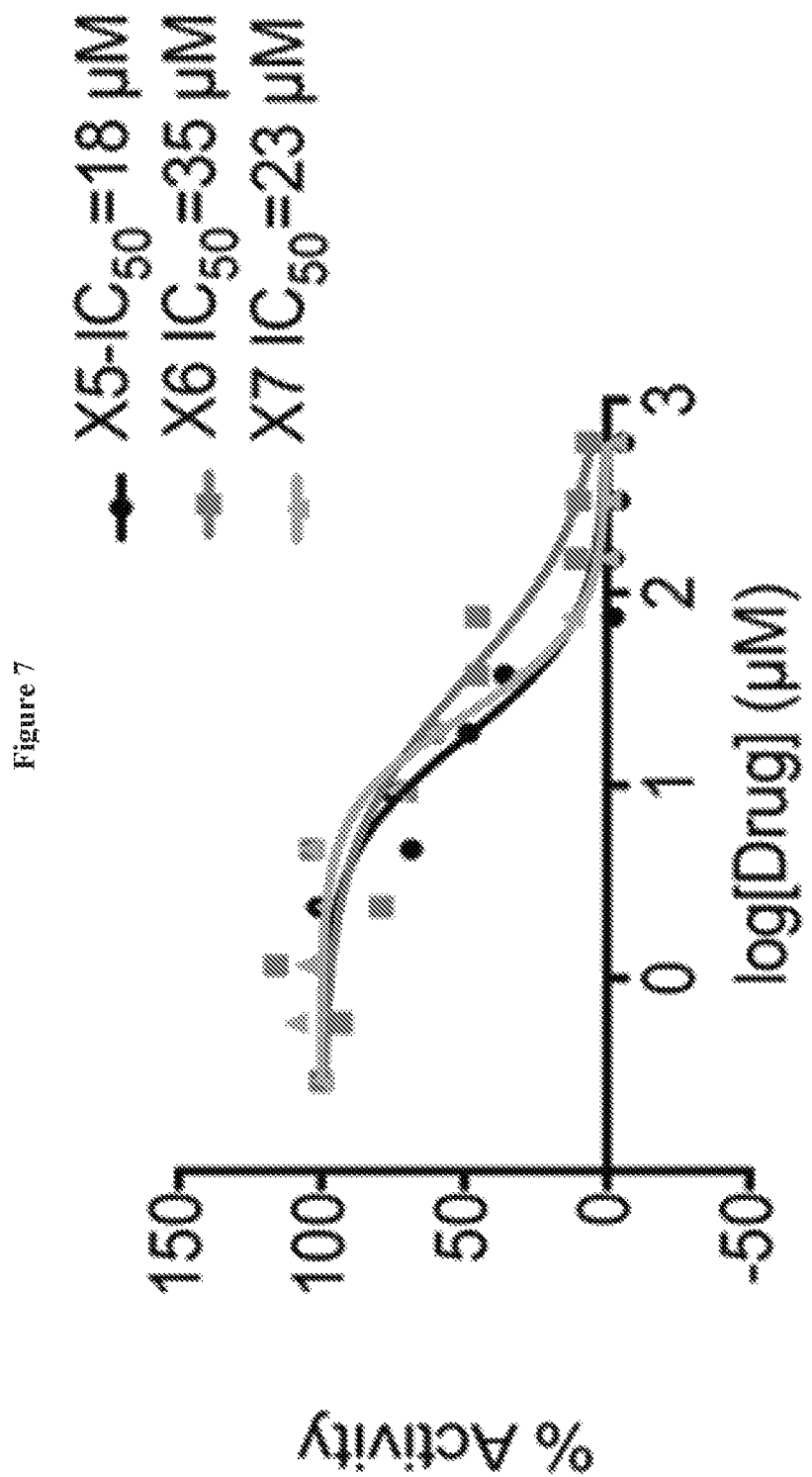
FIG. 7 shows cGAS activity of compounds X5, X6 and X7 by in vitro biochemical assay.

Initial characterization of enzyme activity was monitored in the presence of 250 µM ATP, 250 µM GTP, 0-500 µg/mL herring testes DNA, 1.4 µM cGAS, 3.3 nM $^{32}$P-γ-ATP in a buffer composed of 40 mM Tris, 250 mM NaCl, 10 mM MgCl2, pH 7.5. Reactions were incubated for 1 hr at room temperature and subsequently spotted on PEI-cellulose TLC plates and developed using a solvent composition 1:1.5 [v/v] saturated NH4SO4 and 1.5 M KH2PO4 [pH 3.6]. For inhibition assays, compounds were characterized in the presence of the above reaction contents at fixed 100 µg/mL htDNA. TLC plates were exposed to a phosphor-storage screen and imaged using a TYPHOON™ imaging system. (See FIGS. 7-16).

cGAS activity was monitored in the presence of 250 µM ATP, 250 µM GTP, 0-500 µg/ml herring testes DNA. 1.4 µM cGAS. and 3.3 nM [$^{32}$P]-ATP in Tris buffer (pH 7.5). After incubation for 1 h at room temperature, samples were spotted on PEI-cellulose Thin Layer Chromatograph (TLC) plates, and developed using a solvent composed of 1:1.5 [v/v] saturated $NH_4SO_4$ and 1.5 M $KH_2PO_4$ [pH 3.6]. For inhibition assays, compounds were characterized in the presence of the above reaction contents at fixed 100 µg/ml HT DNA. TLC plates were exposed to a phosphor-storage screen and imaged using a TYPHOOON™ imaging system. (FIG. 7).

Thin Layer Chromatograph (TLC) assay was used for the quantification of cGAS inhibition by compounds X5/X6/X7. Reactions were normalized to no-inhibitor controls and fit by non-linear regression using Prizm GRAPHPAD™ to determine the $IC_{50}$ of each compound. (FIG. 7).

Figure 8:
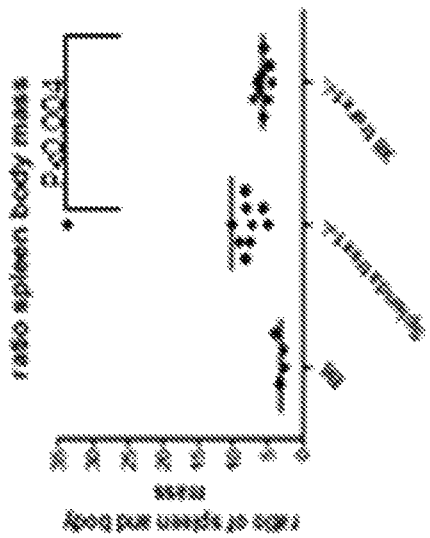
FIG. 8 shows the effect of compound X6 on spleen mass in TREX1 KO mouse.
Figure 8:
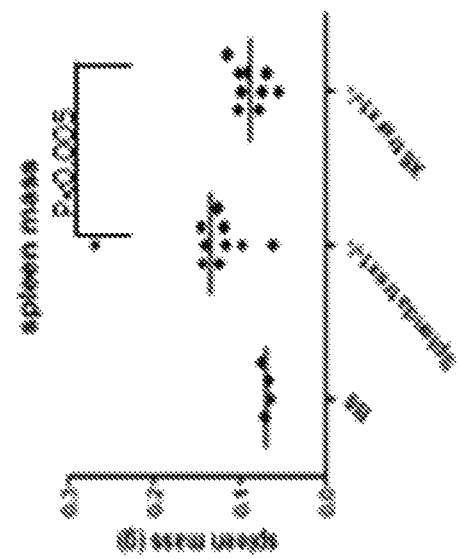
Figure 8:
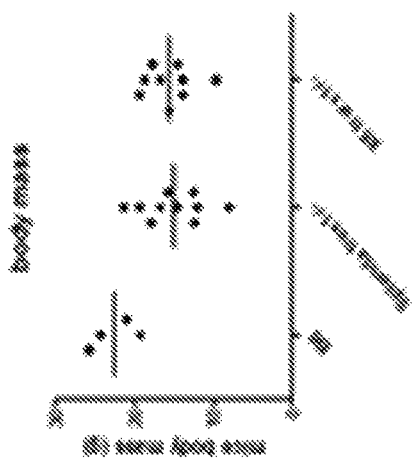

Trex1−/− mouse were treated with 25 mg/kg/day compound X6 dissolved in water with SPLENDA™ or water with SPLENDA™ only as control for 8 weeks from birth. At 8 weeks age, mice were sacrificed and spleens were harvested. Mouse body mass and spleen mass were measured by balance. Statistical analysis was performed with a two-tailed, unpaired Student's t test. (FIG. 8).

Figure 9:
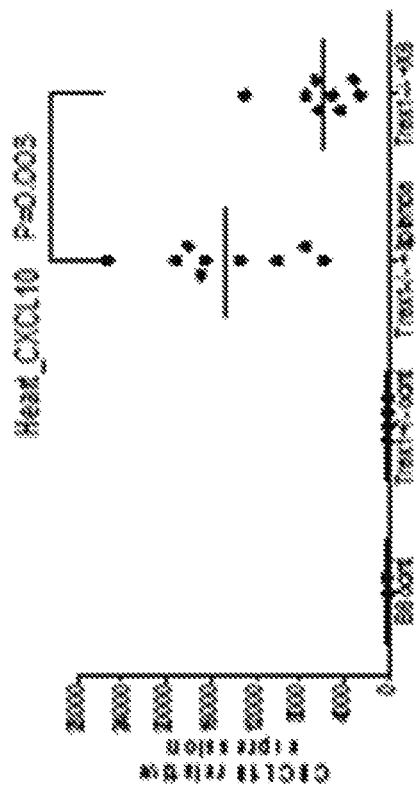
FIG. 9 shows the effect of compound X6 on the expression of ISG15 and CXCL10 in TREX1 KO mouse heart.
Figure 9:
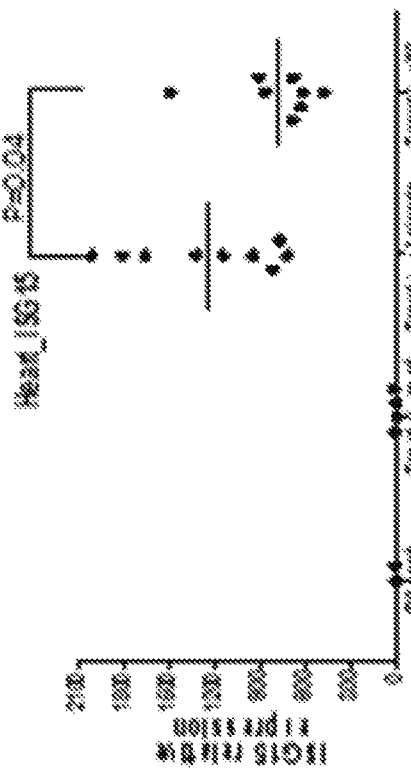
Figure 10:
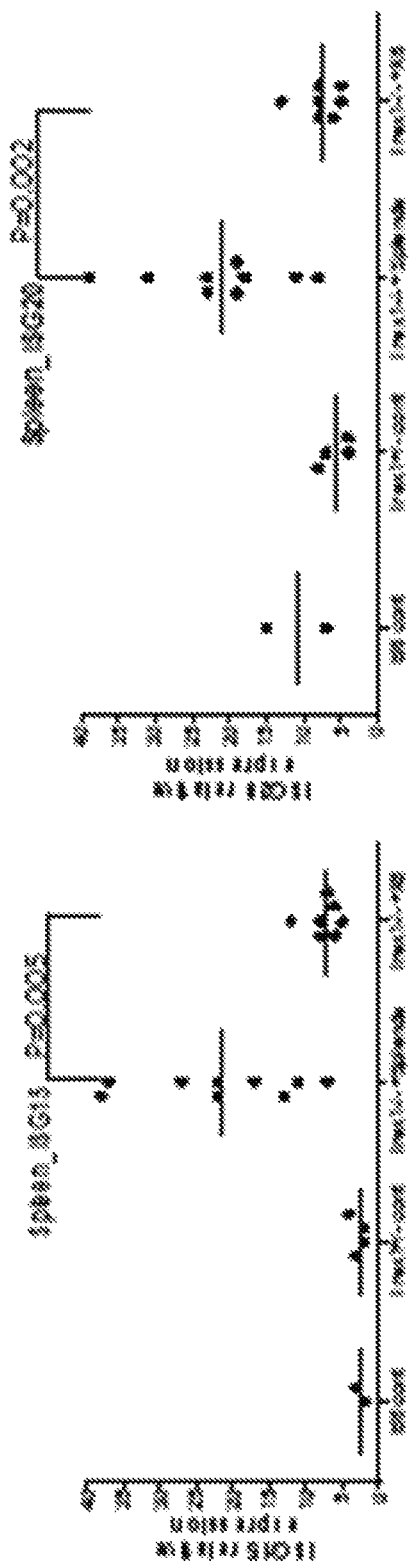
FIG. 10 shows the effect of compound X6 on the expression of ISG15 and ISG20 in TREX1 KO mouse spleen.
Figure 11:
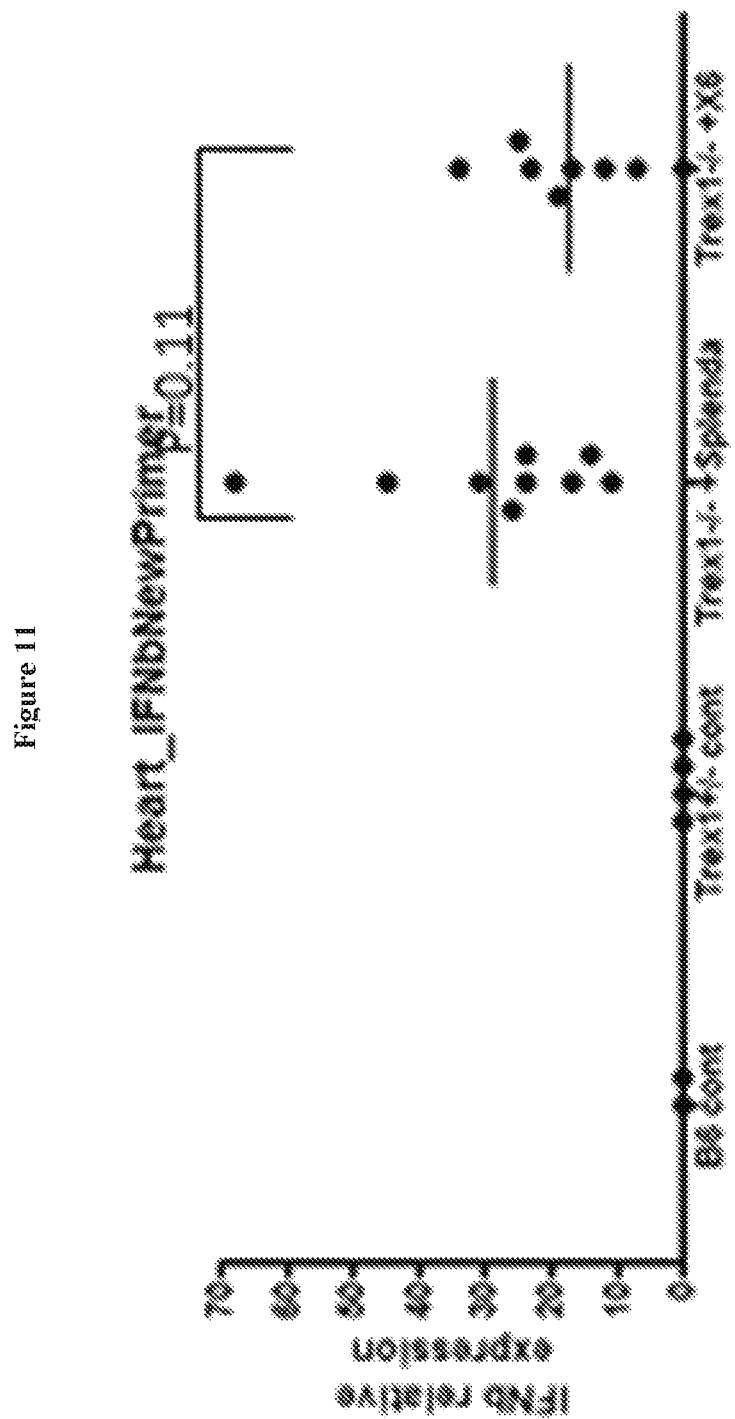
FIG. 11 shows the effect of compound X6 on the expression of IFNb in TREX1 KO mouse heart.

Total RNA was isolated from heart or spleen tissues using the RNeasy mini kit with a DNASE™ treatment step (Qiagen, Valencia, Calif.). cDNA was generated using 300 ng RNA with the high-capacity cDNA RT-KIT™ using random primers (Applied Biosystems, Foster City, Calif.). Reactions in duplicate were run on an ABI ONESTEP PLUS™ using the different gene specific primers. A two-stage cycle of 95° C. for 15 s and 60° C. for 1 min was repeated for 40 cycles followed by a dissociation stage. Threshold cycle values were set as a constant threshold at 0.2, and fold changes in gene expression were then calculated using the $2^{-\Delta\Delta CT}$ method. (FIGS. 9, 10 and 11).

Heart were harvested when the mouse were sacrificed after 8 weeks treatment. RNA was isolated from heat tissues with RNEAST MINIKIT™ and cDNA was synthesized with the high-capacity cDNA RT-KIT™ using random primers. ISG15 and CXCL10 mRNA expression was normalized to the 18S mRNA. Horizontal bars represent the mean values. Statistical analysis was performed with a two-tailed, unpaired Student's t test. (FIG. 9).

Spleen were harvested when the mouse were sacrificed after 8 weeks treatment. Spleen ISG15 and ISG20 mRNA expression was analyzed by qPCR and the results expressed relative to the 18S mRNA. Horizontal bars represent the mean values. Mean data was compared using a t test. (FIG. 10).

Heart were harvested when the mouse were sacrificed after 8 weeks treatment. Heart IFNb mRNA expression was analyzed by qPCR and the results expressed relative to the 18S mRNA. Horizontal bars represent the mean values. Mean data was compared using a t test. (FIG. 11).

Figure 12:
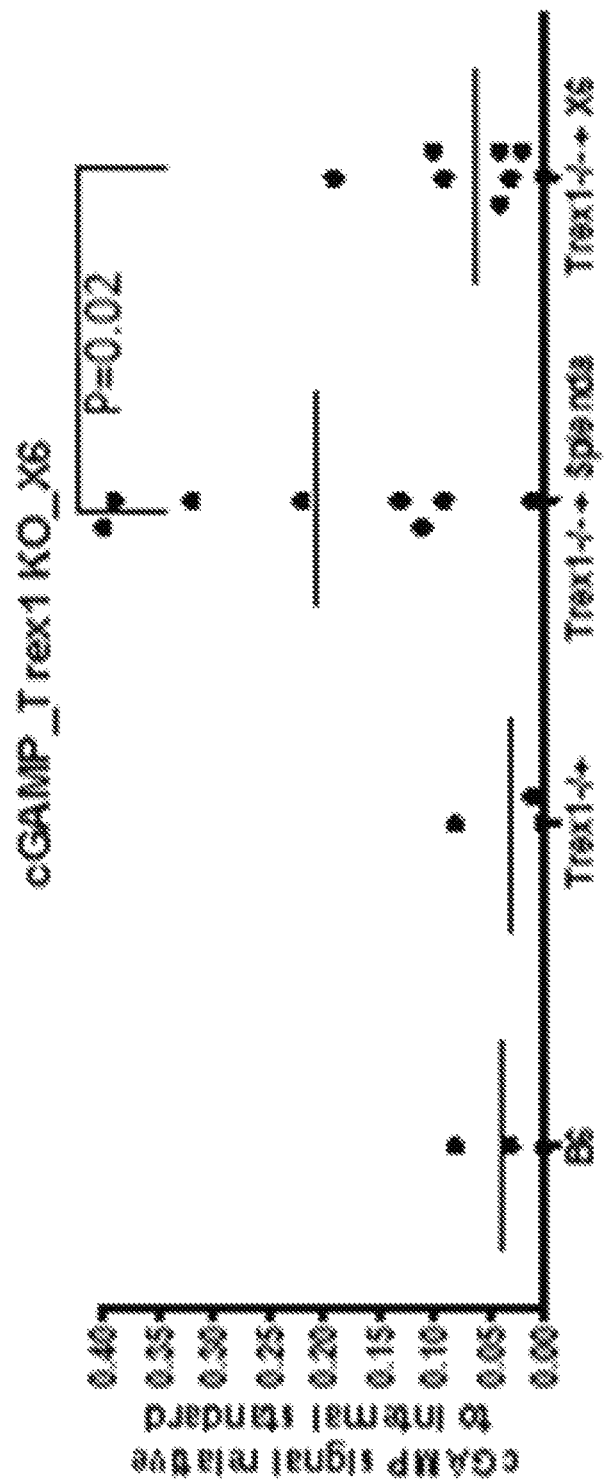
FIG. 12 shows the effect of compound X6 on Trex1-/- KO mouse cGAMP expression compared to SPLENDA™ treatment.

Heart tissues were lysed with 80% MeOH spiked with 5 nM heavy isotope-labeled cGAMP (cGAMP*), containing $^{13}$C, $^{15}$N-perlabeled AMP, as internal standard. Tissues extracts were sonicated on ice for 1 min with 20% duty cycle and 1 output settings. Tissue debris was pelleted at 14,000 rpm for 10 minutes. Methanol extraction solution was transferred to a new tube and evaporated using a speed vac. cGAMP was further purified by Solid phase extraction column (OASIS WAX™ column from Waters) and re-suspended in 50 ul OPTIMA LC/MS™ water (Thermal Scientific, Odessa, Tex.) for Mass Spec analysis. For targeted detection of cGAMP, a Multiple Reaction Monitoring (MRM) assay was developed on Waters XEVO TQS™ Mass Spectrometer coupled with Ultra-Performance Liquid Chromatogram (UPLC). In the assay, two transitions of each target ion were monitored: cGAMP, +675.1/152.1 (parent ion/daughter ion) and +675.1/136.0; cGAMP*, +690.0/152.1 and +690.0/146.0. (FIG. 12)

cGAMP was isolated from mouse heart tissues by a methanol extraction procedure. The abundance of cGAMP was quantitated by mass spectrometry using multiple reaction monitoring (MRM). Heavy isotope-labeled cGAMP was spiked into each sample as an internal standard and the mass spectrum of the internal standard was used to determine the peak of the endogenous cGAMP. cGAMP signal peak area was normalized to Heavy isotope labelled cGAMP internal standards peak area. Mean data was compared using a t test. (FIG. 12).

Figure 13:
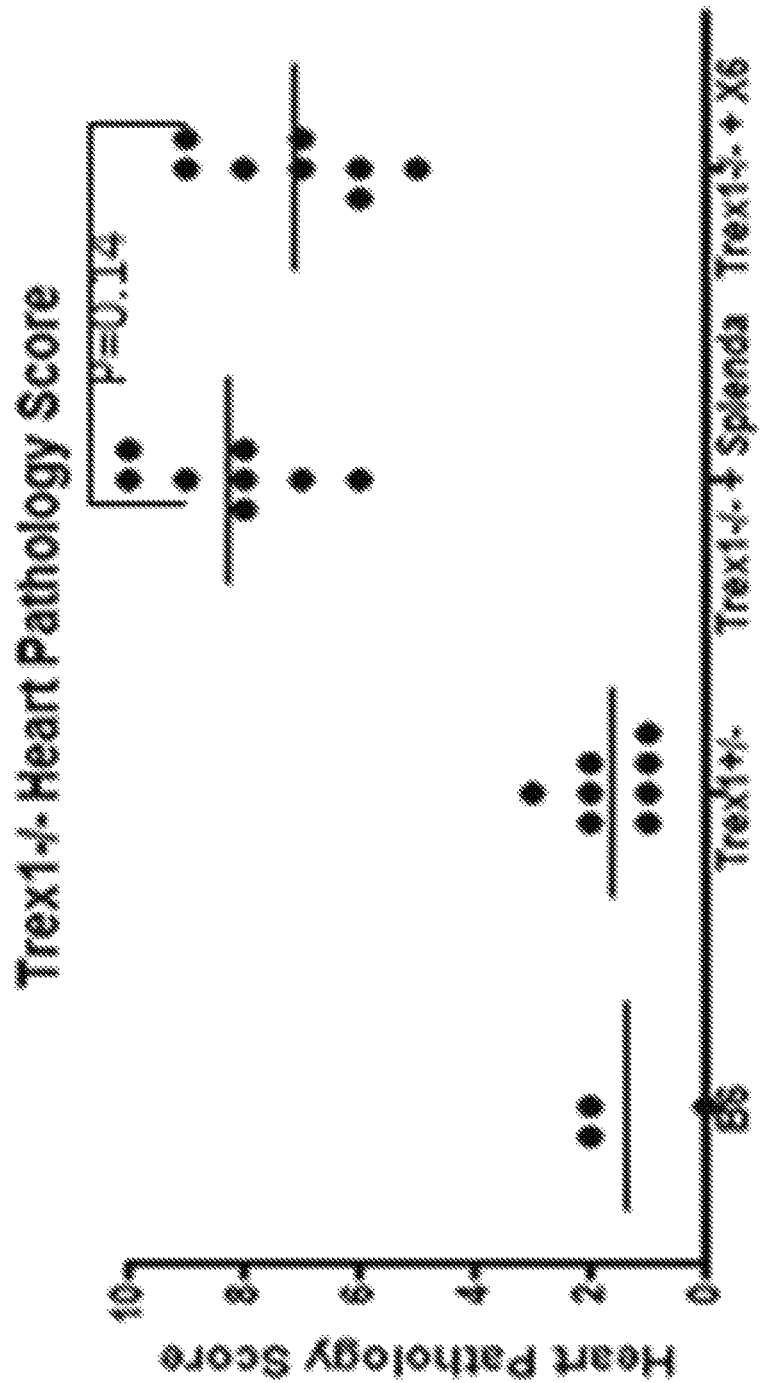
FIG. 13 shows the Trex1-/- Heart Pathology total score for compound X6.

Method for Pathology (FIG. 13, 14, 15, 16)

Trex1−/− mouse were treated with 25 mg/kg/day compound X6 dissolved in water with SPLENDA™ or water with SPLENDA™ only as control for 8 weeks from birth. At 8 weeks age, mice were sacrificed and heart tissues were harvested. Tissues were fixed in Formalin, paraffin embedded, cut into 5 um sections, and stained with hematoxylin and eosin. All tissues were coded to remove genotype identification and were evaluated for evidence of inflammation and fibrosis. Numerical scores were assigned based on degree of severity (0=normal to 5=most severe). The sum of individual scores from Endocardial Inflammation, Fibrosis and Myocardial inflammation was used to obtain a total tissue histological score. Scoring criteria for each tissue:

Endocardial Inflammation Score:
0=normal; 1=few inflammatory cells; 2=multifocal clusters≤5; 3=multifocal clusters≤10; 4=coalescing foci≥10; 5=coalescing to diffuse foci Myocardial Inflammation:
0=normal; 1=few (1-3 cells); 2=multifocal foci (3-5) with degenerative changes; 3=multifocal foci (3-5) with necrotic changes; 4=≥10 coalescing foci Endocardial Fibrosis:
0=normal; 1=few inflammatory cells; 2=multifocal clusters≤5, 3=multifocal clusters≤10; 4=coalescing foci≥10; 5=coalescing to diffuse foci Blinded analysis of heart tissues from Trex1−/− mouse treated with compound X6 or SPLENDA™. Data are represented as total histological scores from individual animals as a sum of the scores from Endocardial Inflammation, Endocardial Fibrosis and Myocardial changes. Horizontal bars represent the mean values. Statistical analysis was performed with a two-tailed, unpaired Student's t test. (FIG. 13).

Figure 14:
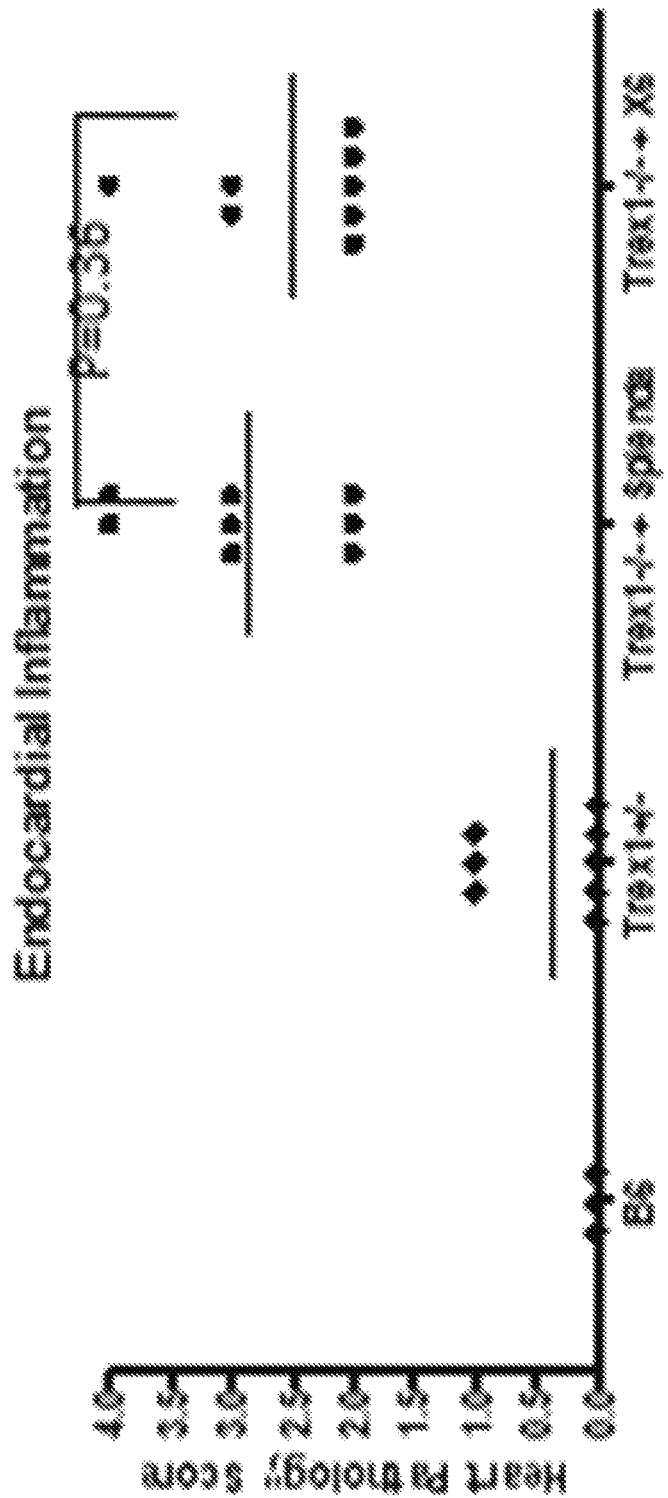
FIG. 14 shows the effect of compound X6 on Trex1-/- heart endocardial inflammation.

Blinded analysis of heart tissues from Trex1−/− mouse treated with compound X6 or SPLENDA™. Data are represented as histological scores from individual animals for Endocardial Inflammation. Horizontal bars represent the mean values. Statistical analysis was performed with a two-tailed, unpaired Student's t test. (FIG. 14).

Figure 15:
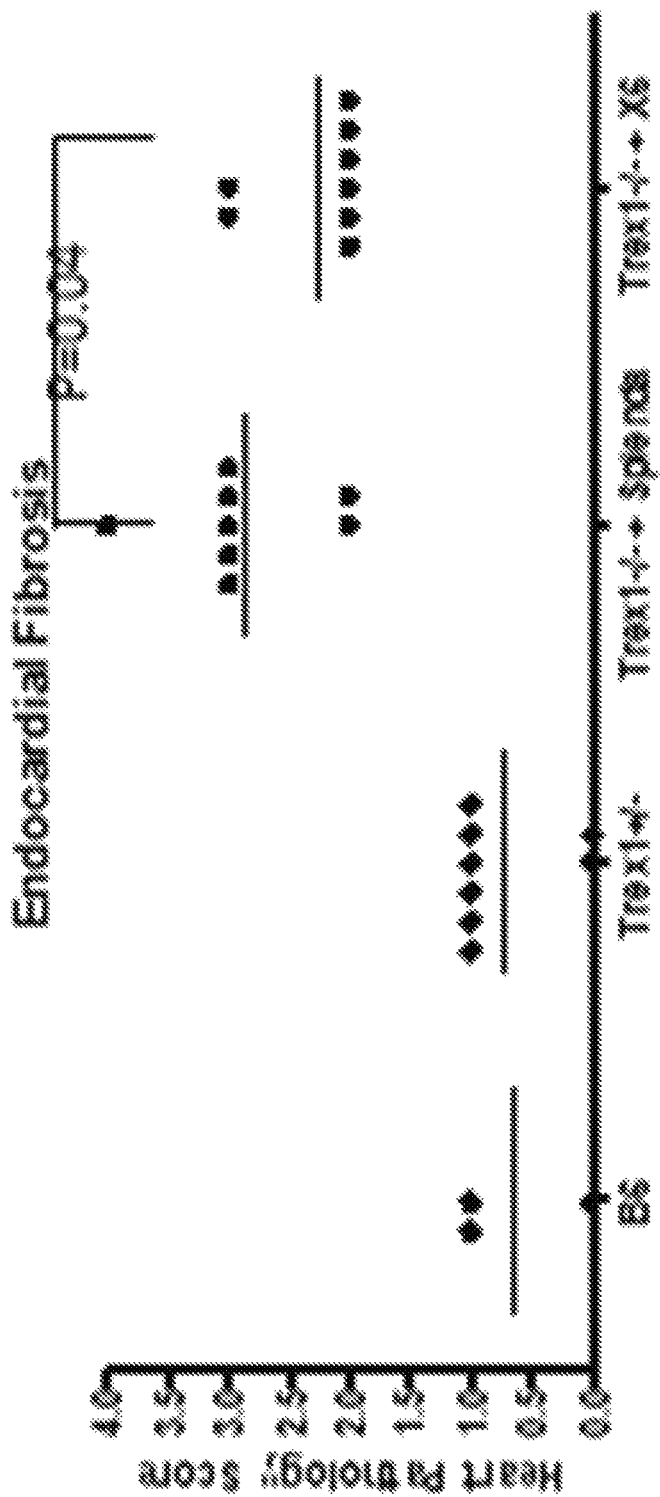
FIG. 15 shows the effect of compound X6 on Trex1-/- heart endocardial fibrosis.

Blinded analysis of heart tissues from Trex1−/− mouse treated with compound X6 or SPLENDA™. Data are represented as histological scores from individual animals for Endocardial Inflammation. Horizontal bars represent the mean values. Statistical analysis was performed with a two-tailed, unpaired Student's t test. (FIG. 15).

Figure 16:
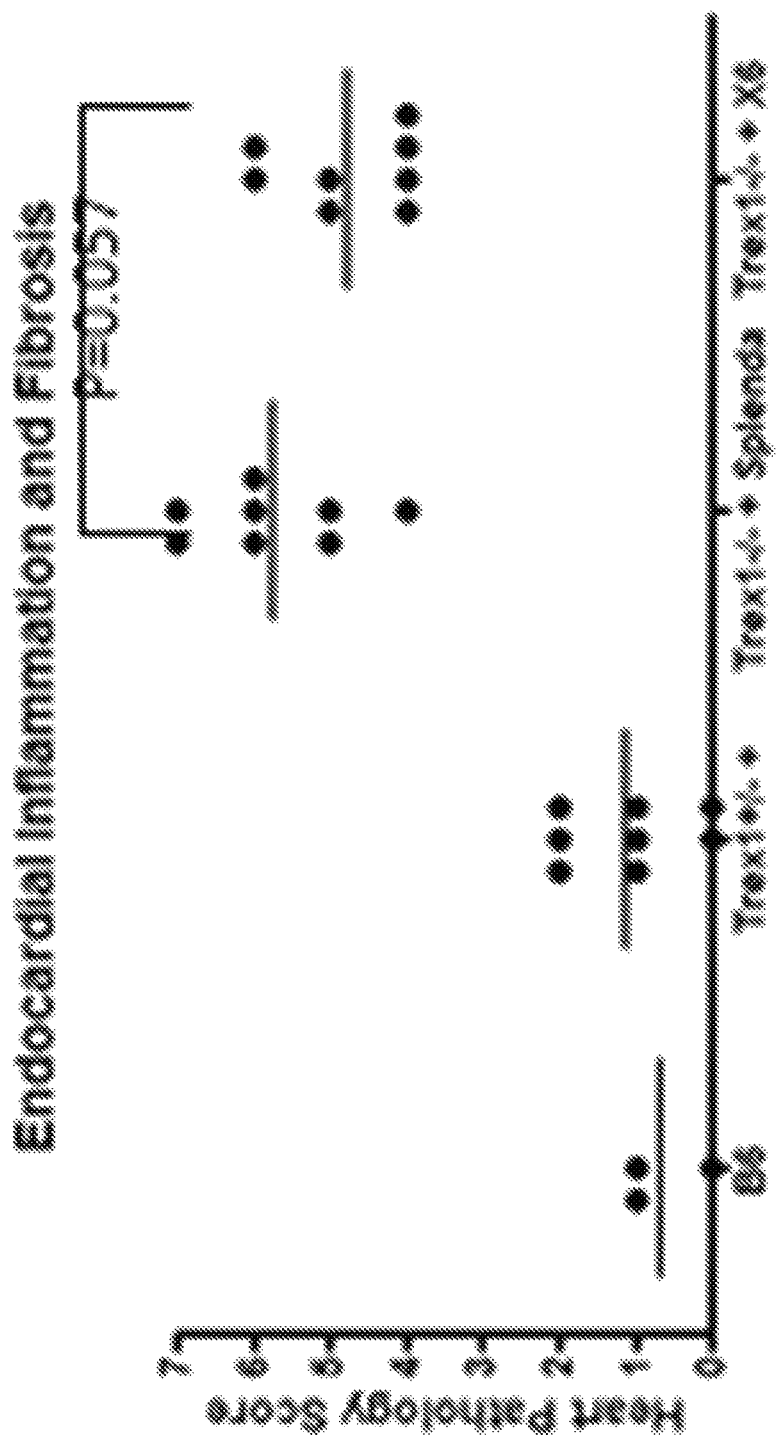
FIG. 16 shows the effect of compound X6 on Trex1-/- Heart endocardial inflammation/fibrosis.

Blinded analysis of heart tissues from Trex1−/− mouse treated with compound X6 or SPLENDA™. Data are represented as combined histological scores from individual animals as a sum of the scores from Endocardial Inflammation and Fibrosis. Horizontal bars represent the mean values. Statistical analysis was performed with a two-tailed, unpaired Student's t test. (FIG. 16)

Electrophoretic Mobility Shift Assays (EMSA)

Electrophoretic mobility shift assay (EMSAs) were performed to measure the DNA-binding ability with or without HCQ in vitro. For the DNA binding studies, 0.2 µM of the 100 bp annealed double stranded interferon stimulatory DNA (ISD) (Forward: 5'-ACATCTAGTACAT-GTCTAGTCAGTATCTAGTGATTATCTAGACATA-CATCTAGTA CATGTCTAGTCAGTATCTAGTGAT-TATCTAGACATGGACTCATCC-3', Backward 5'-GGATGAGTCCATGTCTAGATAATCACTAGATACT-GACTAGACATGTACTAGATGT ATGTCTAGATAAT-CACTAGATACTGACTAGACATGTACTAGATGT-3') were mixed 1.5 µM cGAS protein and different concentration of HCQ (0.075~5 mM) and incubated in RT for 2 hours. The mixtures were resolved on 1% agarose gel using 1×TBE electrophoresis buffer of at constant voltage of 100 V. The gel was analyzed by using a fluorescence-based EMSA kit (Molecular Probes) according to the manufacturer's protocol. Gels stained with fluorescent dyes were visualized by a Gel Doc XR™ (Bio-Rad).

THP1 Cell Stimulation and IFNb Expression Inhibition

THP1 cells ($0.2 \times 10^6$) were transfected with 0.5 ug herring testis DNA using Lipofectamine 2000 (Invitrogen) according to the manufacture's instruction. Before transfection, THP1 cells were incubated with different concentration of Hydroxychloroquine or other antimalarial drugs (100, 50, 25, 12.5 µM) for 5 minutes. Cells were stimulated for 16 hours and then harvested for RNA extraction.

RNA Preparation and Quantitative Real-time PCR

Total RNA was isolated from THP1 cells using the RNeasy mini kit (Qiagen, Valencia, Calif.). cDNA was synthesized using 100 ng RNA with the high-capacity cDNA RT-KIT™ using random primers (Applied Biosystems, Foster City, Calif.). Reactions in duplicate were run on an ABI STEPONE PLUS™ using the primers from Qiagen (primer catalog number): a two-stage cycle of 95° C. for 15 s and 60° C. for 1 min was repeated for 40 cycles followed by a dissociation stage. Threshold cycle values were set as a constant threshold at 0.2, and fold changes in gene expression were then calculated using the $2^{-\Delta\Delta C_T}$ method.

Example 2

The Second Messenger, cGAMP, and the Enzyme, cGAS, are Expressed in Systemic Lupus Erythematosus To determine whether the cGAS pathway could contribute to IFN production in SLE, cGAS expression was quantified by QPCR from RNA obtained from 51 SLE and 20 Normal Control peripheral blood mononuclear cells (PBMC). These studies revealed that SLE patients had a significant increase in the expression of cGAS (P=0.0045). cGAS expression positively correlated with ISG expression and IFN score in SLE patients consistent with it being an IFN signature gene.

To determine whether downstream pathways of cGAS were activated in SLE cells, IRF3 activation was quantified by phosphorylation in PBMC. IRF3 was activated in a higher proportion of SLE patients compared to controls. These findings suggest that the cGAS pathway appears active in SLE patients and likely contributes to IFN stimulation regardless of whether upregulation of cGAS is an initiator of IFN-I stimulation or is a consequence of IFN-I stimulation. To quantify c-GAMP in patient samples we have obtained cyclic GMP-AMP dinucleotide that is comprised of the unusual 2'-5' and 3'-5' phosphodiester linkage and have been able to distinguish the cyclic dinucleotide from other species by High Performance Liquid Chromatography-tandem Mass Spectrometry (HPLC-MS/MS). cGAMP is expressed in approximately one third of SLE patients with higher anti-DNA antibody titer. Experiments were conducted to determine whether cGAS and cGAMP can be used as a biomarker of SLE activity that correlates with disease activity, duration or severity. AutoDock VINA™ was used to identify several drugs including Hydroxychloroquine that interacts at the Zn thumb and spine regions of cGAS involving simultaneous protein and DNA binding. EMSA analysis shows that HCQ inhibits the DNA binding to cGAS, which suggests a possible mechanism of HCQ action through the interruption of dsDNA stimulated cGAS enzyme activation besides the HCQ inhibition of lysosome acidification.

IFN-β can be produced by almost any cell following stimulation by (viral or bacterial) nucleic acids. Release of this cytokine serves to prime or amplify type I IFN by other cells. especially plasmacytoid dendritic cells (pDCs) that are the main producers of IFN-α. Over the last decade, there have been major advances in the understanding of the role of intracellular sensors such as Toll Like Receptors (TLRs), RIG-I like receptors (RLRs) and Aim-like receptors (ALRs) that respond to nucleic acid ligands by stimulating production of IFN-I and other inflammatory cytokines (Takeuchi, O. and S. Akira, *Pattern recognition receptors and inflammation*. Cell, 2010. 140(6): p. 805-20). Cyclic di-nucleotides were discovered in bacteria more than 25 years ago and are known to function as ubiquitous second messenger molecules that regulate motility, biofilm formation, and virulence. Recently, it was reported that cyclic di-AMP (c-di-AMP) produced by bacteria could stimulate the production of IFN-I by the cytosolic surveillance pathway (CSP) (Woodward, J. J., A. T. Iavarone, and D. A. Portnoy, *c-di-AMP secreted by intracellular Listeria monocytogenes activates a host type I interferon response*. Science, 2010. 328(5986): p. 1703-5). Further dissection of the pathway revealed that c-di-GMP bound to and activated the adaptor, STING (Burdette, D. L., et al., *STING is a direct innate immune sensor of cyclic di-GMP*. Nature, 2011. 478(7370): p. 515-8) which was previously identified as a DNA sensor in the CSP resulting in the stimulation of IFN-b. More recently, Chen et al (Wu, J., et al., *Cyclic GMP-AMP is an endogenous second messenger in innate immune signaling by cytosolic DNA*. Science, 2013. 339(6121): p. 826-30) discovered that a cyclic GMP-AMP (cGAMP) was produced in metazoans and that it also stimulated IFN-I in mammalian cells. In brief, ds-DNA binds to a positively charged pocket of the enzyme, cyclic GAMP synthase (cGAS) (Sun, L., et al., *Cyclic GMP-AMP synthase is a cytosolic DNA sensor that activates the type I interferon pathway*. Science, 2013. 339(6121): p. 786-91). This binding results in a conformational change and opening of a catalytic cleft resulting in the synthesis of the noncanonical cyclic dinucleotide, cyclic GMP-AMP (cGAMP) containing an unusual [G(2'-5')pA(3'-5')p] linkage (Diner, E. J., et al., *The Innate Immune DNA Sensor cGAS Produces a Noncanonical Cyclic Dinucleotide that Activates Human STING*. Cell Rep. 2013. 3(5): p. 1355-61) cGAMP binds to the adaptor protein, STING, which triggers activation of TBK. IRF3 and IFN-b (Sun, 2013). Our goal was to determine whether the second messenger, cGAMP, plays a role in the disease SLE that is characterized by an IFN signature.

Increased Expression of cGAS and pIRF3 in a Proportion of SLE Patients

Figure 5:
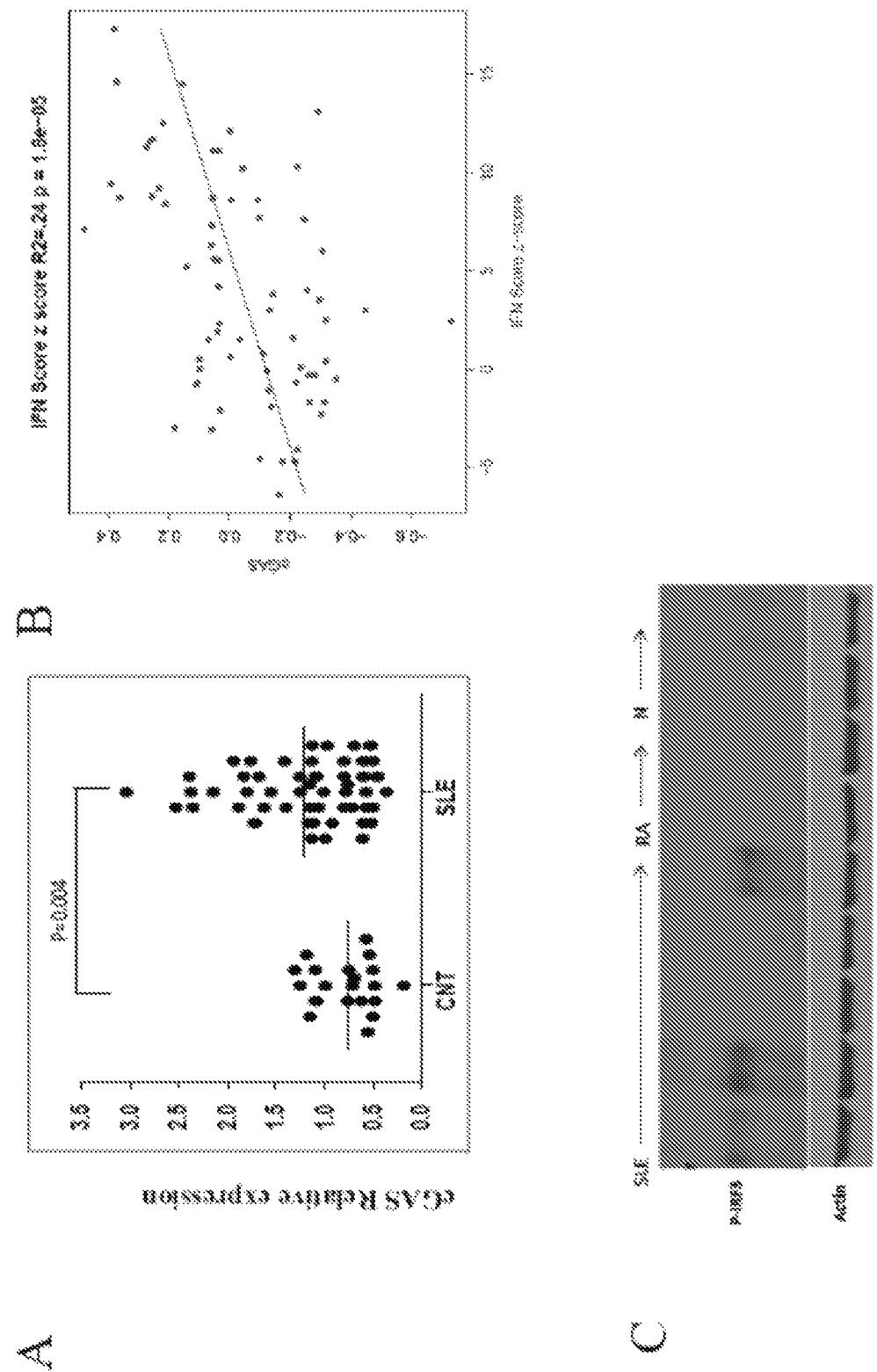
FIG. 5 is (A) QPCR analysis of cGAS expression from healthy controls (CNT, n=20) and SLE (n=51); (B) cGAS expression correlated with IFN score in SLE patients; and (C) Western blot assay for the phosphorylated IRF3 expression.

QPCR analysis of cGAS expression from healthy controls (CNT, n=20) and SLE (n=51). Samples were normalized for expression of 18S ribosomal RNA. A highly statistically significant difference in expression was observed between SLE patients and controls. cGAS expression correlated well with IFN score in SLE patients (FIG. 5B). Western blot assay for the phosphorylated IRF3 expression. PBMC were obtained from 10 SLE patients, 13 RA patients and healthy controls. Proteins were resolved by SDS-PAGE, blotted to nitrocellulose and probed with an antibody to phosphorylated IRF3. The blot was stripped and reprobed with antibody to b-actin to ensure equal loading. A representative blot is shown in FIG. 5C. From in vitro studies, it has been shown that stimulation of TLR7/9 by IC endocytosed from blood or tissue contribute to the IFN signature observed in human SLE. There is precedent for cell intrinsic stimulation of IFN-I by DNA in the Aicardi-Goutierre's Syndrome (AGS) and a subset of SLE patients (Lee-Kirsch, M. A., et al., *Mutations in the gene encoding the 3'-5' DNA exonuclease TREX1 are associated with systemic lupus erythematosus*. Nat Genet, 2007. 39(9): p. 1065-7: Namjou, B., et al., *Evaluation of the TREX1 gene in a large multi-ancestral lupus cohort*. Genes Immun, 2011. 12(4): p. 270-9). We therefore explored the idea that cGAS was implicated in the initiation or perpetuation of IFN stimulation in SLE. We first tested cGAS expression in SLE patients. QPCR obtained from 51 SLE patients and 20 normal controls, revealed that, indeed, cGAS expression was significantly increased in SLE patients compared to normal controls (FIG. 5A). The IFN score and cGAS expression were highly correlated (FIG. 5B). Since cGAS (c6ORF150) is an IFN response genes (ISG) (Schoggins, J. W., et al., *A diverse range of gene products are effectors of the type I interferon antiviral response*. Nature, 2011. 472(7344): p. 481-485), this finding could indicate that cGAS is elevated as a consequence of exposure to IFN-I and/or that cGAS may be induced by an unknown DNA stimulus which then primes for enhanced IFN-I responses in a positive feedback cycle.

cGAS synthesis of cGAMP leads to direct binding and activation of STING which, in turn, causes activation of IRF3 in a TBK dependent pathway. When IRF3 is activated, it becomes phosphorylated, dimerizes and translocates to the nucleus where it exerts its transcriptional function leading to upregulation of IFN-b (Akira, 2010). We therefore tested whether IRF3 was activated in PBMC from SLE patients. As shown in FIG. 5C, when randomly selected SLE, rheumatoid arthritis (RA) and normal PBMC were tested for IRF3 activation, IRF3 phosphorylation was observed in 6 out of 10 SLE patients PBMC but only 2 out of 13 control samples (p=0.028, Fishers exact test). The finding that IRF3 was activated in PBMC from a proportion of SLE patients strongly indicates that this second messenger pathway is active.

GAS is Functional and cGAMP is Expressed in SLE Patients

THP1 cells were transfected with HT-DNA. cGAMP were purified from THP1 cells, SLE patients PBMC and their controls as described in the methods section. The abundance of cGAMP was quantitated by mass spectrometry using SRM. Note that the peak in the SLE cells is derived from m/z of the daughter ions of m/z 673.1 corresponding to cGAMP. This result is pivotal because it proves that not only is the expression of cGAS increased, but also that the enzyme is functional in SLE patient cells and implies activation by DNA. B. cGAMP were purified from PBMC of SLE patients (n=13), RA patients (n=3) and healthy controls (n=6). The presence of cGAMP was measured by mass spectrometry using SRM.

Figure 6:
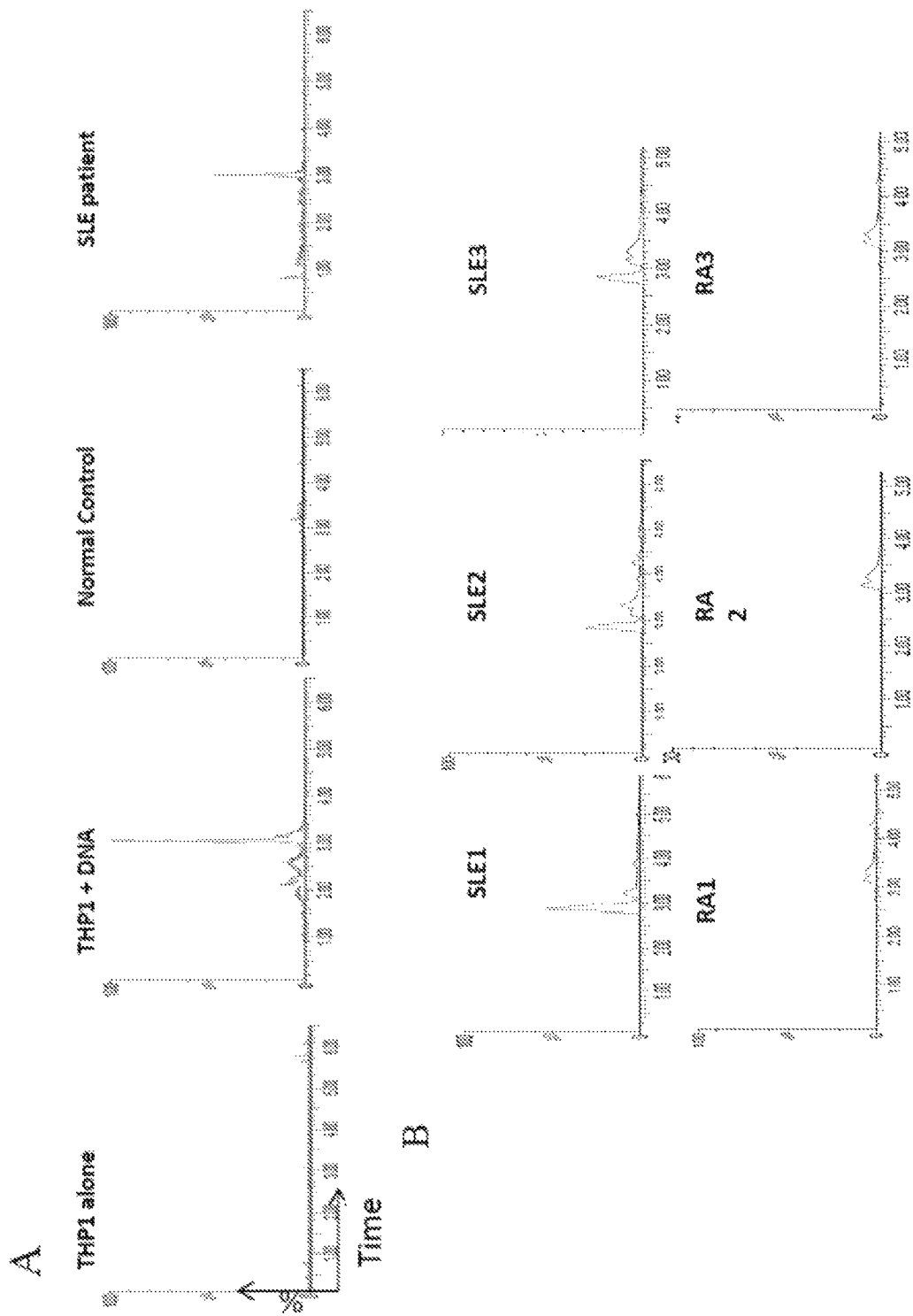
FIG. 6 shows (A) the abundance of cGAMP THP1 cells were transfected with HT-DNA quantized by mass spectrometry using SRM; and (B) the PBMC for cGAMP expression by LC/MS/MS in SLE and RA patients.

Activation of IRF3 could result from stimulation by cGAS or by other pathways such as TLR4, RIG-I or MDA5. To definitively determine whether the cGAS pathway was active in SLE patients, we sought to determine whether cGAMP was expressed in PBMC. We first optimized methods and detected cGAMP in DNA transfected (as well as HSV infected) THP1 cells but not in un-transfected THP1 cells (FIG. 6A). When we tested SLE and healthy control PBMCs, we detected the dinucleotide at exactly 3 minutes in the SLE patient, but not control sample. Note that the peak is derived from m/z of 673.1 corresponding to cGAMP. This result is pivotal because it proves that cGAS in SLE patient cells is functional. We then randomly selected 13 SLE, 6 normal controls and 3 rheumatoid arthritis patients and tested their PBMC for cGAMP expression by LC/MS/MS. Of these 22 samples, 4/13 (31%) SLE, but none of the 9 controls were positive (FIG. 6B). Thus cGAMP is produced in the cells of approximately one third of SLE patients. DNA ICs have been shown to stimulate IL-b in monocytes.

Clinical Features of SLE Patients with cGAS Expression

To determine what clinical, therapeutic or other properties might distinguish those that do and do not express cGAMP, the duration of disease is examined as we postulated that activation of the cGAS pathway may prime cells such as pDC for IFN-a responses. To determine whether drug therapy could explain suppression of cGAMP in about two thirds of patients, hydroxychloroquine, corticosteroid and other therapies are compared. The severity of disease are explored by examining the SLEDAI in each patient.

Materials and Methods

RNA Preparation and Quantitative Real-time PCR

Total RNA was isolated from peripheral mononuclear cells (PBMC) of normal and SLE patients' blood using the RNEASY MINI KIT™ with on column DNASE™ treatment (Qiagen, Valencia, Calif.). cDNA was generated using 25 ng RNA with the high-capacity cDNA RT-KIT™ using random primers (Applied Biosystems, Foster City, Calif.). Reactions in duplicate were run on an ABI STEPONE PLUS™ using cGAS forward primer and backward primer; a two-stage cycle of 95° C. for 15 s and 60° C. for 1 min was repeated for 40 cycles followed by a dissociation stage. Threshold cycle values were set as a constant threshold at 0.2, and fold changes in gene expression were then calculated using the $2^{-\Delta\Delta C_T}$ method.

Western Blot

Cells were lysed in RIPA buffer (25 mM Tris-HCl pH 7.6, 150 mM NaCl, 1% NP-40, 1% sodium deoxycholate, 0.1% SDS) with IX protease inhibitors and phosphatase inhibitors cocktail (Thermal Scientific. Odessa, Tex.), and 20 µg protein from each sample was used for Western blot. The dilution of anti-pIRF3 was 1:500 (Cell Signalling, Danvers, Mass., USA), the dilution of anti-actin was 1:5000 (Santa Cruz Biotechnology, Santa Cruz, Calif., USA). Signals were detected using the ECL™ detection system and film (GE Healthcare, Piscataway, N.J. USA). The quantitation was carried out using FLUORCHEM™ imaging system and software (Alpha Innotech, San Leandro, Calif., USA) with normalizing on the intensity of β-actin.

DNA Stimulation for cGAMP Production

THP1 cells were seeded 35M cells in 35 ML medium at the time of transfection in T175 cell culture flask. 90 ug DNA was diluted in 1.75 ml Serum free medium and 230 ul LIPOFECTAMINE 2000™ reagent was diluted in 1.75 ml serum free medium. Then diluted DNA was added to the tube of diluted LIPOFECTAMINE 2000™ reagent in 1:1 ratio. The DNA and LIPOFECTAMINE™ mixture was incubated for 5 mins at RT and then DNA-regent complex was added to the cells. The transfected cells were cultured in 37 C. incubator for 2 days and then harvested for the cGAMP purifications.

cGAMP Purification

The cells were lysed with NER™ lysis buffer from NE-PER Nuclear and Cytoplasmic Extraction kits (Thermal Scientific, Odessa, Tex.) according to the instruction for the cell volumes vs NER volumes. Spin down the nuclei (~16,000 g for 5 min), take the supernatant and mix this with phenol with 1:1 ratio. Mix, incubate on ice for 5 min, centrifuge for 5 min at 16,000 g at 4° C. Take the upper phase and mix with 2x volumes chloroform. Mix, incubate for 5 min, centrifuge for 5 min at 16,000 g at 4° C. Take the upper phase and transfer it to a molecular weight cut-off column (10,000 MW). Spin as indicated and collect the flow-through. The flow-through was dried by SPEED-VAC™ and resuspended in 20 ul OPTIMA LC/MS™ water (Thermal Scientific, Odessa, Tex.). This was loaded on the HPLC column for Mass Spec analysis.

cGAMP Measurement by UPLC-MS/MS

High resolution mass measurement and tandem MS/MS is performed on Waters XEVO TQS™ Mass Spectrometer coupled with Ultra-Performance Liquid Chromatogram (UPLC). Full scan mass spectra are acquired form m/z 200-800. MS/MS spectra are acquired and the top five most abundant ions subjected to further fragmentation by collision induced dissociation (CID). For targeted quantification of cGAMP, a selective reaction monitoring (SRM) assay was developed on the XEVO TQS™ mass spectrometer. In the assay, three transitions of each target ion are monitored. The parent ion is isolated at m/z 673.1 in a negative mode (M−H)−, fragmented while the resulting daughter ion is monitored at m/z 341.10, 150.05, and 133.93 in a negative mode (M−H)−.

Example 3

Targeted Therapy to Inhibit cGAS Stimulated Type I IFN Production

In an effort to identify drugs to block cGAS activity, we performed in silico screening of chemical and drug libraries and identified a candidate, HCQ, predicted to interact strongly with cGAS. HCQ is FDA approved and has a favorable safety profile.

The compound of Formula (I),

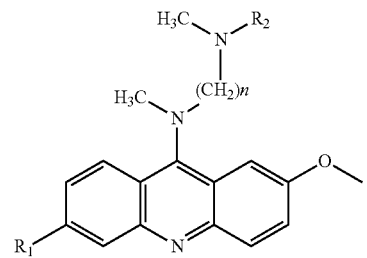

wherein $R_1$ is selected from Cl, OH, $NH_2$, and $NO_2$; $R_2$ is selected from

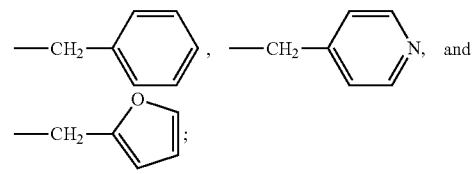

and n is 3 or 4.

The compounds of Formula (I) potently inhibit cGAS resulting in reduced production of IFN-I in lupus as well as autoimmune diseases such as scleroderma, polymyositis and possibly type 1 diabetes that have been associated with increased IFN I.

The design of the compound of Formula (I) started with the energy-minimized structures of X-cGAS and DNA-X-cGAS complexes. Preliminary in silico studies have already identified two potential binding sites that are likely responsible for the blocking of the crucial DNA-cGAS interactions. The compound of Formula (I) has an increased affinity to cGAS while preventing DNA interaction with cGAS. Compounds of Formula (I) were be chemically synthesized and evaluated for binding to cGAS and for their ability to block the formation of DNA-cGAS complexes. They were also tested in cell-based assays (THP-1 production of IFN-b by QPCR) for production of IFN-I. The most promising drug candidates were tested in animal models of lupus and AGS. Compounds of Formula (I) non-toxic to cells were tested in AGS mouse model and lupus mouse model compared with quinacrine (QC) or HCQ as controls. In some aspects the AGS mouse model is TREX1−/−. In some aspects the lupus mouse model is NZB/W.

Synthesis

N, N'-Dimethyl-N'-(6-nitro-2-methoxy-acridin-9-yl)-N-benzylpropane-1,3-diamine (R1=NO2, R2=benzyl, n=3). 6-Nitro-2-methoxy-9-chloroacridine (288 mg, 1 mmol) {Csuk, 2004 #3231} is reacted with N,N'-dimethyl-N-benzylpropane 1,3-diamine (192 mg, 1 mmol) in phenol (10 mL) for 5 hrs at 110° C. After cooled to room temperature, the reaction mixture is diluted with dichloromethane. The mixture is washed twice with sodium hydroxide solution (IN) and twice with ammonium chloride solution. The organic layer is separated, dried over anhydrous sodium sulfate, and concentrated. The residue is purified by silica gel chromatography using triethylamine (5%) and methanol (5 to 15%) in dichloromethane to give the desired compound.

N, N'-Dimethyl-N'-(6-nitro-2-methoxy-acridin-9-yl)-N-(4-pyridyl)propane-1,3-diamine(R1=NO2, R2=4-pyridyl, n=3). Essentially the same reaction as above is carried out by using 6-Nitro-2-methoxy-9-chloroacridine and N,N'-dimethyl-N-(4-pyridyl)propane 1,3-diamine.

N, N'-Dimethyl-N'-(6-nitro-2-methoxy-acridin-9-yl)-N-(2-furanyl)propane-1,3-diamine(R1=NO2, R2=2-furanyl, n=3). Essentially the same reaction as above is carried out by using 6-Nitro-2-methoxy-9-chloroacridine and N,N'-dimethyl-N-(2-furanyl)propane 1,3-diamine.

A hot (60° C.) solution of SnCl2-2H2O (3.5 mol/mol of nitro group) in 12N HCl—AcOH (1:1 v/v) (2 mL/g of SnCl2-2H2O) is added in one portion to finely powdered nitro acridine compound contained in an larger flask. The initial vigor of the reaction is moderated by cooling in tap water. It is essential that at some stage in the reaction a clear solution is obtained. When the vigorous reaction abated the mixture is boiled under reflux for 1.5 hr. After cooling to room temperature, HCL is added to precipitate the crude product. The crude product is dissolved in hot 0.2 N HCl, filtered, and added 12N HCl to precipitate the pure material. The same general method is used to produce the following three compounds; N, N'-Dimethyl-N'-(6-amino-2-methoxy-acridin-9-yl)-N-benzylpropane-1,3-diamine (R1=NH2, R2=benzyl, n=3), N, N'-Dimethyl-N'-(6-amino-2-methoxy-acridin-9-yl)-N-(4-pyridyl)propane-1,3-diamine(R1=NH2, R2=4-pyridyl, n=3), and N, N'-Dimethyl-N'-(6-amino-2-methoxy-acridin-9-yl)-N-(2-furanyl)propane-1,3-diamine (R1=NH2, R2=2-furanyl, n=3).

Example 4

Targeted Therapy to Inhibit cGAS Stimulated Type I IFN Production

The compound of Formula (I),

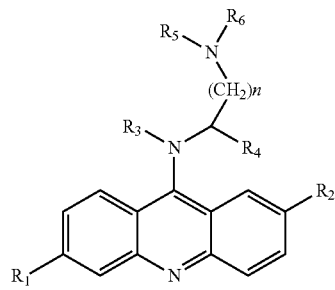

wherein $R_1$ is H, Cl, OH, $NH_2$ or $NO_2$; $R_2$ is H or —$OCH_3$; $R_3$ and $R_4$ are H or $CH_3$; $R_5$ and $R_6$ are H, $CH_3$, —$CH_2CH_2SH$,

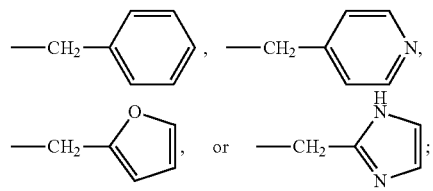

and n is 2 or 3.

The compounds of Formulae (I), (II) and (III) potently inhibit cGAS resulting in reduced production of IFN-I in lupus as well as autoimmune diseases such as scleroderma, polymyositis and possibly type 1 diabetes that have been associated with increased IFN I.

Example 5

Synthesis of Compounds of Formulae (I)-(III)

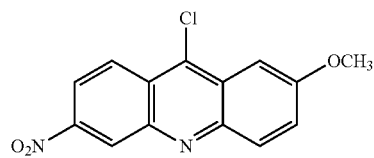 [SMILES: COc1ccc2nc3cc([N+](=O)[O-])ccc3c(Cl)c2c1]

9-Chloro-3-nitro-7-methoxyacridine

9-Chloro-3-nitro-7-methoxyacridine was prepared in two steps according to the published procedure.

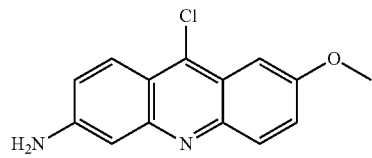 [SMILES: COc1ccc2nc3cc(N)ccc3c(Cl)c2c1]

9-Chloro-3-amino-7-methoxyacridine

In a 10 mL round bottom flask were placed 9-chloro-3-nitro-7-methoxyacridine (0.1 gram, 3.46×10$^4$ mole), Fe powder (58 mg, 1.04×10$^{-3}$ mole), EtOH (0.5 mL), AcOH (2 mL) and H2O (10 μL). Yellow starting material appeared largely insoluble and suspended. Put a glass cap on the flask. Sonicated the mixture at 30~45° C. (started at 30° C. and the bath temperature gradually increased during the sonication) for 50-min, 15 min-break and another 50-min. The solution turned to a deep red color at the end of reaction. Filtered the reaction mixture through a small glass filter to remove excess iron. The insoluble residues were washed with EtOH—AcOH (1:1) and then EtOH. The filtrate and washings were combined and concentrated under vacuum to approximately 1~2 mL. To the viscous red residues, 12NHCl (2 mL) was added, and sonicated briefly. The oily residues turned into solid, and were collected by centrifugation. The products were dried under vacuum. Yield: 0.138 gram (quantitative yield). ESI-MS: m/z=259.1 ([M+H]$^+$).

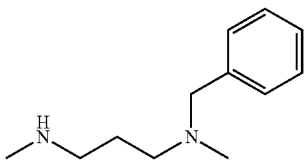

N, N'-Dimethyl-N-benzyl-1,3-propanediamine (X5 arm)

The compound was prepared according to the published procedure. Benzyl chloride (2.0 mL, 0.017 mole) was added drop-wise into a refluxing solution of N, N'-dimethyl-1,3-propanediamine (3.2 mL, 0.026 mole) dissolved in 20 mL THF. White precipitates appeared as the benzyl chloride was added gradually over 30-min. After the addition is complete, the reaction mixture was kept refluxing for another 1 hr. The reaction mixture was then cooled to room temperature, 1M NaOH solution was added and extracted with CH2Cl2. The organic layer was collected, dried over anhydrous Na2SO4, and concentrated. The product was isolated by distillation under reduced pressure. The product boiled at 75~80° C. (0.1 mmHg). Yield 1.29 g (40%).

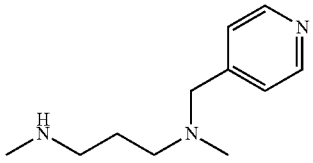

N, N'-Dimethyl-N-(4'-pyridylmethyl)-1,3-propanediamine (X6 arm)

4-chloromethylpyridine HCl (2.79 gram, 0.017 mole) is neutralized with 20 mL of 1M NaOH on an ice bath, and extracted with CH2Cl2 three times. The CH2Cl2 layers were combined and dried over anhydrous Na$_2$SO$_4$. The solvent was evaporated, and the residues were re-dissolved in 5 mL THF. The THF solution was used immediately for the synthesis.

A solution of N, N'-dimethyl-1,3-propanediamine (3.2 mL, 0.026 mole) in 15 mL THF was brought to reflux, and the THF solution of 4-chloromethylpyridine was added dropwise over 30-min. After the addition, the dropping funnel was washed with 5 mL THF. After the addition is complete, the reaction mixture was kept refluxing for another 1 hr. White precipitates were formed. The reaction mixture was then cooled to room temperature, and the solvent was removed under vacuum. To the residue was added 1M NaOH, and the product was extracted CH2Cl2 three times. The organic layers were combined, and dried over anhydrous Na2CO3. The CH2Cl2 solution was concentrated, and the product was isolated by distillation under reduced pressure. The product boiled at 90~95° C. (0.1 mmHg), Yield 1.33 gram (41%). $^1$H-NMR (300 MHz, CDCl$_3$): δ (ppm) 8.54 (2H, d), 7.26 (2H, d), 3.48 (2H, s), 2.62 (2H, t), 2.41 (3H, s), 2.41 (2H, t), 2.20 (3H, s), 1.70 (2H, quintet), 1.51 (1H, br. s).

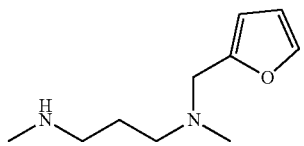

N, N'-Dimethyl-N-furfuryl-1,3-propanediamine (X7 arm)

Furfuryl chloride (2.0 mL, 0.017 mole) was added dropwise into a refluxing solution of N, N'-dimethyl-1,3-propanediamine (3.2 mL, 0.026 mole) dissolved in 20 mL THF. White precipitates were observed as furfuryl chloride was added gradually over 30-min. After the addition is complete, the reaction mixture was kept refluxing for another 1 hr. The reaction mixture was then cooled to room temperature, 1M NaOH solution was added, and extracted with CH2Cl2. The organic layers were combined, dried over anhydrous Na2SO4 and concentrated. The product was isolated by distillation under reduced pressure. The product boiled at 60-65° C. (0.1 mmHg). Yield 1.16 g (37%). $^1$H-NMR (300 MHz, CDCl$_3$): δ (ppm) 7.37 (1H, m), 6.31 (1H, m), 6.17 (1H, m), 3.55 (2H. s), 2.61 (2H, t), 2.40 (3H. s), 2.40 (2H, t), 2.24 (3H, s), 1.70 (2H, quintet), 1.84 (1H, br. s).

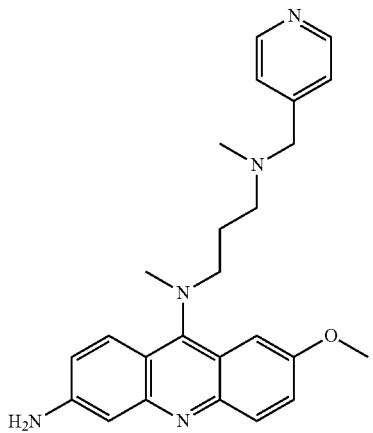 [SMILES: COc1ccc2nc3cc(N)ccc3c(N(C)CCCN(C)Cc3ccncc3)c2c1]

9-(N-(4''-pyridylmethyl)-N-methyl-N'-methyl-1',3'-propanediamine))-3-amino-7-methoxyacridine (X6)

The dark red powder of crude 9-Chloro-3-amino-7-methoxyacridine prepared from 0.2 gram of the corresponding nitro compound was placed in 50 mL flask, and added 2 mL of EtOH, X6 arm (0.25 gram) and triethylamine (300 µL). The mixture was sonicated briefly to make a suspension, and then heated to reflux on an oil bath. The reflux was continued with stirring for 5 hrs. The solvent was removed under vacuum. The residues were dissolved in 10 mL CH2Cl2 with sonication. Some insoluble materials were visible. Apply the whole suspension to a silica gel column (12 g in CH2Cl2). The column was washed with 50 mL CH2Cl2, and then eluted with 9:1:0.1 (CH2Cl2, MeOH, NH4OH) 100 mL. Collected the dark red fraction, and concentrated with under vacuum. The residues were dried under vacuum overnight. Yield 0.39 gram. The crude material was dissolved in DMF and purified by HPLC, C18 reverse phase and a standard acetonitrile-water-0.1% TFA linier gradient. The purified X6 was lyophilized to produce orange powder. ESI-MS: m/z=416.3 ([M+H]$^+$).

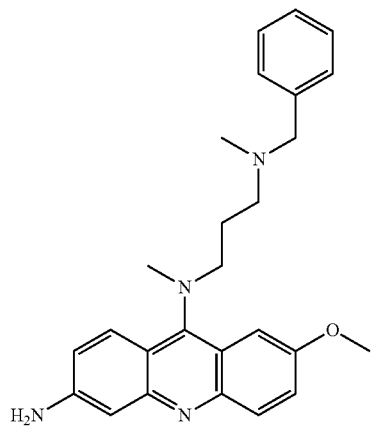 [SMILES: COc1ccc2nc3cc(N)ccc3c(N(C)CCCN(C)Cc3ccccc3)c2c1]

9-(N-benzyl-N-methyl-N'-methyl-1',3'-propanediamine)-3-amino-7-methoxyacridine (X5)

X5 was prepared by the same procedure as for X6 by using X5 arm. ESI-MS: m/z=415.5 ([M+H]$^+$)

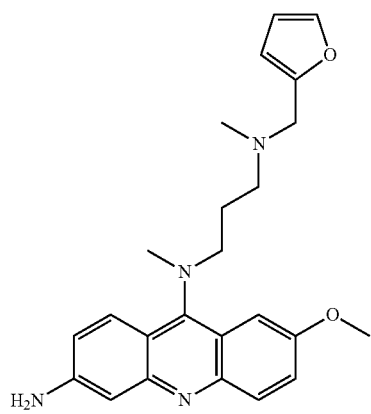 [SMILES: COc1ccc2nc3cc(N)ccc3c(N(C)CCCN(C)Cc3ccco3)c2c1]

9-(N-furfuryl-N-methyl-N'-methyl-1',3'-propanediamine)-3-amino-7-methoxyacridine (X7)

X7 was prepared by the same procedure as for X6 by using X7 arm. ESI-MS: m/z=405.2 ([M+H]$^+$)

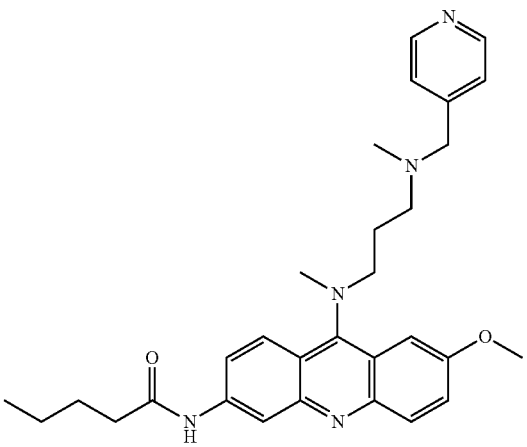 [SMILES: CCCCC(=O)Nc1ccc2c(N(C)CCCN(C)Cc3ccncc3)c3cc(OC)ccc3nc2c1]

9-(N-(4''-pyridylmethyl)-N-methyl-N'-methyl-1',3'-propanediamine))-3-n-butoxyamino-7-methoxyacridine (C6X6)

X6 (5 mg, 1.2×10-5 mole) was suspended in 1 mL CH2Cl2, and triethylamine (8.4 µL, 6×10-5 mole) was added. Slight color changes occurred from orange to yellow. Sonicated the mixture for 1 min, and n-hexanoyl chloride (3.4 µL, 2.4×10-4 mole) was added by using a 10 uL syringe. White fume appeared. The yellow color intensified with disappearance of suspended small particles of X6. The mixture was kept at room temperature. The color changed to yellow-green after 2 hrs. HPLC showed a major peak that appears to be more hydrophobic than X6. The reaction was then quenched by adding 50 uL of methanol. The product was purified by C18 reverse phase HPLC with a standard acetonitrile-water-0.1% TFA gradient. Yield 6.4 mg (100%). ESI-MS: m/z=524.4 ([M+H]$^+$)

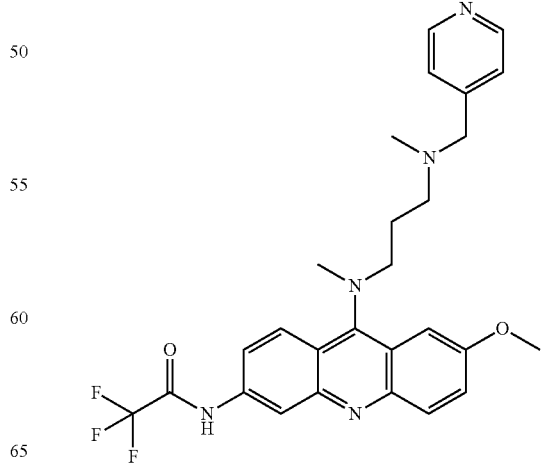

157
9-(N-(4"-pyridylmethyl)-N-methyl-N'-methyl-1',3'-propanediamine))-3-trifluoroacetylamide-7-methoxyacridine (TFAX6)

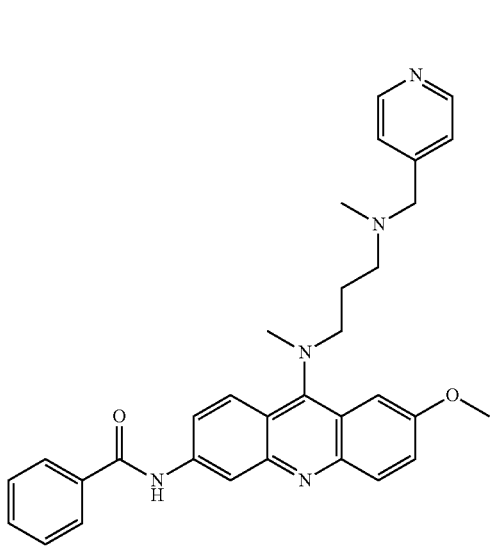 [SMILES: COc1ccc2nc3cc(NC(=O)c4ccccc4)ccc3c(N(C)CCCN(C)Cc3ccncc3)c2c1]

158
9-(N-(4"-pyridylmethyl)-N-methyl-N'-methyl-1',3'-propanediamine))-3-benzamide-7-methoxyacridine (BzX6)

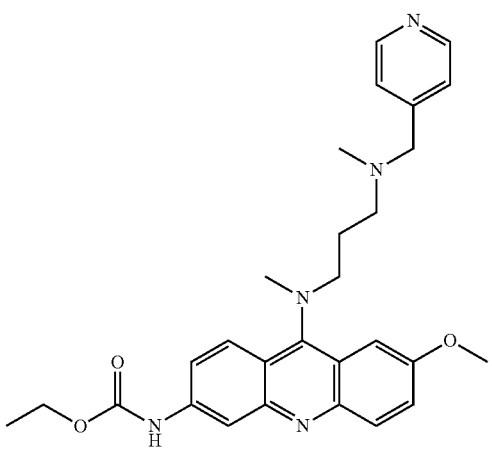 [SMILES: CCOC(=O)Nc1ccc2c(N(C)CCCN(C)Cc3ccncc3)c3cc(OC)ccc3nc2c1]

9-(N-(4"-pyridylmethyl)-N-methyl-N'-methyl-1',3'-propanediamine))-3-ethoxycarbonyl-7-methoxyacridine (ETOX6)

TFAX6, BzX6 and ETOX6 were prepared by using the same procedure as that for C6X6, starting from purified X6 and trifluoroacetic anhydride, benzoyl chloride or chloroethylcarbonate as an acylating agent, respectively. The reaction product was purified by reverse phase HPLC, and the product was more hydrophobic than X6.

TABLE 1

| | $IC_{50}$ Data | | |
|---|---|---|---|
| No. | Structure | $IC_{50}$ Enzyme Assay (μM) | Toxicity[1] (μM) |
| 1 (HCQ) | | 350 | — |
| 2 (CQ) | | 850 | — |

TABLE 1-continued

IC$_{50}$ Data

| No. | Structure | IC$_{50}$ Enzyme Assay (μM) | Toxicity[1] (μM) |
|---|---|---|---|
| 3 (PQ) | [structure] | 850 | — |
| 4 (QC/QQ) | [structure] | 13 | 33.0 |
| 5 (QN) | [structure] | 2000 | — |
| 6 (AMCA QQore) | [structure] | 32 | — |
| 7 | [structure] | 10 | — |
| 8 | [structure] | 5 | — |

TABLE 1-continued

IC$_{50}$ Data

| No. | Structure | IC$_{50}$ Enzyme Assay (μM) | Toxicity[1] (μM) |
|---|---|---|---|
| 9 | *structure: tryptophan-acridine conjugate* | >650 | — |
| 10 | *structure: ethyl 4-(acridin-9-ylamino)benzoate* | >650 | — |
| 11 | *structure: N-(3-nitrophenyl)acridin-9-amine* | >650 | — |
| 12 | *structure: methanesulfonamide-methoxyphenyl-acridinamine* | >650 | — |
| 13 (X5) | | 18 | 33.1 |
| 14 (X6) | | 23 | 27.4 |
| 15 (X7) | | 35 | — |

TABLE 1-continued
| | | IC$_{50}$ Data | |
|---|---|---|---|
| No. | Structure | IC$_{50}$ Enzyme Assay (μM) | Toxicity[1] (μM) |
| 16 (C6X6) | 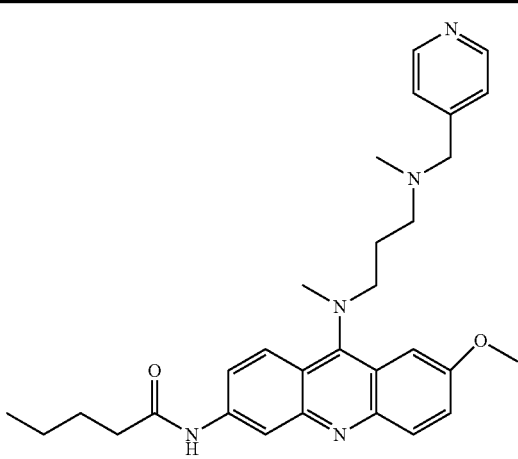 | — | — |
| 17 (TFAX6) | 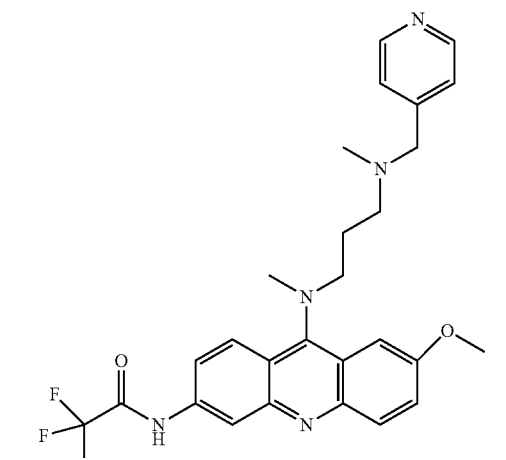 | — | — |
| 18 (BzX6) | 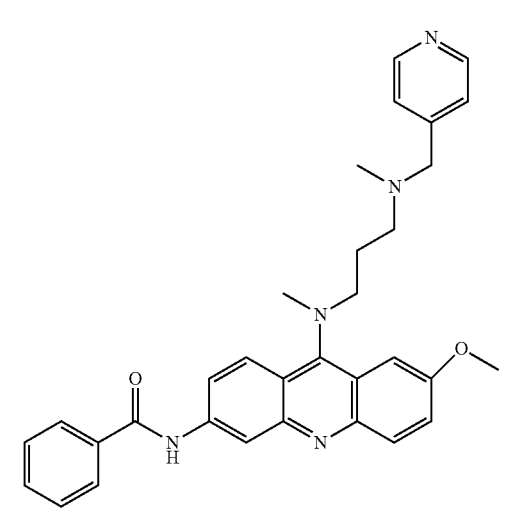 [SMILES: COc1ccc2nc3cc(NC(=O)c4ccccc4)ccc3c(N(C)CCCN(C)Cc3ccncc3)c2c1] | — | — |

TABLE 1-continued

IC$_{50}$ Data

| No. | Structure | IC$_{50}$ Enzyme Assay (μM) | Toxicity[1] (μM) |
|---|---|---|---|
| 19 | 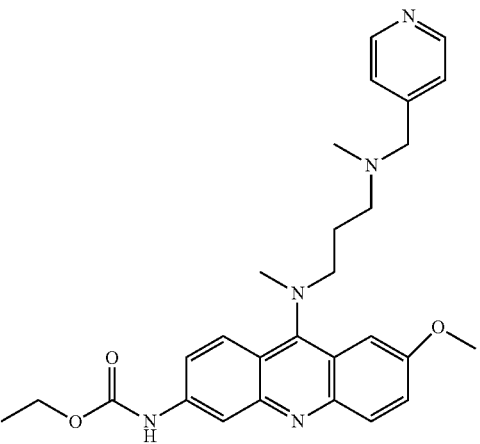 [SMILES: CCOC(=O)Nc1ccc2c(N(C)CCCN(C)Cc3ccncc3)c3cc(OC)ccc3nc2c1] | — | — |
| 20 | 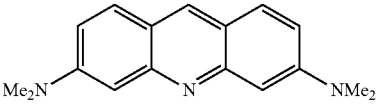 [SMILES: CN(C)c1ccc2cc3ccc(N(C)C)cc3nc2c1] | 8 | — |
| 21 | 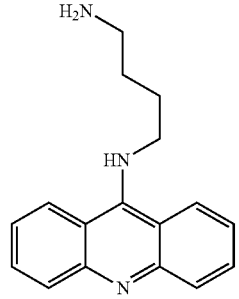 [SMILES: NCCCCNc1c2ccccc2nc2ccccc12] | 1 | 16.0 |

[1]Average of 3 cell lines @ 50% cell death

TABLE 2

AutoDock VINA™

| No. | PDB 4LEZ (mcGAS + dsDNA DIMER SITE II) ΔG | PDB 4K97 (mcGAS + dsDNA MONOMER C CHAIN) ΔG | PDB 4K98 (mcGAS + dsDNA MONOMER A CHAIN) ΔG | PDB 4K8V (mCGAS NO dsDNA) ΔG | dsDNA (EF) ΔG | dsDNA (IJ) ΔG |
|---|---|---|---|---|---|---|
| 1 | −7.0 | −5.7 | −6.4 | −5.2 | −6.4 | −6.3 |
| 2 | −6.7 | −5.8 | −5.9 | −5.1 | −6.2 | −6.2 |
| 3 | −6.8 | −5.7 | −6.7 | −5.3 | −6.2 | −6.0 |
| 4 | −8.0 | −6.8 | −6.0 | −5.2 | −6.9 | −6.4 |
| 5 | −8.2 | −6.6 | −7.2 | −5.7 | −7.0 | −7.1 |
| 6 | −7.7 | −7.1 | −7.3 | −5.9 | −7.2 | −6.8 |
| 7 | −8.2 | −7.2 | −7.6 | −6.2 | −7.1 | −6.8 |
| 8 | −7.3 | −6.5 | −6.6 | −5.7 | −6.8 | −6.3 |
| 9 | −9.3 | −8.1 | −8.1 | −6.9 | −8.4 | −7.9 |
| 10 | −8.8 | −8.5 | −7.5 | −6.4 | −7.1 | −7.2 |
| 11 | −9.3 | −8.6 | −7.7 | −6.7 | −7.5 | −7.5 |
| 12 | −8.5 | −7.5 | −8.0 | −6.2 | −7.5 | −7.5 |
| 13 | −9.5 | −6.2 | −7.2 | −5.5 | −7.4 | −7.3 |
| 14 | −9.0 | −7.9 | −7.3 | −6.1 | −7.7 | −7.3 |
| 15 | −9.2 | −8.1 | −7.4 | −5.1 | −7.4 | −7.5 |
| 20 | −7.8 | −7.0 | −7.0 | −5.4 | −7.3 | −7.3 |
| 21 | −7.5 | −6.7 | −6.8 | −6.6 | NA | −7.5 |

What is claimed:

1. A compound of Formula (I) or a prodrug thereof,

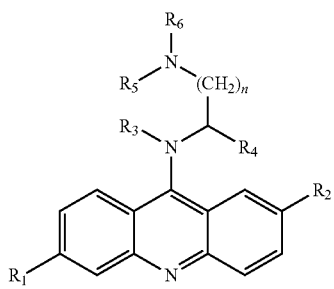

(I)

wherein $R_1$ is —OH, —NH$_2$, —N(H)C(O)R$_7$ or —NO$_2$;
$R_2$ is —H or —OCH$_3$;
$R_3$ and $R_4$ are independently —H or —CH$_3$;
$R_5$ and $R_6$ are independently —H, —CH$_3$, —CH$_2$CH$_2$SH,

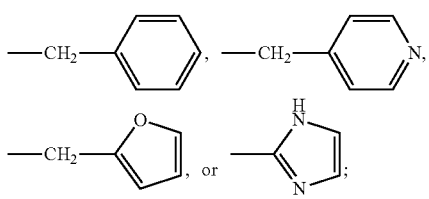

, or $R_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

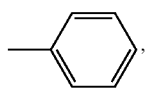

, and n is 2 or 3.

2. The compound of claim 1, wherein $R_1$ is —NH$_2$ or —N(H)C(O)R$_7$;
$R_2$ is —OCH$_3$;
$R_3$ is —CH$_3$;
$R_4$ is —H;
$R_5$ is —CH$_3$;
$R_6$ is

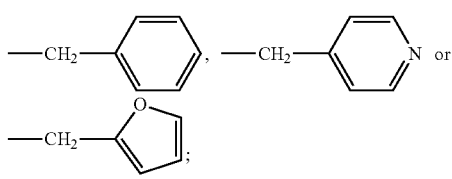

$R_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

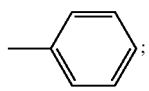

;

and n is 2.

3. The compound of claim 1, wherein
R$_1$ is —NH$_2$ or —N(H)C(O)R$_7$;
R$_2$ is —OCH$_3$;
R$_3$ is —CH$_3$;
R$_4$ is —H;
R$_5$ is —CH$_3$;
R$_6$ is

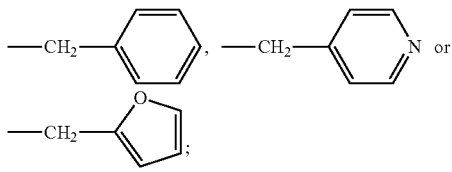

R$_7$ is —OCH$_2$CH$_3$, —CH$_2$CH$_2$CH$_2$CH$_2$CH$_3$, —CF$_3$ or

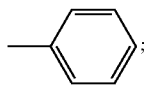

and
n is 2.
4. The compound of claim 1, wherein
R$_1$ is —NH$_2$;
R$_2$ is —OCH$_3$;
R$_3$ is —CH$_3$;
R$_4$ is —H;
R$_5$ is —CH$_3$;
R$_6$ is

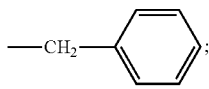

and
n is 2.
5. The compound of claim 2, wherein
R$_1$ is —NH$_2$;
R$_2$ is —OCH$_3$;
R$_3$ is —CH$_3$;
R$_4$ is —H;
R$_5$ is —CH$_3$;
R$_6$ is

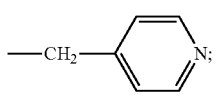

and
n is 2.
6. The compound of claim 2, wherein
R$_1$ is —NH$_2$;
R$_2$ is —OCH$_3$;
R$_3$ is —CH$_3$;
R$_4$ is —H;
R$_5$ is —CH$_3$;
R$_6$ is

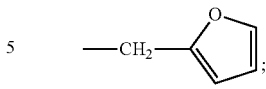

and
n is 2.
7. The compound of claim 2, wherein R$_1$ is N(H)C(O)R$_7$.
8. The compound of claim 2, wherein
R$_1$ is —N(H)C(O)R$_7$;
R$_2$ is —OCH$_3$;
R$_3$ is —CH$_3$;
R$_4$ is —H;
R$_5$ is —CH$_3$;
R$_6$ is

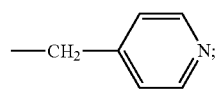

and
n is 2.
9. The compound of claim 2, wherein
R$_1$ is —N(H)C(O)CH$_2$CH$_2$CH$_2$CH$_2$CH$_3$;
R$_2$ is —OCH$_3$;
R$_3$ is —CH$_3$;
R$_4$ is —H;
R$_5$ is —CH$_3$;
R$_6$ is

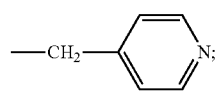

and
n is 2.
10. The compound of claim 2, wherein
R$_1$ is —N(H)C(O)CF$_3$;
R$_2$ is —OCH$_3$;
R$_3$ is —CH$_3$;
R$_4$ is —H;
R$_5$ is —CH$_3$;
R$_6$ is

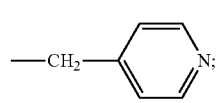

and
n is 2.
11. The compound of claim 2, wherein
R$_1$ is —N(H)C(O)R$_7$;
R$_2$ is —OCH$_3$;
R$_3$ is —CH$_3$;
R$_4$ is —H;
R$_5$ is —CH$_3$;

R₆ is

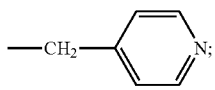

R₇ is

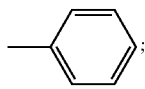

and
n is 2.

12. A compound of Formula (II) or a prodrug thereof,

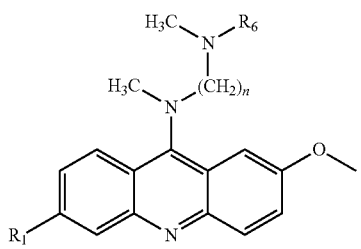

(II)

wherein
R₁ is —Cl, —OH, —NH₂, or —NO₂;
R₆ is

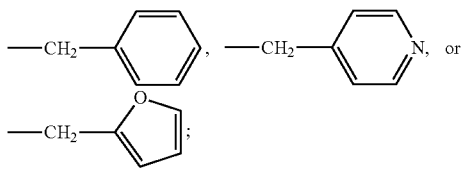

and
n is 3 or 4.

13. A compound of Formula (I) or a prodrug thereof,

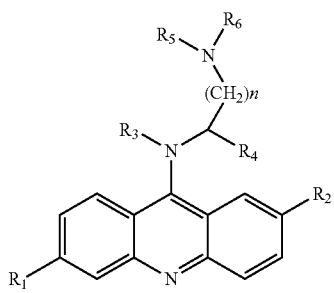

(I)

wherein
R₁ is —H, —Cl, —OH, —NH₂ or —NO₂;
R₂ is —H or —OCH₃;
R₃ and R₄ are independently —H or —CH₃;
R₅ and R₆ are independently —H, —CH₃, —CH₂CH₂SH,

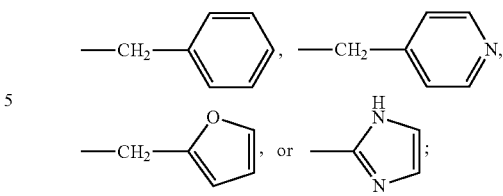

and
n is 2 or 3.

14. The compound of claim 13, wherein R₁ is —NH₂; R₂ is —OCH₃; R₃ is —CH₃; R₄ is —H; R₅ is —CH₃; R₆ is

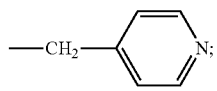

and n is 2.

15. A pharmaceutical composition comprising a compound of claim 1 and a pharmaceutically acceptable carrier, diluent or excipient.

16. A method for the treatment of an autoimmune disease or a monogenic disorder, the method comprising administering an effective amount of a compound of claim 1 or a prodrug thereof, to a patient in need thereof, wherein the autoimmune disease is selected from the group consisting of systemic lupus erythematosus, inflammatory bowel disease, diabetes mellitus, Sjögren's syndrome, scleroderma, and polymyositis, and wherein the monogenic disorder is Aicardi-Goutiéres's Syndrome.

17. A method for the treatment of an autoimmune disease or a monogenic disorder, the method comprising administering an effective amount of a compound of Formula (III) or a prodrug thereof,

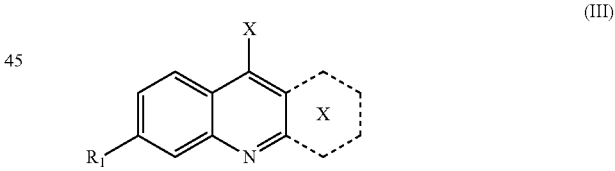

(III)

wherein
R₁ is —H, halogen, —OH, —OCH₃, —NH₂, —NMe₂, —N(H)C(O)R₇ or —NO₂,
wherein R₇ is —OCH₃, —OCH₂CH₃, —OCH₂CH₂CH₃, —OCH₂CH₂CH₂CH₃, —CH₃, —CH₂CH₃, —CH₂CH₂CH₃, —CH₂CH₂CH₂CH₃, —CH₂CH₂CH₂CH₂CH₃, —CH₂CH₂CH₂CH₂CH₂CH₃, —CF₃, —CH₂CF₃ or

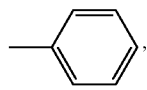

ring X is absent or

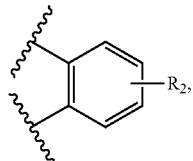

wherein R$_2$ is —H, halogen, —NMe$_2$, —OCH$_3$ or —OCH$_2$CH$_3$;

X is —H, —NH$_2$,

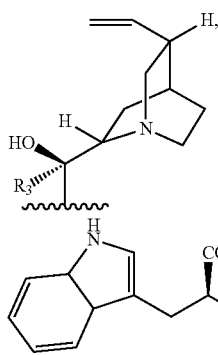

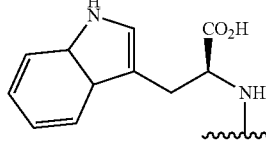

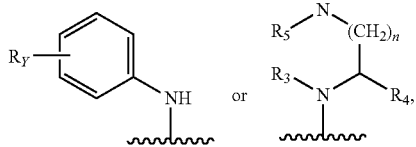

wherein

R$_3$ is —H or —CH$_3$;

R$_4$ is —H or —CH$_3$;

R$_5$ and R$_6$ are independently —H, —CH$_3$, —CH$_2$CH$_3$, —CH$_2$CH$_2$SH, —CH$_2$CH$_2$OH,

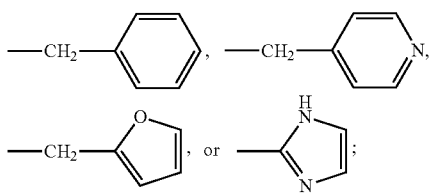

R$_Y$ is —NO$_2$, —C(O)OCH$_2$CH$_3$ or —N(H)SO$_2$Me; and n is 2 or 3;

to a patient in need thereof, wherein the autoimmune disease is selected from the group consisting of systemic lupus erythematosus, inflammatory bowel disease, diabetes mellitus, Sjögren's syndrome, scleroderma, and polymyositis, and wherein the monogenic disorder is Aicardi-Goutiéres's Syndrome.

18. The method of claim 17, wherein the compound is of formula (IIIa):

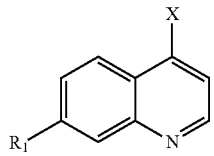

(IIIa)

wherein

R$_1$ is —H, halogen, —OH, —OCH$_3$, —NH$_2$, —N(H)C(O)R$_7$ or —NO$_2$, wherein R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$ CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

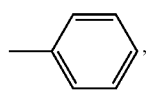

X is

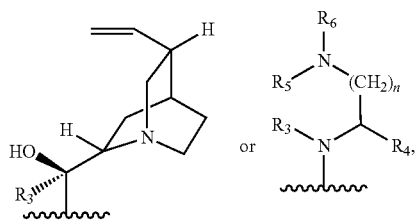

wherein

R$_3$ is —H or —CH$_3$;

R$_4$ is —H or —CH$_3$;

R$_5$ and R$_6$ are independently —H, —CH$_3$, —CH$_2$CH$_3$ or —CH$_2$CH$_2$OH; and n is 2 or 3.

19. The method of claim 17, wherein the compound is of formula (IIIb):

(IIIb)

wherein

R$_1$ is —H, halogen, —OH, —OCH$_3$, —NH$_2$, —N(H)C(O)R$_7$ or —NO$_2$, wherein R$_7$ is —OCH$_3$, —OCH$_2$CH$_3$, —OCH$_2$CH$_2$CH$_3$, —OCH$_2$CH$_2$CH$_2$CH$_3$, —CH$_3$, —CH$_2$CH$_3$, —CH$_2$ CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CF$_3$, —CH$_2$CF$_3$ or

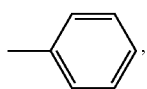
$R_2$ is H, halogen, —OCH$_3$ or —OCH$_2$CH$_3$;
X is —NH$_2$,
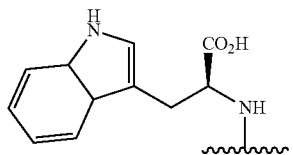
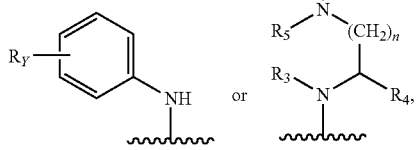
wherein
$R_3$ is —H or —CH$_3$;
$R_4$ is —H or —CH$_3$;
$R_5$ and $R_6$ are independently —H, —CH$_3$, —CH$_2$CH$_3$, —CH$_2$CH$_2$SH, —CH$_2$CH$_2$OH,
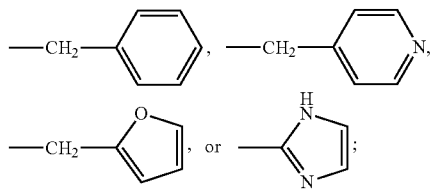
$R_Y$ is —NO$_2$, —C(O)OCH$_2$CH$_3$ or —N(H)SO$_2$Me; and
n is 2 or 3.
20. The method of claim 16, for the treatment of systemic lupus erythematosus.
21. The method of claim 16, for the treatment of Aicardi-Goutiéres's Syndrome.
\* \* \* \* \*

SEQUENCE LISTING

<160> NUMBER OF SEQ ID NOS: 2

<210> SEQ ID NO 1
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 1

```
acatctagta catgtctagt cagtatctag tgattatcta gacatacatc tagtacatgt    60
ctagtcagta tctagtgatt atctagacat ggactcatcc                         100
```

<210> SEQ ID NO 2
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 2

```
ggatgagtcc atgtctagat aatcactaga tactgactag acatgtacta gatgtatgtc    60
tagataatca ctagatactg actagacatg tactagatgt                         100
```